United States Patent [19]

Dumas

[11] Patent Number: 4,956,005

[45] Date of Patent: Sep. 11, 1990

[54] HERBICIDAL ORTHOSULFONAMIDE BENZENE SULFONYLUREAS

[75] Inventor: Donald J. Dumas, Wilmington, Del.

[73] Assignee: E. I. du Pont de Nemours and Company, Wilmington, Del.

[21] Appl. No.: 271,155

[22] Filed: Nov. 14, 1988

Related U.S. Application Data

[60] Division of Ser. No. 810,336, Dec. 23, 1985, Pat. No. 4,802,906, which is a continuation-in-part of Ser. No. 703,669, Feb. 21, 1985, abandoned.

[51] Int. Cl.$^5$ ............... A01N 43/66; A01N 43/68; A01N 43/70; C07D 251/52
[52] U.S. Cl. ............................ 71/93; 71/86; 71/87; 544/113; 544/219; 544/195; 544/198; 544/197; 544/206; 544/211; 544/208; 544/212; 544/207; 544/209
[58] Field of Search ............... 71/93, 86, 87; 544/113, 544/198, 211, 207, 219, 195, 197, 206, 208, 212, 209

[56] References Cited

U.S. PATENT DOCUMENTS

| | | | |
|---|---|---|---|
| 4,310,346 | 1/1982 | Levitt | 71/93 |
| 4,339,267 | 7/1982 | Levitt | 71/92 |
| 4,478,635 | 10/1984 | Meyer et al. | 71/92 |
| 4,487,626 | 12/1984 | Zimmerman | 71/90 |
| 4,496,392 | 1/1985 | Levitt | 71/93 |
| 4,626,273 | 12/1986 | Shiokawa et al. | 71/92 |
| 4,658,027 | 4/1987 | Diehr et al. | 544/321 |
| 4,666,505 | 5/1987 | Diehr et al. | 71/92 |
| 4,671,819 | 6/1987 | Meyer et al. | 71/93 |

FOREIGN PATENT DOCUMENTS

| | | |
|---|---|---|
| 83/16890 | 1/1984 | Austria . |
| 57546 | 8/1982 | European Pat. Off. . |
| 135332 | 3/1985 | European Pat. Off. . |
| 166668 | 8/1985 | Japan . |
| 85/6586 | 2/1986 | South Africa . |

*Primary Examiner*—John M. Ford
*Attorney, Agent, or Firm*—James A. Costello

[57] ABSTRACT

Ortho-Sulfonamide benzenesulfonylureas, such as N-cyclopropyl-N'-[(4,6-dimethoxypyrimidin-2-yl)aminocarbonyl]-1,2-benzenedisulfonamide, are useful as pre-emergent and post-emergent herbicides.

33 Claims, No Drawings

HERBICIDAL ORTHOSULFONAMIDE BENZENE SULFONYLUREAS

This is a divisional application of application Ser. No. 810,336, filed on Dec. 23, 1985, now U.S. Pat. No. 4,802,906 which is a continuation-in-part of application Ser. No. 703,669, filed on Feb. 21, 1985, now abandoned.

BACKGROUND OF THE INVENTION

Certain ortho-aminosulfonyl benzenesulfonylureas are known as herbicides. U.S. Pat. No. 4,310,346 discloses, in part, herbicidal sulfonamides of formula

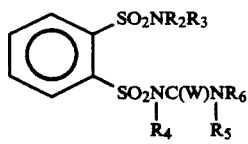

wherein:
$R_2$ is H, $C_1$ to $C_6$ alkyl, $C_3$ to $C_4$ alkenyl, $C_3$ to $C_6$ cycloalkyl, $C_4$ to $C_7$ cycloalkylalkyl, $C_5$ to $C_6$ cycloalkenyl, $C_3$ to $C_5$ alkynyl, $C_3$ to $C_6$ cycloalkyl substituted with 1-2 $CH_3$ groups, $CF_2CF_2H$, $CF_2CHFCl$, $CF_2CHFBr$, $CF_2CHFCF_3$, $C(CH_3)_2CN$, $(CH_2)_mCN$, where m is 1 or 2, $CH_2CH_2OCH_3$, $CH_2CH(CH_3)OCH_3$, $(CH_2)_3OCH_3$, $CHR_7CO_2R_8$ or $CHR_7CON(R_8)_2$; and
$R_3$ is $C_1$ to $C_4$ alkyl, $C_3$ to $C_4$ alkenyl, $CH_2CH_2OCH_3$, $CH_2CH(CH)_3OCH_3$, $CH_2CF_3$ or $(CH_2)_mCN$, where m is 1 or 2 or $CHR_7CO_2R_8$.

U.S. Pat. No. 4,478,635 discloses, in part, herbicidal sulfonamides of formula

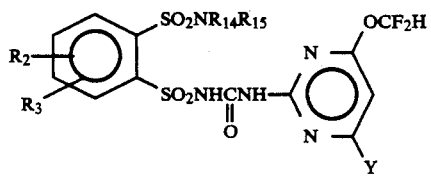

wherein:
$R_{14}$ is H, $OCH_3$, $OC_2H_5$, $C_1$ to $C_4$ alkyl or $CO_2R_{12}$; and
$R_{15}$ is H or $C_1$ to $C_4$ alkyl.

EPA No. 84305305.9 discloses, in part, herbicidal sulfonylureas of formula

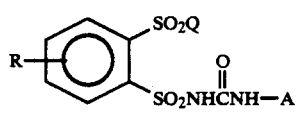

wherein:
Q is $NR_1R_2$,

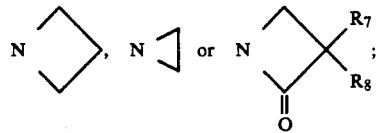

$R_1$ is H, $C(O)R_3$, $C(O)NR_4R_5$, $CO_2R_6$, $C(O)NHR_9$ or $CF_2H$; and
$R_2$ is H or $C_1$ to $C_3$ alkyl.

U.S. Pat. No. 4,339,267 discloses, in part, herbicidal sulfonamides of formula

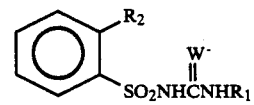

wherein:
$R_1$ is

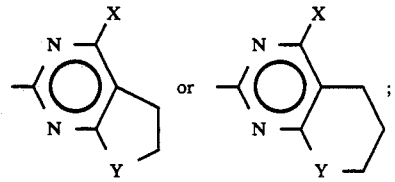

$R_2$ is, among others, $SO_2NR_{10}R_{11}$ or $SO_2N(OCH_3)CH_3$; and
$R_{10}$ and $R_{11}$ are independently $C_1$ to $C_6$ alkyl or $C_3$ to $C_4$ alkenyl or $R_{10}$ and $R_{11}$ can be taken together to be $(CH_2)_4$, $(CH_2)_5$ or $O(CH_2CH_2)_2$.

U.S. Pat. No. 4,496,392 discloses, in part, herbicidal sulfonamides of formula

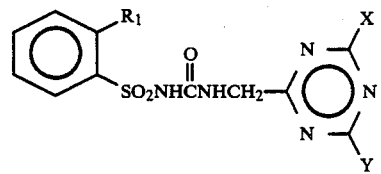

wherein:
$R_1$ is, among others, $SO_2NR_8R_9$ or $SO_2N(CH_3)OCH_3$;
$R_8$ is $CH_3$; and
$R_9$ is $C_1$ to $C_3$ alkyl.

U.S. Pat. No. 4,487,626 discloses, in part, herbicidal sulfonamides of formula

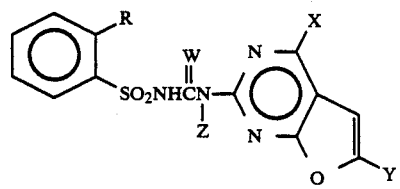

wherein:
R is, among others, $SO_2NR^6R^7$ or $SO_2N(OCH_3)CH_3$; and $R^6$ and $R^7$ are independently $C_1$ to $C_4$ alkyl, provided that the total number of carbon atoms of $R^6$ and $R^7$ is less than or equal to 5.

Japanese Patent Application No. 60-166668 (laid open 8/29/85) discloses herbicidal sulfonamides of the formula

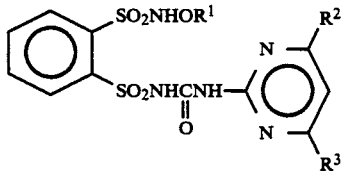

wherein:

$R^1$, $R^2$ and $R^3$ are lower alkyl.

SUMMARY OF THE INVENTION

This invention pertains to compounds of Formula I, agriculturally suitable compositions containing them and their method-of-use as general and/or selective preemergent and/or postemergent herbicides or plant growth regulators. The compounds are:

$$\underset{R}{JSO_2NHC\overset{\overset{W}{\|}}{N}A} \qquad I$$

and their agriculturally suitable salts, wherein:

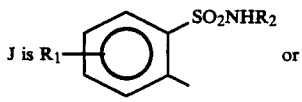

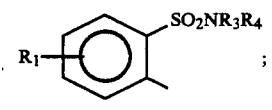

W is O or S;
R is H or $CH_3$;
$R_1$ is H, $C_1$ to $C_3$ alkyl, $C_1$ to $C_3$ haloalkyl, halogen, nitro, $C_1$ to $C_3$ alkoxy, $SO_2NR_aR_b$, $C_1$ to $C_3$ alkylthio, $C_1$ to $C_3$ alkylsulfinyl, $C_1$ to $C_3$ alkylsulfonyl, CN, $CO_2R_c$, $C_1$ to $C_3$ haloalkoxy, $C_1$ to $C_3$ haloalkylthio, $C_2$ to $C_3$ alkoxyalkyl, $C_2$ to $C_3$ haloalkoxyalkyl, $C_2$ to $C_3$ alkylthioalkyl, $C_2$ to $C_3$ haloalkylthioalkyl, $C_2$ to $C_3$ cyanoalkyl or $NR_dR_e$;
$R_a$ is H, $C_1$ to $C_4$ alkyl, $C_2$ to $C_3$ cyanoalkyl, methoxy or ethoxy;
$R_b$ is H, $C_1$ to $C_4$ alkyl or $C_3$ to $C_4$ alkenyl; or
$R_a$ and $R_b$ can be taken together as $-(CH_2)_3-$, $-(CH_2)_4-$, $-(CH_2)_5-$ or $-CH_2CH_2OCH_2CH_2-$;
$R_c$ is $C_1$ to $C_4$ alkyl, $C_3$ to $C_4$ alkenyl, $C_3$ to $C_4$ alkynyl, $C_2$ to $C_4$ haloalkyl, $C_2$ to $C_3$ cyanoalkyl, $C_5$ to $C_6$ cycloalkyl, $C_4$ to $C_7$ cycloalkylalkyl or $C_2$ to $C_4$ alkoxyalkyl;
$R_d$ and $R_e$ are independently H or $C_1$ to $C_2$ alkyl;
$R_2$ is $C_5$ to $C_6$ alkyl, $C_5$ to $C_6$ alkenyl, $C_2$ to $C_6$ haloalkenyl, $C_3$ to $C_6$ alkynyl, $C_3$ to $C_6$ cycloalkyl, $C_3$ to $C_6$ cycloalkyl optionally substituted with 1 or 2 $CH_3$ groups, $C_4$ to $C_7$ cycloalkylalkyl, $C_5$ to $C_6$ cycloalkenyl, $C_3$ to $C_6$ epoxyalkyl, $C_2$ to $C_6$ haloalkyl, $CH_2CH(OR_5)_2$,

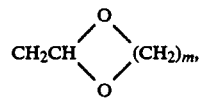

$(CH_2)_3OCH_3$, phenyl which may be optionally substituted with $R_7$,

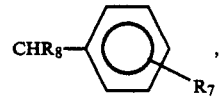

$CH_2C(O)CH_3$, CN, $OR_6$, $C_1$ to $C_6$ alkyl substituted with $OR_9$, $S(O)_nR_{10}$ or $NR_{11}R_{12}$, Q, $CHR_8Q$ or $CH_2CH_2Q$;
$R_3$ is $C_1$ to $C_6$ alkyl, $C_3$ to $C_6$ alkenyl, $C_3$ to $C_6$ alkynyl, $C_3$ to $C_6$ cycloalkyl which can be optionally substituted with 1 or 2 $CH_3$ groups, $C_4$ to $C_7$ cycloalkylalkyl, $C_5$ to $C_6$ cycloalkenyl, $C_1$ to $C_6$ haloalkyl, $C_1$ to $C_5$ alkoxy, $C_3$ to $C_6$ epoxyalkyl or $C_1$ to $C_6$ alkyl substituted with $OR_9$, $S(O)_nR_{10}$, $NR_{11}R_{12}$ or $P(O)(OR_5)_2$;
$R_4$ is $C_1$ to $C_3$ alkyl substituted with 1-3 atoms of F, Cl or Br, $C_3$ to $C_4$ alkynyl, $CH_2CH(OR_5)_2$,

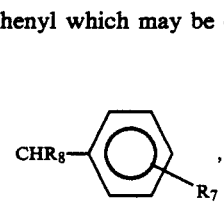

$C_2$ to $C_6$ haloalkenyl, $C_3$ to $C_6$ epoxyalkyl, $CH_2C(O)CH_3$, CN, $C_1$ to $C_6$ alkyl substituted with $OR_9$, $S(O)_nR_{10}$ or $NR_{11}R_{12}$, Q, $CHR_8Q$ or $CH_2CH_2Q$;
$R_3$ and $R_4$ can be taken together with the sulfonamide nitrogen to form a saturated 5- or 6-membered ring substituted by one or more groups selected from L or a partially saturated 5- or 6-membered ring optionally substituted by one or more groups selected from L;
$R_5$ is $C_1$ to $C_3$ alkyl;
$R_6$ is $C_1$ to $C_5$ alkyl;
$R_7$ is H, $C_1$ to $C_3$ alkyl, halogen, $NO_2$, $CF_3$, CN or $C_1$ to $C_3$ alkoxy;
$R_8$ is H or $CH_3$;
$R_9$ is H, $SO_2R_5$, $C(O)R_5$, $CO_2R_5$, $C(O)NR_{11}R_{12}$ or $P(O)(OR_5)_2$;
$R_{10}$ is $C_1$ to $C_3$ alkyl;
$R_{11}$ is H or $C_1$ to $C_3$ alkyl;
$R_{12}$ is H or $C_1$ to $C_3$ alkyl;
m is 2 or 3;
n is 0, 1 or 2;
Q is a saturated 5- or 6-membered ring which is bonded through a carbon atom and contains 1 heteroatom selected from oxygen, sulfur, or nitrogen or an unsaturated or partially unsaturated 5- or 6-membered ring which is bonded through a carbon atom and contains 1 to 3 hetero atoms selected from 1 sulfur, 1 oxygen or 1 to 3 nitrogen; and Q can be optionally substituted by one or more groups selected from L;
L is $C_1$ to $C_4$ alkyl, $C_1$ to $C_3$ haloalkyl, halogen, $C_1$ to $C_3$ alkoxy, $C_1$ to $C_3$ alkylthio, $C_3$ to $C_4$ alkenyloxy, $C_3$ to $C_4$ alkenylthio, $C_1$ to $C_2$ haloalkoxy or $C_1$ to $C_2$ haloalkylthio;

A is

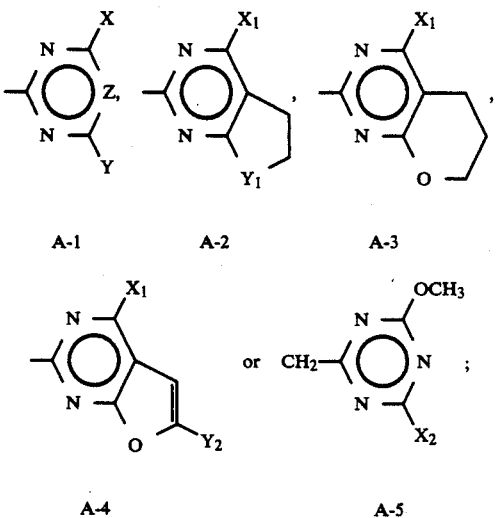

X is H, $C_1$ to $C_4$ alkyl, $C_1$ to $C_4$ alkoxy, $C_1$ to $C_4$ haloalkoxy, $C_1$ to $C_4$ haloalkyl, $C_1$ to $C_4$ haloalkylthio, $C_1$ to $C_4$ alkylthio, halogen, $C_2$ to $C_5$ alkoxyalkyl, $C_2$ to $C_5$ alkoxyalkoxy, amino, $C_1$ to $C_3$ alkylamino or di($C_1$ to $C_3$ alkyl)amino;

Y is H, $C_1$ to $C_4$ alkyl, $C_1$ to $C_4$ alkoxy, $C_1$ to $C_4$ haloalkoxy, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino, $C_3$ to $C_4$ alkenyloxy, $C_3$ to $C_4$ alkynyloxy, $C_2$ to $C_5$ alkylthioalkyl, $C_1$ to $C_4$ haloalkyl, $C_3$ to $C_5$ cycloalkyl, $C_2$ to $C_4$ alkynyl, $C(O)R_f$,

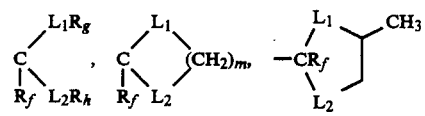

or $N(OCH_3)CH_3$;

$L_1$ and $L_2$ are independently O or S;
$R_f$ is H or $CH_3$;
$R_g$ and $R_h$ are independently $C_1$ to $C_2$ alkyl;
Z is CH or N;
$Y_1$ is O or $CH_2$;
$X_1$ is $CH_3$, $OCH_3$, $OC_2H_5$ or $OCF_2H$;
$Y_2$ is H or $CH_3$;
$X_2$ is $CH_3$ or $OCH_3$;
provided that:
(a) when X is Cl, F, Br or I, then Z is CH and Y is $OCH_3$, $OC_2H_5$, $N(OCH_3)CH_3$, $NHCH_3$ or $N(CH_3)_2$;
(b) when $R_2$ is $CH_2CF_3$ and A is A-1 then one or both of X and Y is $OCF_2H$;
(c) when $R_3$ or $R_4$ is $CH_2CF_3$, then the other is $CHF_2$, $CH_2CH_2F$, $CH_2CH_2Cl$, $CH_2CH_2Br$ or $CH_2CF_3$;
(d) when $R_4$ is $CF_2H$, then $R_3$ is other than $C_1$ to $C_3$ alkyl;
(e) when $R_4$ is $C_3$ to $C_4$ alkynyl, then $R_3$ is $CHF_2$, $CH_2CH_2F$, $CH_2CH_2Cl$, $CH_2CH_2Br$ or $C_3$ to $C_4$ alkynyl;
(f) when one or both of X and Y is $OCF_2H$, then $R_6$ is $C_3$ to $C_5$ alkyl;

(g) when $R_2$ is $OR_6$ and A is A-1 wherein Z is CH, then one or both of X and Y is other than $C_1$ to $C_4$ alkyl; and
(h) when X or Y is $OCF_2H$, then Z is CH.

In the preceding definitions, the term "alkyl", used either alone or in compound words such as "alkylthio" or "haloalkyl", denotes straight chain or branched alkyl, e.g., methyl, ethyl, n-propyl, isopropyl or the different butyl, pentyl and hexyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl, pentyl and hexenyl isomers.

Alkynyl denotes straight chain or branched alkynes, e.g., ethynyl, 1-propynyl, 2-propynyl and the different butynyl, pentyl and hexynyl isomers.

Cycloalkyl denotes cyclopropyl, cyclobutyl, cyclopentyl and cyclohexyl.

$C_4$ to $C_7$ cycloalkylalkyl means cyclopropylmethyl through cyclopropylbutyl or cyclohexylmethyl.

The term "halogen", either alone or in compound words such as "haloalkyl", denotes fluorine, chlorine, bromine or iodine. Further, when used in compound words such as "haloalkyl" said alkyl may be monohalogenated or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$ to $C_j$ prefix where i and j are numbers from 1 to 7. For example, $C_1$ to $C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; as a further example, $C_2$ cyanoalkyl would designate $CH_2CN$ and $C_3$ cyanoalkyl would designate $CH_2CH_2CN$ and $CH(CN)CH_3$.

Preferred compounds for reasons of increased ease of synthesis and/or greater herbicidal efficacy are:
(1) Compounds of Formula I wherein:
  W is O;
  J is J-1; and
  $R_2$ is $C_5$ to $C_6$ alkyl, $C_5$ to $C_6$ alkenyl, $C_2$ to $C_6$ haloalkenyl, $C_3$ to $C_6$ alkynyl, $C_3$ to $C_6$ cycloalkyl, $C_3$ to $C_6$ cycloalkyl optionally substituted with 1 or 2 $CH_3$ groups, $C_4$ to $C_7$ cycloalkylalkyl, $C_5$ to $C_6$ cycloalkenyl, $C_3$ to $C_6$ epoxyalkyl, $C_2$ to $C_6$ haloalkyl, $CH_2CH(OR_5)_2$, $(CH_2)_3OCH_3$, $OR_6$, phenyl which can be optionally substituted with $R_7$,

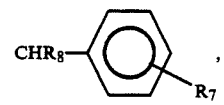

$CH_2C(O)CH_3$, CN or $C_1$ to $C_6$ alkyl substituted with $OR_9$, $S(O)_nR_{10}$ or $NR_{11}R_{12}$.
(2) Compounds of Formula I wherein:
  W is O;
  J is J-1; and
  $R_2$ is Q, $CHR_8Q$ or $CH_2CH_2Q$.
(3) Compounds of Formula I wherein:
  W is O;

J is J-2.

More preferred compounds (4) include those of (1) wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, Cl, F, Br, I, $CH_2F$, $OCF_2H$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

More preferred compounds (5) include those of (2) wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, Cl, F, Br, I, $CH_2F$, $OCF_2H$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

More preferred compounds (6) include those of (3) wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, Cl, F, Br, I, $CH_2F$, $OCF_2H$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

More preferred compounds (7) include those of (4) wherein:
$R_1$ is H, Cl, $OCH_3$, $OCF_2H$, $CH_2OCH_3$ or $CH_2CN$;
$R_2$ is $C_3$ to $C_4$ alkynyl, $C_3$ to $C_6$ cycloalkyl, $C_2$ to $C_4$ haloalkenyl, $CH_2CH_2F$, $CH_2CH_2Cl$ or $CH_2CH_2Br$;
X is $CH_3$, $OCH_3$, $OCH_2CH_3$, Cl, $OCF_2H$ or $OCH_2CF_3$; and
Y is $CH_3$, $OCH_3$, $CH_2CH_3$, $CH_2OCH_3$, $NHCH_3$ or $CH(OCH_3)_2$.

More preferred compounds (8) include those of (5) wherein:
$R_1$ is H, Cl, $OCH_3$, $OCF_2H$, $CH_2OCH_3$ or $CH_2CN$;
$R_2$ is Q or $CH_2Q$;
X is $CH_3$, $OCH_3$, $OCH_2CH_3$, Cl, $OCF_2H$ or $OCH_2CF_3$; and
Y is $CH_3$, $OCH_3$, $CH_2CH_3$, $CH_2OCH_3$, $NHCH_3$ or $CH(OCH_3)_2$.

More preferred compounds (9) include those of (6) wherein:
$R_1$ is H, Cl, $OCH_3$, $OCF_2H$, $CH_2OCH_3$ or $CH_2CN$;
$R_3$ is $C_1$ to $C_3$ alkyl, $C_3$ to $C_4$ alkenyl, $C_3$ to $C_4$ alkynyl, $C_3$ to $C_6$ cycloalkyl or $C_1$ to $C_2$ haloalkyl;
$R_4$ is $C_2$ to $C_4$ haloalkenyl or $C_3$ to $C_4$ epoxyalkyl;
X is $CH_3$, $OCH_3$, $OCH_2CH_3$, Cl, $OCF_2H$ or $OCH_2CF_3$; and
Y is $CH_3$, $OCH_3$, $CH_2CH_3$, $CH_2OCH_3$, $NHCH_3$ or $CH(OCH_3)_2$.

Specifically preferred for reasons of greatest ease of synthesis and/or greatest herbicidal efficacy are:
N-cyclopropyl-N'-[(4,6-dimethoxypyrimidin-2-yl)aminocarbonyl]-1,2-benzenedisulfonamide, m.p. 197.5° to 199° C.(d); and
N-cyclopropyl-N'-[(4-methoxy-6-methyl-1,3,5-triazin-2-yl)aminocarbonyl]-1,2-benzenedisulfonamide, m.p. 184.5° to 185.5° C.(d).

DETAILED DESCRIPTION OF THE INVENTION

Synthesis

Compounds of Formula I can be prepared by one or more of the procedures shown in Equations 1, 4, and 5. J, R, and A are as previously defined.

Equation 1

$$JSO_2N=C=W + \underset{\underset{R}{|}}{HNA} \longrightarrow I$$

$$\text{II} \qquad \text{III}$$

The reaction of Equation 1 is best carried out in an inert aprotic organic solvent such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent, to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonyl isocyanates (II, W is O) are known in the art and are prepared from the corresponding sulfonamides (IV) by one of the following two general methods.

Equation 2

$$JSO_2NH_2 \xrightarrow{\dfrac{CH_3(CH_2)_3NCO}{COCl_2, \text{ cat.}}} \text{II, W is O}$$

IV

The sulfonamide IV is reacted with an alkyl isocyanate (e.g., n-butyl isocyanate) in a solvent whose boiling point is above 135° C., such as xylene. The reaction can optionally be carried out in the presence of a catalytic amount of 1,4-diaza[2.2.2]-bicyclooctane (DABCO). The reaction mixture is heated to 135°–140° C. and held at that temperature for 5–60 minutes, after which phosgene is slowly added at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g., $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (IV) is high melting and has low solubility in the phosgenation solvent.

Sulfonyl isocyanates (II, W is O) can also be prepared by the following method.

Equation 3

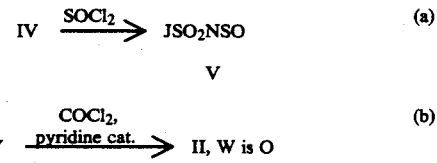

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140° C., with 80°-100° C. preferred. Conversion to the isocyanate (II, W is O) is usually substantially complete within 15 minutes to 3 hours (Equation 3b). The mixture is then cooled and filtered, and the solvent is evaporated, leaving the sulfonyl isocyanate (II, W is O).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Many of the compounds of Formula I can be prepared by the procedure shown in Equation 4.

Equation 4

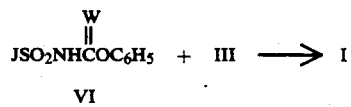

The reaction of Equation 4 is carried out by contacting phenylcarbamates or phenylthiocarbamates of Formula VI with aminoheterocycles of Formula III in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenylcarbamates and phenylthiocarbamates of Formula VI can be prepared by the methods described, or modifications thereof known to those skilled in the art, in U.S. Pat. No. 4,443,243.

Alternatively, many of the compounds of Formula I can be prepared by the method described in Equation 5.

Equation 5

The reaction of Equation 5 can be carried out by contacting equimolar amounts of a sulfonamide of Formula IV with a heterocyclic phenylcarbamate or phenylthiocarbamate of Formula VII in the presence of a base such as 1,8-diazabicyclo[5.4.0]undec-7-ene (DBU), by methods analogous to those described in South African Patent Application No. 83/0441. The phenylcarbamates and phenylthiocarbamates of Formula VII can be prepared by methods, or modifications thereof known to those skilled in the art, described in South African Patent Application No. 82/5671 and South African Patent Application No. 82/5045.

Sulfonamides of Formula IV can be prepared by one or more of the procedures shown in Equations 6a, 6b, 6c, and 6d.

Equations 6a and 6b illustrate the reaction of sulfonyl chlorides of Formula VIII with the appropriate primary and secondary amines to give sulfonamides of Formula IVa and IVb, respectively. Equations 6c and 6d illustrate the reaction of sulfonyl chlorides of Formulas IX and X with ammonia to give sulfonamides of Formulas IVa and IVb, respectively.

Equation 6

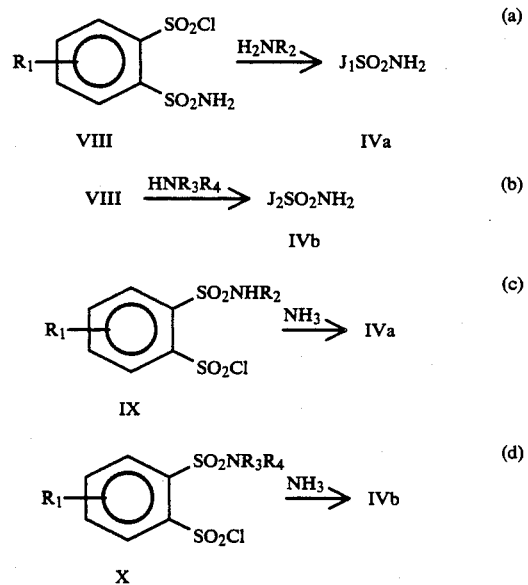

The reaction of Equations 6a, 6b, 6c, and 6d are best carried out in an inert aprotic solvent such as methylene chloride, tetrahydrofuran or acetonitrile at a temperature between −78° and 40° C. These reactions require the presence of a scavenger for the by-product hydrochloric acid. This may be accomplished by the use of a two-fold excess of the amine or by the addition of an equivalent of a base such as triethylamine, pyridine, or aqueous sodium hydroxide. In cases in which the products are insoluble in the reaction solvent, they may be isolated by simple filtration followed by washing with water to remove hydrochloride salts. When the products are soluble, they can be isolated by filtration to remove any insoluble salts, followed by evaporation of the solvent and trituration of the residue with solvents such as 1-chlorobutane, diethyl ether or ethyl acetate, and filtration. In some cases it is helpful to wash the product with water to remove residual salts.

Sulfonyl chlorides of Formula VIII where $R_1$ is as previously defined can be prepared by the methods shown in Equations 7 and 8.

Diazotization of appropriately substituted aniline derivatives of Formula XI, as shown in Equation 7, and subsequent coupling with sulfur dioxide in the presence of either cupric or cuprous chloride give the desired products of Formula VIII. This reaction can be accomplished by methods described, or modifications thereof, known to those skilled in the art, in the Journal of Pharmacy and Pharmacology, Vol. 12, pages 648 to 655 (1960).

Equation 7

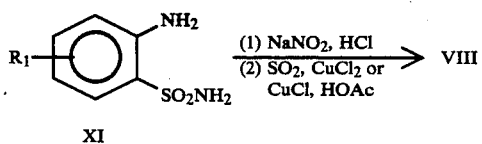

The reaction of Equation 7 can be accomplished by analogous methods described in U.S. Pat. No. 4,310,346. In Equation 7, a substituted aniline XI, wherein $R_1$ is not $NR_dR_e$, in concentrated hydrochloric acid is treated with a solution of sodium nitrite in water at −5° to 5° C. After being stirred for 10–30 minutes at about 0° C., the solution is added to a mixture of excess sulfur dioxide and a catalytic amount of cupric or cuprous chloride in acetic acid at about 10° C. After stirring for 0.25 to 24 hours at temperatures between 10° to 25° C., the solution is poured into a large excess of ice-water. The sulfonyl chlorides VIII can be isolated by filtration, or by extraction into a solvent such as methylene chloride or diethyl ether, followed by drying and evaporation of the solvent.

Oxidative chlorination of appropriately substituted arylthioethers of Formula XII give the desired products of Formula VIII wherein $R_{13}$ is $C_2$ to $C_4$ alkyl or benzyl and $R_1$ is not $C_1$ to $C_3$ alkylthio, $C_1$ to $C_3$ alkylsulfinyl, $C_1$ to $C_3$ haloalkylthio, $C_2$ to $C_3$ alkylthioalkyl or $C_2$ to $C_3$ haloalkylthioalkyl.

Equation 8

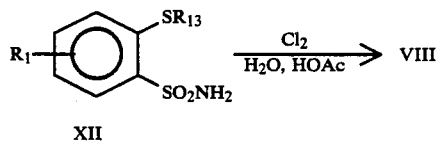

The reaction of Equation 8 can be carried out by treating a solution of the thioether XII in a solvent such as acetic acid in the presence of at least 2.5 equivalents of water and at least 3.0 equivalents of chlorine at 0°–30° C. for 0.25 to 5 hours. The reaction is poured into ice-water and the product is isolated by extraction with a suitable solvent such as methylene chloride, dried, and the solvent evaporated to yield a product sufficiently pure to be carried directly on to the next step.

Sulfonyl chlorides of Formula IX and X in Equations 6c and 6d are known in the art and can be prepared by analogous methods described in U.S. Pat. No. 4,310,346.

Aniline derivatives of Formula XI in Equation 7 can be prepared as shown in Equation 9 by reduction of the corresponding nitro compounds of Formula XIII where $R_1$ is other than $NO_2$.

Equation 9

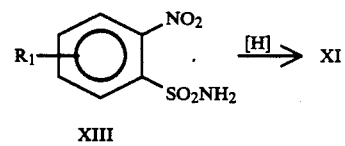

The reduction reactions of Equation 9 can be accomplished by methods known in the literature by those skilled in the art. For details see, for example, U.S. Pat. No. 4,511,392 and references cited therein.

The nitro compounds of Formula XIII are well known in the art and can be prepared by methods such as those described in U.S. Pat. No. 4,120,691.

The arylthioethers of Formula XII in Equation 8 are known in the art and can be prepared by methods described in U.S. Pat. No. 4,371,391.

The primary and secondary amines required for the reactions shown in Equations 6a and 6b, respectively, are known in the art or can be prepared by one skilled in the art using methods known in the literature.

In cases where the required secondary amine is not readily available, and $R_a$ and $R_b$ are other than H, it is more convenient to prepare sulfonamides of Formula IVb using the method of Equation 10.

Equation 10a illustrates the reaction of orthonitrobenzenesulfonyl chlorides of Formula XIV with primary amines to give secondary sulfonamides of Formula XV which can then be alkylated as shown in Equation 10b to give tertiary sulfonamides of Formula XVI. $R_1$, $R_3$, and $R_4$ are as previously defined and B is an appropriate displaceable substituent such as Cl, Br, I, $OSO_2CH_3$, $OSO_2CF_3$, $OSO_2C_6H_5$ or $OSO_2$-p-$CH_3C_6H_4$.

Equation 10

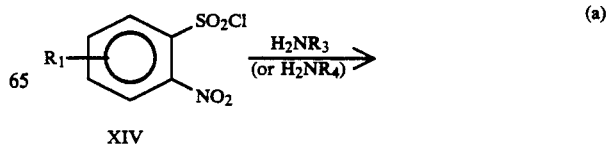

(a)

-continued

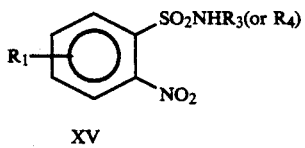

XV

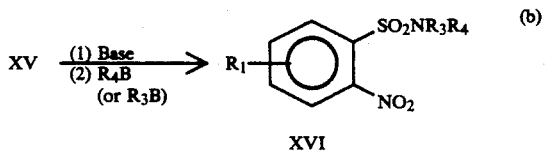

XVI

The reactions of Equation 10a can be carried out under the conditions described for the reactions of Equation 6. The reactions of Equation 10b are best carried out by the addition of a base such as triethylamine, DBU, or potassium carbonate to a solution of the secondary sulfonamide of Formula XV in an aprotic polar solvent such as acetonitrile or N,N-dimethylformamide at about −78° to 40° C. The alkylating agent is then added and after an additional one-half to 24 hours at about 0°–100° C. the reaction mixture is added to water to precipitate the product. Solid products can be isolated by simple filtration. If necessary, the products can be extracted with a solvent such as ethyl acetate or methylene chloride. The product is then isolated by drying and evaporation of the solvent and, when necessary, further purified by chromatography on silica gel.

Sulfonyl chlorides of Formula XIV are known in the art and can be prepared by methods described in U.S. Pat. No. 4,120,691. The nitro compounds of Formula XVI can be converted to sulfonamides of Formula IVb by the methods described in Equations 7 and 9.

When $R_1$ is other than $C_1$ to $C_3$ alkylthio, $C_1$ to $C_3$ alkylsulfinyl, $C_1$ to $C_3$ haloalkylthio, $C_2$ to $C_3$ alkylthioalkyl or $C_2$ to $C_3$ haloalkylthioalkyl, sulfonamides of Formula IVa wherein $R_2$ is $C_3$ to $C_6$ epoxyalkyl and sulfonamides of Formula IVb wherein either or both $R_3$ and $R_4$ are $C_3$ to $C_6$ epoxyalkyl can be conveniently prepared by contacting the corresponding alkenyl derivatives with an oxidizing agent such as hydrogen peroxide or meta-chloroperbenzoic acid using procedures which are well known in the art.

In cases where $R_2$, $R_3$, or $R_4$ is $C_1$ to $C_6$ alkyl substituted with $OSO_2R_5$, $OC(O)R_5$, $OCO_2R_5$, $OC(O)NR_{11}R_{12}$, or $OP(O)(OR_5)_2$ it is often more convenient to first prepare the corresponding sulfonamides of Formulas IVa and IVb or sulfonylureas of Formula I in which $R_2$, $R_3$, or $R_4$ is $C_1$ to $C_6$ alkyl substituted with OH. The hydroxy group can then be functionalized to give the desired derivatives using methods which are well known in the art.

When $R_1$ is other than $C_1$ to $C_3$ alkylthio, $C_1$ to $C_3$ alkylsulfinyl, $C_1$ to $C_3$ haloalkylthio, $C_2$ to $C_3$ alkylthioalkyl or $C_2$ to $C_3$ haloalkylthioalkyl and $R_2$, $R_3$, or $R_4$ is $C_1$ to $C_6$ alkyl substituted with $S(O)_nR_7$ and n is equal to 1 or 2, the sulfonamides (of Formulas IVa and IVb) or sulfonylureas (of Formula I) may also be prepared from the corresponding compounds in which n is equal to 0 by contact with an oxidizing agent such as hydrogen peroxide or meta-chloroperbenzoic acid. The level of oxidation may be controlled by the amount of oxidant used and by the reaction temperature according to procedures which are known in the art.

The heterocyclic amines of Formula III in Equations 1 and 4 above can be prepared by methods known in the literature, or simple modification thereof, by one skilled in the art.

For a review of the synthesis and reactions of 2-amino- and 2-methylaminopyrimidines III (A=A-1, Z=CH) see *The Chemistry of Heterocyclic Compounds*, Vol. 16, Wiley-Interscience, New York (1962). For a review of the synthesis and reactions 2-amino- and 2-methylamino-s-triazines III (A=A-1, Z=N) see *The Chemistry of Heterocyclic Compounds*, Vol. 13, Wiley-Interscience, New York (1959), F. C. Schaefer, U.S. Pat. No. 3,154,537 and F. C. Schaefer and K. R. Huffman *J. Org. Chem.*, 28, 1812 (1963).

EP-A No. 84,224 and W. Braker et al., *J. Chem. Soc.*, 69, 3072 (1947) describes methods for preparing aminopyridines and triazines substituted by acetal groups such as dialkoxymethyl or 1,3-dioxolan-2-yl.

South African Patent Application No. 83/7434 describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidines-2-amines (III, A is A-2) and the 6,7-dihydro-5H-pyrano[2.3-d]pyrimidin-2-amines (III, A is A-3) can be prepared as described in EP-A No. 15,683. The furo[2.3-d]pyrimidin-2-amines (III, A is A-4) are described in U.S. Pat. No. 4,487,626.

Compounds of Formula III, where A is A-5, are described in U.S. Pat. No. 4,496,392.

The amines of Formula III where A is A-6 can be prepared by methods taught in South African Patent Application No. 82/5045, or by suitable modifications that would be obvious to one skilled in the art.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

N-Cyclopropyl-1,2-benzenedisulfonamide

A solution of 1.28 g of 2-(aminosulfonyl)benzenesulfonyl chloride in 12 ml of dry THF was cooled to −65° C. and a solution of 0.80 ml of cyclopropylamine in 12 ml of dry THF added dropwise. The resulting mixture was allowed to warm to room temperature, filtered, and the filtrate concentrated in vacuo. The solid residue was partitioned between water and ethyl acetate, the organic phase was separated, washed with water, dried (MgSO$_4$), concentrated in vacuo, and the residue triturated with 1-chlorobutane to provide 1.15 g of N-cyclopropyl-1,2-benzenedisulfonamide as a white solid, m.p. 202°–203° C.

NMR(CDCl$_3$/DMSO-d$_6$)δ: 0.7 (br d, 4H, —CH$_2$CH$_2$—); 2.2 (m, 1H, CH of cyclopropane); 6.5 (br s, 1H, SO$_2$NH cyclopropyl); 7.0 (br s, 2H, SO$_2$NH$_2$); 7.7–7.9 (m, 2H, aromatics); and 8.2–8.4 (m, 2H, aromatics).

EXAMPLE 2

N-Cyclopropyl-N'-[(4,6-dimethoxypyrimidin-2-yl)aminocarbonyl]-1,2-benzenedisulfonamide To a solution of 0.14 g of the product of Example 1 and 0.15 g of phenyl(4,6-dimethoxypyrimidin-2-yl)carbamate in 2 ml of dry acetonitrile was added 0.1 ml of 1,5-diazabicyclo[5.4.0]undec-5-ene (DBU). The solution was stirred for 15 minutes at room temperature, diluted with 2 ml of water and acidified with 5% hydrochloric acid. The precipitated product was collected by filtration, washed successively with water, diethyl ether, and 1-chlorobutane, and dried in vacuo at 40° C. to afford 0.19 g of the subject compound, m.p. 197.5°–199° C. (dec.).

NMR(CDCl$_3$)δ: 0.6 (m, 4H, —CH$_2$CH$_2$—); 2.15 (m, 1H, CH of cyclopropane); 3.98 (s, 6H, OCH$_3$'s); 5.76 (s, 1H, pyr. C$_5$—H); 6.16 (br s, 1H, SO$_2$NH cyclopropyl); 7.19 (br s, 1H, —SO$_2$NHCONH—); 7.8 (m, 2H, aromatics); 8.26 (m, 1H, aromatic); 8.58 (m, 1H, aromatic); and 12.7 (br s, 1H, —SO$_2$NHCO—).

IR(nujol) 1705 cm$^{-1}$ (C=O).

Using the methods described herein, the compounds of Tables I through IV can be prepared.

General Structures for Tables I–IV

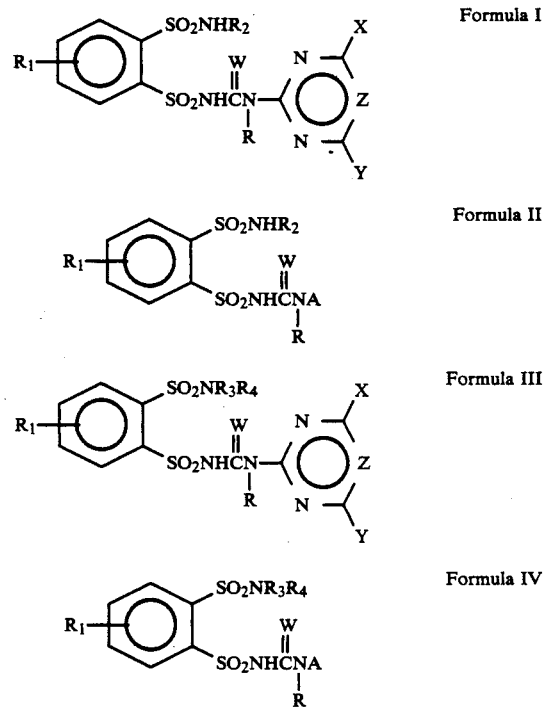

Formula I

Formula II

Formula III

Formula IV

TABLE I

Formula I, W = 0

| R | R$_1$ | R$_2$ | X | X | Z | m.p. (°C.) |
|---|---|---|---|---|---|---|
| H | H | n-C$_5$H | OCH$_3$ | CH$_3$ | N | |
| H | H | n-C$_5$H | OCH$_3$ | OCH$_3$ | CH | |
| H | H | n-C$_5$H | Cl | OCH$_3$ | CH | |
| H | H | CH$_2$CH$_2$CH(CH$_3$)$_2$ | CH$_3$ | OCH$_3$ | CH | |
| H | H | CH$_2$CH$_2$CH(CH$_3$)$_2$ | CH$_3$ | OC$_2$H$_5$ | CH | |
| H | H | CH$_2$CH$_2$CH(CH$_3$)$_2$ | OCH$_3$ | OCH$_3$ | N | |
| H | H | CH$_2$CH$_2$CH$_2$CH(CH$_3$)$_2$ | OCH$_3$ | CH$_3$ | N | |
| H | H | CH$_2$CH$_2$CH$_2$CH(CH$_3$)$_2$ | OCH$_3$ | CH$_3$ | CH | |
| H | H | CH$_2$CH$_2$CH$_2$(CH$_3$)$_2$ | OCH$_3$ | OCH$_3$ | CH | |
| H | H | CH(CH$_3$)CH$_2$CH$_2$CH$_3$ | OCH$_3$ | OCH$_3$ | CH | |
| H | H | CH(CH$_3$)CH$_2$CH$_/$ CH CH$_3$ | OCH$_3$ | OCH$_3$ | N | |
| H | H | CH(CH$_3$)CH$_2$CH$_2$CH$_3$ | CH$_3$ | OCH$_3$ | N | |
| H | H | CH$_2$CH$_2$CH$_2$CH=CH$_2$ | Cl | OC$_2$H$_5$ | CH | |
| H | H | CH$_2$CH$_2$CH$_2$CH=CH$_2$ | CH$_3$ | OCH$_3$ | N | |
| H | H | CH$_2$CH$_2$CH$_2$CH=CH$_2$ | CH$_3$ | OCH$_3$ | CH | |
| H | H | CH=CF$_2$ | OCH$_3$ | OCH$_3$ | CH | |
| H | H | CH=CF$_2$ | CH$_3$ | OCH$_3$ | N | |
| H | H | CH$_2$CCl=CHCl | CH$_3$ | OCH$_3$ | N | |
| H | H | CH$_2$CCl=CHCl | OCH$_3$ | OCH$_3$ | N | |
| H | H | CH$_2$CCl=CHCl | OCH$_3$ | OCH$_3$ | CH | |
| H | H | CH$_2$CCl=CHCl | Cl | OC$_2$H$_5$ | CH | |
| H | H | CH$_2$CH=CHCF$_3$ | CH$_3$ | CH$_3$ | CH | |
| H | H | CH$_2$CH=CHCF$_3$ | CH$_3$ | OCH$_3$ | N | |
| H | H | CH$_2$CH$_2$CH=CHCH$_2$CH 2Cl | CH$_3$ | OCH$_3$ | N | |
| H | H | CH$_2$CH$_2$CH=CHCH$_2$CH$_2$Cl | OCH$_3$ | OCH$_3$ | CH | |
| H | H | CH$_2$C≡CH | OCH$_3$ | OCH$_3$ | CH | 206–207(d) |
| H | H | CH$_2$C≡CH | Cl | OCH$_3$ | CH | 207.5–209(d) |
| H | H | CH$_2$CH$_2$C≡CH | CH$_3$ | OCH$_3$ | CH | 199–200(d) |
| H | H | CH$_2$C≡CH | CH$_3$ | CH$_3$ | | 201–203(d) |
| H | H | CH$_2$C≡CH | CH$_3$ | OCH$_3$ | N | 198–201(d) |

TABLE I-continued

Formula I, W = 0

| R | R$_1$ | R$_2$ | X | X | Z | m.p. (°C.) |
|---|---|---|---|---|---|---|
| H | H | CH$_2$C≡CH | CH$_3$ | CH$_3$ | N | 187-189(d) |
| H | H | CH$_2$C≡CH | OCH$_3$ | C≡CH | N | |
| H | H | CH$_2$C≡CH | Br | OCH$_3$ | CH | |
| H | H | CH$_2$C≡CH | Br | NHCH$_3$ | CH | |
| H | H | CH$_2$C≡CH | CH$_3$ | N(CH$_3$)$_2$ | CH | |
| H | H | CH$_2$C≡CH | OC$_2$H$_5$ | OCH$_3$ | CH | |
| H | H | CH$_2$C≡CH | OCH$_3$ | C$_2$H$_5$ | CH | |
| H | H | CH$_2$C≡CCH$_3$ | OCH$_3$ | CH$_3$ | N | |
| H | H | CH$_2$C≡CCH$_3$ | OCH$_3$ | OCH$_3$ | N | |
| H | H | CH$_2$C≡CCH$_3$ | OCH$_3$ | OCH$_3$ | CH | |
| H | H | CH$_2$C≡CCH$_3$ | CH$_3$ | H | CH | |
| H | H | CH$_2$CH$_2$CH$_2$C≡CH | OCH$_3$ | CH$_3$ | N | |
| H | H | CH$_2$CH$_2$CH$_2$C≡CH | OCH$_3$ | OCH$_3$ | CH | |
| H | H | CH$_2$CH$_2$C≡CCH$_2$CH$_3$ | OCH$_3$ | OCH$_3$ | CH | |
| H | H | CH$_2$CH$_2$C≡CCH$_2$CH$_3$ | CH$_3$ | OCH$_3$ | N | |
| H | H | cyclopropyl | H | H | CH | |
| H | H | cyclopropyl | CH$_3$ | H | CH | |
| H | H | cyclopropyl | CH$_2$CH$_2$CH$_2$CH$_3$ | CH$_3$ | CH | |
| H | H | cyclopropyl | CH$_2$CH$_2$CF$_3$ | CH$_3$ | CH | |
| H | H | cyclopropyl | CH$_2$CF$_3$ | CH$_3$ | CH | |
| H | H | cyclopropyl | CH$_2$CH$_2$Cl | CH$_3$ | CH | |
| H | H | cyclopropyl | CF$_3$ | CH$_3$ | CH | |
| H | H | cyclopropyl | CH$_2$Cl | CH$_3$ | CH | |
| H | H | cyclopropyl | CH$_2$Br | CH$_3$ | CH | |
| H | H | cyclopropyl | CH$_2$F | CH$_3$ | CH | |
| H | H | cyclopropyl | CH$_3$ | CH$_3$ | CH | 190-192(d) |
| H | H | cyclopropyl | OCH$_3$ | CH$_3$ | CH | 192-193.5(d) |
| H | H | cyclopropyl | OCH$_3$ | OCH$_3$ | CH | 197.5-199(d) |
| H | H | cyclopropyl | F | OCH$_3$ | CH | |
| H | H | cyclopropyl | Cl | OCH$_3$ | CH | 210-213(d) |
| H | H | cyclopropyl | Br | OCH$_3$ | CH | |
| H | H | cyclopropyl | I | OCH$_3$ | CH | |
| H | H | cyclopropyl | Cl | OC$_2$H$_5$ | CH | |
| H | H | cyclopropyl | Cl | N(OCH$_3$)CH$_3$ | CH | |
| H | H | cyclopropyl | Cl | NHCH$_3$ | CH | |
| H | H | cyclopropyl | Cl | N(CH$_3$)$_2$ | CH | |
| H | H | cyclopropyl | N(CH$_3$)$_2$ | N(CH$_3$)$_2$ | CH | |
| H | H | cyclopropyl | OC$_2$H$_5$ | CH$_3$ | CH | |
| H | H | cyclopropyl | On C$_4$H$_9$ | CH$_3$ | CH | |
| H | H | cyclopropyl | OCH$_2$CF$_3$ | CH$_3$ | CH | |
| H | H | cyclopropyl | OCH$_2$CH$_2$CH$_2$Cl | CH$_3$ | CH | |
| H | H | cyclopropyl | SCH$_3$ | CH$_3$ | CH | |
| H | H | cyclopropyl | SC$_2$H$_5$ | CH$_3$ | CH | |
| H | H | cyclopropyl | SCH$_3$ | OC$_2$H$_5$ | CH | |
| H | H | cyclopropyl | CH$_3$ | H | N | |
| H | H | cyclopropyl | CH$_3$ | CH$_3$ | N | |
| H | H | cyclopropyl | CH$_3$ | C≡CH | N | |
| H | H | cyclopropyl | CH$_3$ | C≡CCH$_3$ | N | |
| H | H | cyclopropyl | CH$_3$ | Cl | N | |
| H | H | cyclopropyl | CH$_3$ | CH$_2$CH$_2$Cl | N | |
| H | H | cyclopropyl | CH$_3$ | CH$_2$OCH$_3$ | N | |
| H | H | cyclopropyl | CH$_3$ | CH$_2$OC$_2$H$_5$ | N | |
| H | H | cyclopropyl | CH$_3$ | SCH$_3$ | N | |
| H | H | cyclopropyl | CH$_3$ | On C$_4$H$_9$ | N | |
| H | H | cyclopropyl | CH$_3$ | OCH$_3$CH=CH$_2$ | N | |
| H | H | cyclopropyl | CH$_3$ | OCH$_3$C≡CCH$_3$ | N | |
| H | H | cyclopropyl | CH$_3$ | CH$_2$SCH$_3$ | N | |
| H | H | cyclopropyl | CH$_3$ | CF$_3$ | CH | |
| H | H | cyclopropyl | CH$_3$ | OCH$_3$ | N | 184.5-185.5(d) |
| H | H | cyclopropyl | OCH$_3$ | OCH$_3$ | N | 190-192(d) |
| H | H | cyclopropyl | OCH$_3$ | cyclopropyl | CH | |
| H | H | cyclopropyl | OCH$_3$ | OCF$_3$ | CH | |
| H | H | cyclobutyl | OCH$_3$ | OCH$_3$ | CH | 195.5-197(d) |
| H | H | cyclobutyl | Cl | OCH$_3$ | CH | 214.5-217(d) |
| H | H | cyclobutyl | CH$_3$ | OCH$_3$ | CH | 191-192.5(d) |
| H | H | cyclobutyl | CH$_3$ | CH$_3$ | CH | 180-184(d) |
| H | H | cyclobutyl | CH$_3$ | N(C$_2$H$_5$)$_2$ | CH | |
| H | H | cyclobutyl | CH$_3$ | NHCH$_2$CH$_2$CH$_3$ | CH | |
| H | H | cyclobutyl | CH$_3$ | COCH$_3$ | CH | |
| H | H | cyclobutyl | CH$_3$ | CH(OCH$_3$)$_2$ | CH | |
| H | H | cyclobutyl | CH$_3$ | 1,3-dioxolan-2-yl | CH | |
| H | H | cyclobutyl | CH$_3$ | 1,3-oxathian-2-yl | CH | |
| H | H | cyclobutyl | NH$_2$ | CH$_3$ | N | |
| H | H | cyclobutyl | SCH$_2$CH$_2$Cl | CH$_3$ | N | |
| H | H | cyclobutyl | CH$_2$OC$_2$H$_7$ | CH$_3$ | N | |
| H | H | cyclobutyl | OC$_2$H$_5$OCH$_3$ | CH$_3$ | CH | |
| H | H | cyclobutyl | OCH$_3$ | CH$_3$ | N | 190-192(d) |
| H | H | cyclobutyl | OCH$_3$ | OCH$_3$ | N | 191-192.5(d) |
| H | H | cyclobutyl | CH$_3$ | CH$_3$ | N | |
| H | H | cyclobutyl | OCH$_3$ | C≡CH | N | |

TABLE I-continued

Formula I, W = 0

| R | R₁ | R₂ | X | X | Z | m.p. (°C.) |
|---|---|---|---|---|---|---|
| H | H | cyclobutyl | CH₃ | SCH₃ | N | |
| H | H | cyclopentyl | OCH₃ | CH₃ | CH | 182.5–183.5(d) |
| H | H | cyclopentyl | OCH₃OCH₃ | CH₃ | CH | |
| H | H | cyclopentyl | OCH₂CH₂OCH₃ | CH₃ | CH | |
| H | H | cyclopentyl | NH₂ | CH₃ | CH | |
| H | H | cyclopentyl | CH₃ | CH₃ | CH | 190–192(d) |
| H | H | cyclopentyl | OCH₃ | OCH₃ | CH | 187–188.5(d) |
| H | H | cyclopentyl | Cl | OCH₃ | CH | 214–215.5(d) |
| H | H | cyclopentyl | SCH₃ | OCH₃ | CH | |
| H | H | cyclopentyl | OCH₃ | OCH₃ | N | 193–195(d) |
| H | H | cyclopentyl | CH₃ | OCH₃ | N | 180–182(d) |
| H | H | cyclopentyl | CH₃ | CH₃ | N | |
| H | H | cyclopentyl | CH₃ | n-C₄H₉ | N | |
| H | H | cyclohexyl | CH₃ | CH₃ | N | |
| H | H | cyclohexyl | CH₃ | OCH₃ | N | |
| H | H | cyclohexyl | OCH₃ | OCH₃ | N | |
| H | H | cyclohexyl | OCH₃ | OCH₃ | CH | |
| H | H | cyclohexyl | Cl | OCH₃ | CH | |
| H | H | cyclohexyl | CH₃ | OCH₃ | CH | |
| H | H | cyclohexyl | CH₃ | CH₃ | CH | |
| H | H | 3-CH₃-cyclopentyl | OCH₃ | OCH₃ | CH | |
| H | H | 3-CH₃-cyclopentyl | OCH₃ | CH₃ | N | |
| H | H | 4-CH₃-cyclohexyl | OCH₃ | OCH₃ | CH | |
| H | H | 4-CH₃-cyclohexyl | CH₃ | OCH₃ | N | |
| H | H | CH₂-cyclopropyl | CH₃ | CH₃ | N | |
| H | H | CH₂-cyclopropyl | OCH₃ | CH₃ | N | 182–184 |
| H | H | CH₂-cyclopropyl | OCH₃ | OCH₃ | N | 184–186 |
| H | H | CH₂-cyclopropyl | OCH₃ | OCH₃ | CH | 171–173 |
| H | H | CH₂-cyclopropyl | CH₃ | OCH₃ | CH | 173–176 |
| H | H | CH₂-cyclopropyl | Cl | OCH₃ | CH | 207–209 |
| H | H | CH₂-cyclopropyl | CH₃ | CH₃ | CH | 186–188 |
| H | H | cyclohexen-1-yl | CH₃ | OCH₃ | N | |
| H | H | cyclohexen-1-yl | OCH₃ | OCH₃ | CH | |
| H | H | CH₂-oxirane | OCH₃ | OCH₃ | CH | 184–185(d) |
| H | H | CH₂-oxirane | Cl | OCH₃ | CH | |
| H | H | CH₂-oxirane | CH₃ | OCH₃ | CH | |
| H | H | CH₂-oxirane | CH₃ | CH₃ | N | |
| H | H | CH₂-oxirane | CH₃ | OCH₃ | N | |
| H | H | CH₂-oxirane | OCH₃ | OCH₃ | N | |
| H | H | CH₂-oxirane | OCH₃ | C≡CH | N | |
| H | H | CH₂CH₂F | OCH₃ | OCH₃ | N | 178–179.5(d) |
| H | H | CH₂CH₂F | CH₃ | OCH₃ | N | 192.5–194(d) |
| H | H | CH₂CH₂F | Cl | OCH₃ | CH | 205–208(d) |
| H | H | CH₂CH₂F | OCH₃ | OCH₃ | CH | 199.5–201(d) |
| H | H | CH₂CH₂Cl | OCH₃ | OCH₃ | CH | |
| H | H | CH₂CH₂Cl | OCH₃ | CH₃ | CH | |
| H | H | CH₂CH₂Cl | CH₃ | CH₃ | N | |
| H | H | CH₂CH₂Br | OCH₃ | CH₃ | N | |
| H | H | CH₂CH₂Br | OCH₃ | OCH₃ | CH | |
| H | H | CH₂CH(OCH₃)₂ | CH₃ | OCH₃ | N | 174–175(d) |
| H | H | CH₂CH(OCH₃)₂ | OCH₃ | OCH₃ | CH | 193.5–195(d) |
| H | H | CH₂CH(OC₂H₅)₂ | OCH₃ | CH₃ | N | |
| H | H | CH₂CH(OC₂H₅)₂ | OCH₃ | OCH₃ | CH | |
| H | H | CH₂-1,3-dioxan-2-yl | CH₃ | OCH₃ | N | |
| H | H | CH₂-1,3-dioxan-2-yl | OCH₃ | OCH₃ | CH | |
| H | H | CH₂CH₂CH₂OCH₃ | OCH₃ | CH₃ | N | |
| H | H | CH₂CH₂CH₂OCH₃ | OCH₃ | OCH₃ | CH | |
| H | H | OCH₃ | CH₃ | OCH₃ | N | 205–206(d) |
| H | H | OCH₃ | OCH₃ | OCH₃ | CH | 209–211(d) |
| H | H | C₆H₅ | OCH₃ | OCH₃ | CH | |
| H | H | C₅H₅ | CH₃ | OCH₃ | N | |
| H | H | 2-CH₃—C₆H₄ | OCH₃ | OCH₃ | CH | |
| H | H | 2-CH₃—C₆H₄ | OCH₃ | CH₃ | N | |
| H | H | 2-Cl—C₆H₄ | OCH₃ | CH₃ | N | |
| H | H | 2-Cl—C₆H₄ | OCH₃ | OCH₃ | CH | |
| H | H | 4-Br—C₆H₄ | CH₃ | OCH₃ | N | |
| H | H | 4-Br—C₆H₄ | OCH₃ | OCH₃ | CH | |
| H | H | 3-CF₃—C₆H₄ | OCH₃ | CH₃ | N | |
| H | H | 3-CF₃—C₆H₄ | OCH₃ | OCH₃ | CH | |
| H | H | 4-CH₃O—C₆H₄ | OCH₃ | CH₃ | N | |
| H | H | 4-CH₃O—C₆H₄ | OCH₃ | OCH₃ | CH | |
| H | H | CH₂C₆H₅ | OCH₃ | OCH₃ | CH | 198–199(d) |
| H | H | CH₂C₆H₅ | CH₃ | OCH₃ | CH | 180–182(d) |
| H | H | CH₂C₆H₅ | Cl | OCH₃ | CH | 168–170.5(d) |
| H | H | CH₂C₆H₅ | CH₃ | CH₃ | CH | 199–201(d) |

TABLE I-continued

Formula I, W = 0

| R | $R_1$ | $R_2$ | X | X | Z | m.p. (°C.) |
|---|---|---|---|---|---|---|
| H | H | $CH_2C_6H_5$ | $CH_3$ | $CH_3$ | N | |
| H | H | $CH_2C_6H_5$ | $OCH_3$ | $CH_3$ | N | 160.5–162.5(d) |
| H | H | $CH_2C_6H_5$ | $OCH_3$ | $OCH_3$ | N | 173–175(d) |
| H | H | $CH_2COCH_3$ | $OCH_3$ | $CH_3$ | N | |
| H | H | $CH_2COCH_3$ | $OCH_3$ | $OCH_3$ | CH | |
| H | H | CN | $OCH_3$ | $CH_3$ | N | |
| H | H | CN | $OCH_3$ | $OCH_3$ | CH | |
| H | H | $CH_2CH_2OH$ | $OCH_3$ | $CH_3$ | N | 175–178(d) |
| H | H | $CH_2CH_2OH$ | $OCH_3$ | $OCH_3$ | CH | 148–151(d) |
| H | H | $CH_2CH_2OC(O)CH_3$ | $CH_3$ | $OCH_3$ | N | |
| H | H | $CH_2CH_2OC(O)CH_3$ | $OCH_3$ | $OCH_3$ | CH | |
| H | H | $CH_2CH_2SO_2CH_3$ | $CH_3$ | $OCH_3$ | N | |
| H | H | $CH_2CH_2S_2OCH_3$ | $OCH_3$ | CH | | |
| H | H | $CH_2CH_2CO_2C_2H_5$ | $CH_3$ | $OCH_3$ | N | |
| H | H | $CH_2CH_2CO_2C_2H_5$ | $OCH_3$ | $OCH_3$ | CH | |
| H | H | $CH_2CH_2CH_2C(O)N(CH_3)_2$ | $CH_3$ | $OCH_3$ | N | |
| H | H | $CH_2CH_2CH_2C(O)N(CH_3)_2$ | $OCH_3$ | $OCH_3$ | CH | |
| H | H | $CH_2CH_2CH_2CH_2OP(O)(OCH_3)_2$ | $OCH_3$ | $CH_3$ | N | |
| H | H | $CH_2CH_2CH_2CH_2OP(O)(OCH_3)_2$ | $OCH_3$ | $OCH_3$ | CH | |
| H | H | $CH_2CH_2CH_2SCH_3$ | $OCH_3$ | $CH_3$ | N | |
| H | H | $CH_2CH_2CH_2SCH_3$ | $OCH_3$ | $OCH_3$ | CH | |
| H | H | $CH_2CH_2CH_2SO_2CH_3$ | $OCH_3$ | $CH_3$ | N | |
| H | H | $CH_2CH_2CH_2So_2CH_3$ | $OCH_3$ | $OCH_3$ | CH | |
| H | H | 1,3-dithiolan-2-yl | $CH_3$ | $OCH_3$ | N | |
| H | H | 1,3-dithiolan-2-yl | $OCH_3$ | $OCH_3$ | CH | |
| H | H | $CH_2$-tetrahydrofuran-2-yl | $OCH_3$ | $OCH_3$ | CH | |
| H | H | $CH_2$-tetrahydrofuran-2-yl | $CH_3$ | $OCH_3$ | N | |
| H | H | 4,6-dimethoxypyrimidin-2-yl | $CH_3$ | $OCH_3$ | CH | |
| H | H | 4-picolyl | $OCH_3$ | $OCH_3$ | CH | |
| H | 3-$CH_3$ | $\underline{n}$-$C_5H_{11}$ | $OCH_3$ | $OCH_3$ | CH | |
| H | 4-$CH_3$ | $\underline{n}$-$C_5H_{11}$ | $OCH_3$ | $OCH_3$ | CH | |
| H | 5-$C_2H_5$ | $\underline{n}$-$C_5H_{11}$ | $OCH_3$ | $OCH_3$ | CH | |
| H | 5-$CF_3$ | $CH_2$-cyclopropyl | $OCH_3$ | $OCH_3$ | CH | |
| H | 5-$CH_2CH_2Cl$ | $CH_2$-cyclopropyl | $OCH_3$ | $OCH_3$ | CH | |
| H | 5-Cl | $CH_2$-cyclopropyl | $OCH_3$ | $OCH_3$ | CH | |
| H | 5-Br | $CH_2$-cyclopropyl | $OCH_3$ | $OCH_3$ | CH | |
| H | 5-F | $CH_3$-cyclopropyl | $OCH_3$ | $OCH_3$ | CH | |
| H | 5-$NO_2$ | cyclobutyl | $OCH_3$ | $OCH_3$ | CH | |
| H | 5-$OCH_3$ | cyclobutyl | $OCH_3$ | $OCH_3$ | CH | |
| H | 5-$SO_2NHCH_3$ | cyclobutyl | $OCH_3$ | $OCH_3$ | CH | |
| H | 5-$SCH_3$ | cyclobutyl | $OCH_3$ | $OCH_3$ | CH | |
| H | 5-$SOC_2H_5$ | cyclobutyl | $OCH_3$ | $OCH_3$ | CH | |
| H | 5-$SO_2C_2H_5$ | $CH_2C_6H_5$ | $OCH_3$ | $OCH_3$ | CH | |
| H | 5-CN | $CH_2C_6H_5$ | $OCH_3$ | $OCH_3$ | CH | |
| H | 6-$CH_2CH_2CH_3$ | $CH_2C_6H_5$ | $OCH_3$ | $OCH_3$ | CH | |
| H | 6-$CH_2CF_3$ | $CH_2C_6H_5$ | $OCH_3$ | $OCH_3$ | CH | |
| H | 6-$CF_3$ | $CH_2C_6H_5$ | $OCH_3$ | $OCH_3$ | CH | |
| H | 6-$SCH_2F$ | $CH_2C_6H_5$ | $OCH_3$ | $OCH_3$ | CH | |
| H | 6-$OCH_2CF_3$ | $CH_2C_6H_5$ | $OCH_3$ | $OCH_3$ | CH | |
| H | 6-$CO_2CH_3$ | cyclopropyl | $OCH_3$ | $OCH_3$ | CH | |
| H | 6-$CO_2C_2H_5$ | cyclopropyl | $OCH_3$ | $OCH_3$ | CH | |
| H | 6-$CO_2CH_2CH=CH_2$ | cyclopropyl | $OCH_3$ | $OCH_3$ | CH | |
| H | 6-$CO_2CH_2CH_2CN$ | cyclopropyl | $OCH_3$ | $OCH_3$ | CH | |
| H | 6-$CO_2$-cyclohexyl | cyclopropyl | $OCH_3$ | $OCH_3$ | CH | |
| H | 6-$CH_2OCH_3$ | cyclopropyl | $OCH_3$ | $OCH_3$ | CH | |
| H | 6-Cl | cyclopropyl | $OCH_3$ | $OCH_3$ | CH | |
| H | 6-$SCH_3$ | cyclopropyl | $OCH_3$ | $OCH_3$ | CH | |
| H | 6-$SO_2CH_2CH_2CH_3$ | cyclopropyl | $OCH_3$ | $OCH_3$ | CH | |
| H | 6-$OCH_3$ | cyclopropyl | $OCH_3$ | $OCH_3$ | CH | |
| $CH_3$ | 6-$OCH_3$ | cyclopropyl | $OCH_3$ | $OCH_3$ | CH | |
| $CH_3$ | H | cyclopropyl | $OCH_3$ | $OCH_3$ | CH | |
| $CH_3$ | H | cyclopropyl | $CH_3$ | $OCH_3$ | N | |
| $CH_3$ | H | cyclopropyl | $OCH_3$ | $OCH_3$ | N | |
| $CH_3$ | H | $CH_2C\equiv CH$ | $OCH_3$ | $OCH_3$ | CH | |
| $CH_3$ | H | $CH_2C\equiv CH$ | $CH_3$ | $OCH_3$ | N | |
| $CH_3$ | H | $CH_2C\equiv CH$ | Cl | $OCH_3$ | CH | |
| $CH_3$ | H | $CH_2$-cyclobutyl | $OCH_3$ | $OCH_3$ | CH | |
| $CH_3$ | H | $CH_2$-cyclobutyl | $OCH_3$ | $CH_3$ | N | |
| $CH_3$ | H | $CH_2C_6H_5$ | $OCH_3$ | $CH_3$ | N | |
| $CH_3$ | H | $CH_2C_6H_5$ | $OCH_3$ | $OCH_3$ | CH | |
| $CH_3$ | H | $CH_2$-oxirane | $OCH_3$ | $CH_3$ | N | |
| $CH_3$ | H | $CH_2$-oxirane | $OCH_3$ | $OCH_3$ | CH | |

TABLE I-continued

Formula I, W = 0

| R | R₁ | R₂ | X | X | Z | m.p. (°C.) |
|---|---|---|---|---|---|---|
| CH₃ | H | 4-Cl—C₆H₄ | CH₃ | OCH₃ | N | |
| CH₃ | H | 4-Cl—C₆H₄ | OCH₃ | OCH₃ | CH | |
| H | H | CH₂CH₂F | CH₃ | CH₃ | CH | 188–190(d) |
| H | H | CH₂CH₂F | CH₃ | OCH₃ | CH | 192–193.5(d) |
| H | H | CH₂CH₂Cl | CH₃ | CH₃ | CH | |
| H | H | CH₂CH₂Cl | OCH₃ | CH | | |
| H | H | CH₂CH₂Cl | OCH₃ | OCH₃ | N | |
| H | H | CH₂CH₂Br | CH₃ | CH₃ | CH | |
| H | H | CH₂CH₂Br | CH₃ | OCH₃ | CH | |
| H | H | CH₂CH₂Br | Cl | OCH₃ | CH | |
| H | H | CH₂CH₂Br | OCH₃ | OCH₃ | N | |
| H | H | CH₂CH(OCH₃)₂ | CH₃ | CH₃ | CH | 185–186.5(d) |
| H | H | CH₂CH(OCH₃)₂ | CH₃ | OCH₃ | CH | 187–188.5(d) |
| H | H | CH₂CH(OCH₃)₂ | Cl | OCH₃ | CH | 180–182(d) |
| H | H | CH₂CH(OCH₃)₂ | OCH₃ | OCH₃ | N | 176–178(d) |
| H | H | CH₂COCH₃ | CH₃ | CH₃ | CH | |
| H | H | CH₂COCH₃ | CH₃ | OCH₃ | CH | |
| H | H | CH₂COCH₃ | Cl | OCH₃ | CH | |
| H | H | CH₂COCH₃ | OCH₃ | OCH₃ | N | |
| H | H | CN | CH₃ | CH₃ | CH | |
| H | H | CN | CH₃ | OCH₃ | CH | |
| H | H | CN | Cl | OCH₃ | CH | |
| H | H | CN | OCH₃ | OCH₃ | N | |
| H | H | CH₂CH₂OH | CH₃ | CH₃ | CH | 177–179(d) |
| H | H | CH₂CH₂OH | CH₃ | OCH₃ | CH | 163–165(d) |
| H | H | CH₂CH₂OH | Cl | OCH₃ | CH | 151–153(d) |
| H | H | CH₂CH₂OH | OCH₃ | OCH₃ | N | >250 |
| H | H | OCH₃ | CH₃ | CH₃ | CH | 212.5–213(d) |
| H | H | OCH₃ | CH₃ | OCH₃ | CH | 206–208(d) |
| H | H | OCH₃ | Cl | OCH₃ | CH | 225–227(d) |
| H | H | OCH₃ | OCH₃ | OCH₃ | N | 197–199(d) |
| H | H | Thiazol-2-yl | OCH₃ | OCH₃ | CH | |
| H | H | Thiazol-2-yl | CH₃ | OCH₃ | N | |
| H | H | 1,3,4-Thiadiazol-2-yl | OCH₃ | OCH₃ | CH | |
| H | H | 1,3,4-Thiadiazol-2-yl | CH₃ | OCH₃ | N | |
| H | H | 2-Picolyl | OCH₃ | OCH₃ | CH | |
| H | H | 2-Picolyl | CH₃ | OCH₃ | N | |
| H | H | 3-Picolyl | OCH₃ | OCH₃ | CH | |
| H | H | 3-Picolyl | CH₃ | OCH₃ | N | |
| H | H | 2-Pyridyl | OCH₃ | OCH₃ | CH | |
| H | H | 2-Pyridyl | CH₃ | OCH₃ | N | |
| H | H | 3-Pyridyl | OCH₃ | OCH₃ | CH | |
| H | H | 3-Pyridyl | CH₃ | OCH₃ | N | |
| H | H | 4-Pyridyl | OCH₃ | OCH₃ | CH | |
| H | H | 4-Pyridyl | CH₃ | OCH₃ | N | |
| H | H | CH₂CH₂-Pyridin-2-yl | OCH₃ | OCH₃ | CH | |
| H | H | CH₂CH₂-Pyridin-2-yl | CH₃ | OCH₃ | N | |
| H | H | CH₂-1-Methylpyrrolidin-2-yl | OCH₃ | OCH₃ | CH | |
| H | H | CH₂-1-Methylpyrrodidin-2-yl | CH₃ | OCH₃ | N | |
| H | H | CH₂CH₂-1-Methylpyrrol-2-yl | OCH₃ | OCH₃ | CH | |
| H | H | CH₂CH₂-1-Methylpyrrol-2-yl | CH₃ | OCH₃ | N | |
| H | 5-OCH₂CF₃ | cyclopropyl | CH₃ | CH₃ | CH | |
| H | 5-OCH₂CF₃ | cyclopropyl | CH₃ | OCH₃ | CH | |
| H | 5-OCH₂CF₃ | cyclopropyl | OCH₃ | OCH₃ | CH | |
| H | 5-OCH₂CF₃ | cyclopropyl | CH₃ | OCH₃ | N | |
| H | 5-OCH₂CF₃ | cyclopropyl | Cl | OCH₃ | CH | |
| H | 5-CH₂OCH₂CF₃ | cyclopropyl | OCH₃ | OCH₃ | CH | |
| H | 5-CH₂CN | cyclopropyl | OCH₃ | OCH₃ | CH | |
| H | 5-N(CH₃)₂ | cyclpropyl | OCH₃ | OCH₃ | CH | |
| H | H | CH₂-Pyridin-4-yl | CH₃ | CH₃ | CH | 177–179 |
| H | H | CH₂-Pyridin-4-yl | CH₃ | OCH₃ | CH | 172–174 |
| H | H | CH₂-Pyridin-4-yl | OCH₃ | OCH₃ | CH | 164–165 |
| H | H | CH₂-Pyridin-4-yl | CH₃ | OCH₃ | N | 177–178 |
| H | H | CH₂-Pyridin-4-yl | OCH₃ | OCH₃ | N | 174–177 |
| H | H | CH₂-Pyridin-4-yl | Cl | OCH₃ | CH | 180–181 |
| H | H | CH₂CH₂CH₂Br | CH₃ | CH₃ | CH | 160–162 |
| H | H | CH₂CH₂CH₂Br | CH₃ | OCH₃ | CH | 180–181 |
| H | H | CH₂CH₂CH₂Br | OCH₃ | OCH₃ | CH | 163–165 |
| H | H | CH₂CH₂CH₂Br | CH₃ | OCH₃ | N | 159–160 |
| H | H | CH₂CH₂CH₂Br | OCH₃ | OCH₃ | N | 170–172 |
| H | H | CH₂CH₂CH₂Br | Cl | OCH₃ | CH | 193–195 |
| H | H | CH₂CH₂CH₂Br | CH₃ | OCH₃ | CH | 132–134(d) |
| H | H | CH₂CH₂Cl | OCF₂H | CH₃ | CH | |
| H | H | CH₂CH₂Cl | OCF₂H | OCH₃ | CH | |
| H | H | CH₂CH₂Cl | OCF₂H | OCF₂HCH | | |
| H | H | cyclobutyl | OCF₂H | OCF₂H | CH | |
| H | H | cyclobutyl | OCF₂H | SCH₃ | CH | |

TABLE I-continued

Formula I, W = O

| R | R₁ | R₂ | X | X | Z | m.p. (°C.) |
|---|----|----|----|----|----|----|
| H | H | cyclobutyl | OCF₂H | N(CH₃)₂ | CH | |
| H | H | cyclobutyl | OCF₂H | C≡CH | CH | |
| H | H | cyclobutyl | OCF₂H | 1,3-dioxan-2-yl | CH | |
| H | H | CH₂CF₃ | OCF₂H | H | CH | |
| H | H | CH₂CF₃ | OCF₂H | C₂H₅ | CH | |
| H | H | CH₂CF₃ | OCF₂H | OCH₃ | CH | |
| H | H | CH₂C≡CH | OCF₂H | OCH₃ | CH | |
| H | H | CH₂C≡CH | OCF₂H | CH₃ | CH | |
| H | H | CH₂C≡CH | OCF₂H | CH₂OCH₃ | CH | |
| H | 5-OCH₃ | CH₂C≡CH | OCF₂H | CH₃ | CH | |
| H | 5-Br | CH₂C≡CH | OCF₂H | CH₃ | CH | |
| CH₃ | H | CH₂C≡CH | OCF₂H | CH₃ | CH | |

TABLE Ia

Formula I, W = S

| R | R₁ | R₂ | X | Y | Z | m.p.(°C.) |
|---|----|----|----|----|----|----|
| H | H | CH₂C≡CH | CH₃ | OCH₃ | N | |
| H | H | CH₂C≡CH | OCH₃ | OCH₃ | CH | |
| H | H | cyclopropyl | CH₃ | OCH₃ | CH | |
| H | H | cyclopropyl | OCH₃ | OCH₃ | CH | |
| H | H | CH₂CH₂F | OCH₃ | OCH₃ | CH | |
| H | H | CH₂CH₂F | CH₃ | OCH₃ | N | |
| H | H | CH₂CH₂Cl | Cl | OCH₃ | CH | |
| H | H | CH₂CH₂Cl | OCH₃ | OCH₃ | CH | |
| H | H | OCH₃ | CH₃ | OCH₃ | CH | |
| H | H | OCH₃ | OCH₃ | OCH₃ | CH | |
| H | H | OC₂H₅ | CH₃ | OCH₃ | N | |
| H | H | OC₂H₅ | OCH₃ | OCH₃ | CH | |
| H | H | CH₂-cyclopropyl | CH₃ | OCH₃ | CH | |
| H | H | CH₂-cyclopropyl | OCH₃ | OCH₃ | CH | |
| H | OCH₃ | CH₂CH₂F | OCH₃ | OCH₃ | CH | |

TABLE II

Formula II, W = O

| R | R₁ | R₂ | A | X₁ | X₂ | Y | Y₁ | Y₂ | m.p. (°C.) |
|---|----|----|----|----|----|----|----|----|----|
| H | H | n-C₆H₁₃ | A-2 | CH₃ | — | — | O | — | |
| H | H | n-C₆H₁₃ | A-2 | CH₃ | — | — | CH₂ | — | |
| H | H | n-C₆H₁₃ | A-2 | OCH₃ | — | — | CH₂ | — | |
| H | H | CH₂C≡CH | A-2 | OCH₃ | — | — | CH₂ | — | |
| H | H | CH₂C≡CH | A-2 | CH₃ | — | — | CH₂ | — | |
| H | H | CH₂C≡CH | A-2 | OCH₃ | — | — | O | — | |
| H | H | CH₂C≡CH | A-2 | CH₃ | — | — | O | — | |
| H | H | CH₂C≡CH | A-2 | OCF₂H | — | — | O | — | |
| H | H | cyclopropyl | A-2 | OCF₂H | — | — | CH₂ | — | |
| H | H | cyclopropyl | A-2 | OC₂H₅ | — | — | CH₂ | — | |
| H | H | cyclopropyl | A-2 | OCH₃ | — | — | CH₂ | — | |
| H | H | cyclopropyl | A-2 | CH₃ | — | — | CH₂ | — | |
| H | H | cyclopropyl | A-2 | CH₃ | — | — | O | — | |
| H | H | cyclopropyl | A-2 | OCH₃ | — | — | O | — | |
| H | H | cyclopropyl | A-2 | OC₂H₅ | — | — | O | — | |
| H | H | cyclopropyl | A-2 | OCF₂H | — | — | O | — | |
| H | H | cyclobutyl | A-2 | OCH₃ | — | — | CH₂ | — | |
| H | H | cyclobutyl | A-2 | OCH₃ | — | — | O | — | |
| H | H | cyclobutyl | A-2 | OCF₂H | — | — | O | — | |
| H | H | cyclobutyl | A-2 | CH₃ | — | — | CH₂ | — | |
| H | H | CH₂-cyclopropyl | A-2 | OCH₃ | — | — | CH₂ | — | |
| H | H | CH₂-cyclopropyl | A-2 | CH₃ | — | — | O | — | |
| H | H | CH₂-oxirane | A-2 | OCF₂H | — | — | CH₂ | — | |
| H | H | CH₂-oxirane | A-2 | OCH₃ | — | — | O | — | |
| H | H | CH₂CF₃ | A-2 | OCH₃ | — | — | O | — | |
| H | H | CH₂CF₃ | A-2 | CH₃ | — | — | O | — | |
| H | H | CH₂CF₃ | A-2 | OCF₂H | — | — | O | — | |
| H | H | CH₂CF₃ | A-2 | CH₃ | — | — | CH₂ | — | |
| H | H | CH₂CF₃ | A-2 | OCH₃ | — | — | CH₂ | — | |
| H | H | 2-BrC₆H₄ | A-2 | CH₃ | — | — | O | — | |
| H | H | 2-BrC₆H₄ | A-2 | OCH₃ | — | — | CH₂ | — | |
| H | 5-Cl | CH₂C₆H₅ | A-2 | OCF₂H | — | — | O | — | |
| H | 6-SO₂CH₃ | CH₂C₆H₅ | A-2 | CH₃ | — | — | CH₂ | — | |
| H | 5-Cl | cyclopropyl | A-2 | OCH₃ | — | — | O | — | |
| H | 6-Cl | cyclopropyl | A-2 | OCH₃ | — | — | CH₂ | — | |
| H | 5-OCH₃ | cyclopropyl | A-2 | CH₃ | — | — | O | — | |
| CH₃ | H | cyclopropyl | A-2 | OCH₃ | — | — | CH₂ | — | |
| H | H | n-C₅H₁₁ | A-3 | CH₃ | — | — | — | — | |
| H | H | CH₂C≡CH | A-3 | OCH₃ | — | — | — | — | |
| H | H | CH₂C≡CH | A-3 | CH₃ | — | — | — | — | |
| H | H | CH₂C₆H₅ | A-3 | OCH₃ | — | — | — | — | |
| H | H | CH₂C₆H₅ | A-3 | OCF₂H | — | — | — | — | |
| H | H | cyclopropyl | A-3 | OCF₂H | — | — | — | — | |
| H | H | cyclopropyl | A-3 | CH₃ | — | — | — | — | |
| H | H | CH₂-oxirane | A-3 | CH₃ | — | — | — | — | |
| H | H | CH₂-oxirane | A-3 | OC₂H₅ | — | — | — | — | |

TABLE II-continued

Formula II, W = O

| R | $R_1$ | $R_2$ | A | $X_1$ | $X_2$ | Y | $Y_1$ | $Y_2$ | m.p. (°C.) |
|---|---|---|---|---|---|---|---|---|---|
| H | H | $CH_2CF_3$ | A-3 | $OC_2H_5$ | — | — | — | — | |
| H | H | $CH_2CF_3$ | A-3 | $OCH_3$ | — | — | — | — | |
| H | H | $CH_2CF_3$ | A-3 | $OCF_2H$ | — | — | — | — | |
| H | H | $CH_2CF_3$ | A-3 | $CH_3$ | — | — | — | — | |
| H | H | $4\text{-}CH_3\text{—}C_6H_4$ | A-3 | $CH_3$ | — | — | — | — | |
| H | H | $4\text{-}CH_3\text{—}C_6H_4$ | A-3 | $OCH_3$ | — | — | — | — | |
| H | 5-$OCH_3$ | cyclobutyl | A-3 | $OCH_3$ | — | — | — | — | |
| H | 6-$OCH_3$ | cyclobutyl | A-3 | $OCH_3$ | — | — | — | — | |
| H | 6-Cl | cyclobutyl | A-3 | $CH_3$ | — | — | — | — | |
| H | 6-$SCH_3$ | cyclobutyl | A-3 | $CH_3$ | — | — | — | — | |
| $CH_3$ | H | cyclobutyl | A-3 | $OCH_3$ | — | — | — | — | |
| $CH_3$ | H | $CH_2$-cyclopropyl | A-3 | $OCF_2H$ | — | — | — | — | |
| H | H | $CH_2$-cyclopropyl | A-4 | $OCH_3$ | — | — | — | $CH_3$ | |
| H | H | $CH_2$-cyclopropyl | A-4 | $CH_3$ | — | — | — | H | |
| H | H | cyclopropyl | A-4 | $CH_3$ | — | — | — | $CH_3$ | |
| H | H | cyclopropyl | A-4 | $OCH_3$ | — | — | — | $CH_3$ | |
| H | H | cyclopropyl | A-4 | $OCH_3$ | — | — | — | H | |
| H | H | cyclopropyl | A-4 | $CH_3$ | — | — | — | H | |
| H | H | $CH_2CH_2CH=CH_2$ | A-4 | $CH_3$ | — | — | — | H | |
| H | H | $CH_2CH_2CH=CH_2$ | A-4 | $OCH_3$ | — | — | — | H | |
| H | H | $CH_2CF_3$ | A-4 | $CH_3$ | — | — | — | H | |
| H | H | $CH_2CF_3$ | A-4 | $OCH_3$ | — | — | — | $CH_3$ | |
| H | H | $CH_2C_6H_5$ | A-4 | $OCH_3$ | — | — | — | H | |
| H | 5-$CH_3$ | $CH_2C_6H_5$ | A-4 | $CH_3$ | — | — | — | H | |
| H | 5-$SCH_3$ | $CH_2C_6H_5$ | A-4 | $OCH_3$ | — | — | — | $CH_3$ | |
| H | 6-$OCH_3$ | $CH_2C_6H_5$ | A-4 | $CH_3$ | — | — | — | $CH_3$ | |
| $CH_3$ | H | $CH_2C_6H_5$ | A-4 | $OCH_3$ | — | — | — | H | |
| $CH_3$ | H | $CH_2C\equiv CH$ | A-4 | $OCH_3$ | — | — | — | H | |
| H | H | $CH_2CF_3$ | A-5 | — | $CH_3$ | — | — | — | |
| H | H | $CH_2CF_3$ | A-5 | — | $OCH_3$ | — | — | — | |
| H | H | cyclopropyl | A-5 | — | $CH_3$ | — | — | — | |
| H | H | cyclopropyl | A-5 | — | $OCH_3$ | — | — | — | |
| H | H | $CH_2C_6H_5$ | A-5 | — | $OCH_3$ | — | — | — | |
| H | 5-$CH_3O$ | $CH_2C_6H_5$ | A-5 | — | $OCH_3$ | — | — | — | |
| $CH_3$ | H | $\underline{n}\text{-}C_5H_{11}$ | A-5 | — | $OCH_3$ | — | — | — | |

TABLE IIa

Formula II, W = S

| R | $R_1$ | $R_2$ | A | $X_1$ | $X_2$ | Y | $Y_1$ | $Y_2$ | m.p. (°C.) |
|---|---|---|---|---|---|---|---|---|---|
| H | H | $CH_2C\equiv CH$ | A-2 | $OCH_3$ | — | — | O | — | |
| H | H | $CH_2CH_2F$ | A-2 | $OCH_3$ | — | — | $CH_2$ | — | |
| H | H | cyclopropyl | A-3 | $CH_3$ | — | — | — | — | |
| H | H | $CH_2CH_2F$ | A-3 | $OCH_3$ | — | — | — | — | |
| H | H | $CH_2CH_2Cl$ | A-4 | $CH_3$ | — | — | — | $CH_3$ | |
| H | H | $CH_2C\equiv CH$ | A-4 | $OCH_3$ | — | — | — | H | |
| H | H | $CH_2$-cyclopropyl | A-5 | — | $OCH_3$ | — | — | — | |
| H | H | $CH_2CH_2F$ | A-5 | — | $OCH_3$ | — | — | — | |

TABLE III

Formula III, W = O

| R | $R_1$ | $R_3$ | $R_4$ | X | Y | Z | m.p. (°C.) |
|---|---|---|---|---|---|---|---|
| H | H | $CH_3$ | $CH_2CH_2F$ | $OCH_3$ | $OCH_3$ | CH | |
| H | H | $CH_3$ | $CH_2CH_2F$ | $OCH_3$ | $CH_3$ | CH | |
| H | H | $CH_3$ | $CH_2CH_2F$ | $CH_3$ | $CH_3$ | CH | |
| H | H | $CH_3$ | $CH_2CH_2F$ | $CF_3$ | $CH_3$ | CH | |
| H | H | $CH_3$ | $CH_2CH_2F$ | Cl | $OCH_3$ | CH | |
| H | H | $CH_3$ | $CH_2CH_2F$ | $OCH_3$ | $OCH_3$ | N | |
| H | H | $CH_3$ | $CH_2CH_2F$ | $OCH_3$ | $CH_3$ | N | |
| H | H | $CH_3$ | $CH_2CH_2F$ | $CH_3$ | $CH_3$ | N | |
| H | H | $CH_3$ | $CH_2CH_2Cl$ | $OCH_3$ | $CH_3$ | N | |
| H | H | $CH_3$ | $CH_2CH_2Cl$ | $OCH_3$ | $OCH_3$ | N | |
| H | H | $CH_3$ | $CH_2CH_2Cl$ | $OCH_3$ | $OCH_3$ | CH | |
| H | H | $CH_3$ | $CH_2CH_2Cl$ | Cl | $OCH_3$ | CH | |
| H | H | $CH_3$ | $CH_2CH_2Cl$ | $CH_3$ | $OCH_3$ | CH | |
| H | H | $CH_3$ | $CH_2CH_2Cl$ | $CH_3$ | $CH_3$ | CH | |
| H | H | $CH_3$ | $CH_2CH_2Br$ | $OCH_3$ | $CH_3$ | N | |
| H | H | $CH_3$ | $CH_2CH_2Br$ | $OCH_3$ | $OCH_3$ | N | |
| H | H | $CH_3$ | $CH_2CH_2Br$ | Cl | $OCH_3$ | CH | |
| H | H | $CH_3$ | $CH_2CH_2Br$ | $OCH_3$ | $OCH_3$ | CH | |
| H | H | $CH_3$ | $CH_2CH_2Br$ | $CH_3$ | $CH_3$ | CH | |
| H | H | $CH_3$ | $CH_2CH_2Br$ | $OCH_3$ | $CH_3$ | CH | |
| H | H | $CH_3$ | $CH_2CH_2CH_2F$ | $OCH_3$ | $OCH_3$ | CH | |

TABLE III-continued

Formula III, W = O

| R | R$_1$ | R$_3$ | R$_4$ | X | Y | Z | m.p. (°C.) |
|---|---|---|---|---|---|---|---|
| H | H | CH$_3$ | CH$_2$CH$_2$CH$_2$F | CH$_3$ | OCH$_3$ | N | |
| H | H | CH$_3$ | CH$_2$CH(OC$_2$H$_5$)$_2$ | CH$_3$ | CH$_3$ | CH | |
| H | H | CH$_3$ | CH$_2$CH(OC$_2$H$_5$)$_2$ | CH$_3$ | OCH$_3$ | N | |
| H | H | CH$_3$ | CH$_2$-1,3-dioxan-2-yl | CH$_3$ | OCH$_3$ | N | |
| H | H | CH$_3$ | CH$_2$-1,3-dioxan-2-yl | OCH$_3$ | OCH$_3$ | CH | |
| H | H | CH$_3$ | CH$_2$CH=CH—CF$_3$ | OCH$_3$ | CH$_3$ | CH | |
| H | H | CH$_3$ | CH$_2$CH=CH—CF$_3$ | OCH$_3$ | CH$_3$ | N | |
| H | H | CH$_3$ | CH$_2$-oxirane | OCH$_3$ | OHC$_3$ | N | |
| H | H | CH$_3$ | CH$_2$-oxirane | CH$_3$ | OCH$_3$ | CH | |
| H | H | CH$_3$ | CH$_2$-oxirane | OCH$_3$ | OCH$_3$ | CH | |
| H | H | CH$_3$ | CH$_2$-oxirane | Cl | OCH$_3$ | CH | |
| H | H | CH$_3$ | CH$_2$-oxirane | CH$_3$ | CH$_3$ | CH | |
| H | H | CH$_3$ | CH$_2$-oxirane | OCH$_3$ | CH$_3$ | N | |
| H | H | CH$_3$ | CH$_2$C(O)CH$_3$ | OCH$_3$ | OCH$_3$ | CH | |
| H | H | CH$_3$ | CH$_2$CH$_2$CH$_2$OC(O)CH$_2$CH$_3$ | OCH$_3$ | OCH$_3$ | CH | |
| H | H | CH$_3$ | CH$_2$CH$_2$OSO$_2$CH$_3$ | OCH$_3$ | OCH$_3$ | CH | |
| H | H | CH$_3$ | CH$_2$CH$_2$SCH$_3$ | OCH$_3$ | OCH$_3$ | CH | |
| H | H | CH$_3$ | CH$_2$CH$_2$CH$_2$N(CH$_3$)$_2$ | OCH$_3$ | OCH$_3$ | CH | |
| H | H | CH$_3$ | 4-picolyl | OCH$_3$ | OCH$_3$ | CH | |
| H | H | C$_2$H$_5$ | CH$_2$CH$_2$CH$_2$Cl | OCH$_3$ | CH$_3$ | N | |
| H | H | n-C$_5$H$_{11}$ | CH$_2$CH$_2$CH$_2$Cl | OCH$_3$ | CH$_3$ | N | |
| H | H | CH$_2$CH=CHCH$_3$ | CHF$_2$ | OCH$_3$ | CH$_3$ | N | |
| H | H | cyclopropyl | CHF$_2$ | OCH$_3$ | CH$_3$ | N | |
| H | H | cyclopropyl | CHF$_2$ | OCH$_3$ | CH$_3$ | N | |
| H | H | 4-CH$_3$-cyclohexyl | CHF$_2$ | OCH$_3$ | CH$_3$ | N | |
| H | H | CH$_2$-cyclobutyl | CH$_2$CH$_2$Br | OCH$_3$ | CH$_3$ | N | |
| H | H | 1-cyclohexen-1-yl | CH$_2$CH$_2$Br | OCH$_3$ | CH$_3$ | N | |
| H | H | CH$_2$CH$_2$Cl | CH$_2$CH$_2$Br | OCH$_3$ | CH$_3$ | N | |
| H | H | CH$_2$CH$_2$Cl | CH$_2$CH$_2$Br | OCH$_3$ | OCH$_3$ | CH | |
| H | H | CH$_2$CH$_2$CH$_2$CH$_2$Br | CH$_2$CH$_2$Br | CH$_3$ | OCH$_3$ | N | |
| H | H | CH$_2$CH$_2$CH$_2$CH$_2$Br | OCH$_3$ | OCH$_3$ | CH | | |
| H | H | CH$_2$CF$_3$ | CHF$_2$ | OCH$_3$ | OCH$_3$ | CH | |
| H | H | CH$_2$CF$_3$ | CH$_2$CH$_3$F | OCH$_3$ | OCH$_3$ | CH | |
| H | H | CH$_2$CF$_3$ | CH$_2$CH$_2$F | CH$_3$ | OCH$_3$ | N | |
| H | H | CH$_2$CF$_3$ | CH$_2$CF$_3$ | OCH$_3$ | OCH$_3$ | CH | |
| H | H | CH$_2$CF$_3$ | CH$_2$CF$_3$ | OCH$_3$ | CH$_3$ | N | |
| H | H | CH$_2$CF$_3$ | CH$_2$CH$_2$Br | OCH$_3$ | OCH$_3$ | CH | |
| H | H | CH$_2$CF$_3$ | CH$_2$CH$_2$Br | CH$_3$ | OCH$_3$ | N | |
| H | H | OCH$_2$CH$_3$ | CH$_2$CH$_2$Br | OCH$_3$ | OCH$_3$ | N | |
| H | H | OCH$_2$CH$_3$ | CH$_2$CH$_2$Br | OCH$_3$ | OCH$_3$ | CH | |
| H | H | OCH$_2$CH$_2$CH$_2$CH$_3$ | CH$_2$CH$_2$Br | Cl | OCH$_3$ | CH | |
| H | H | OCH$_2$CH$_2$CH$_2$CH$_3$ | CH$_2$CH$_2$Br | CH$_3$ | OCH$_3$ | N | |
| H | H | CH$_2$-oxirane | CH$_2$CH$_2$Br | CH$_3$ | OCH$_3$ | N | |
| H | H | CH$_2$-oxirane | CH$_2$CH$_2$Br | OC$_2$H$_5$ | OCH$_3$ | CH | |
| H | H | CH$_2$CH$_2$OC(O)N(CH$_3$)$_2$ | CH$_2$CH$_2$Br | OCH$_3$ | C≡CH | N | |
| H | H | CH$_2$CH$_2$OC(O)N(CH$_3$)$_2$ | CH$_2$CH$_2$Br | Br | OCH$_3$ | CH | |
| H | H | CH$_2$CH$_2$SOCH$_3$ | CH$_2$CH$_2$Br | CF$_3$ | CF$_3$ | CH | |
| H | H | CH$_2$CH$_2$SOCH$_3$ | CH$_2$CH$_2$Br | OCH$_3$ | OCH$_3$ | N | |
| H | H | CH$_2$CH$_2$CH$_2$N(C$_2$H$_5$)$_2$ | CH$_2$CH$_2$Br | OCH$_3$ | OCH$_3$ | CH | |
| H | H | CH$_2$CH$_2$CH$_2$N(C$_2$H$_5$)$_2$ | CH$_2$CH$_2$Br | CH$_3$ | OCH$_3$ | N | |
| H | H | CF$_2$H | CH$_2$C≡CH | OCH$_3$ | OCH$_3$ | CH | |
| H | H | CH$_2$CH$_2$F | CH$_2$C≡CH | OCH$_3$ | OCH$_3$ | CH | |
| H | H | CH$_2$CH$_2$F | CH$_2$C≡CH | CH$_3$ | OCH$_3$ | N | |
| H- | H | CH$_2$CH$_2$Br | CH$_2$C≡CH | OCH$_3$ | OCH$_3$ | CH | |
| H | H | CH$_2$CH$_2$Br | CH$_2$C≡CH | CH$_3$ | OCH$_3$ | N | |
| H | H | CH$_2$C≡CH | CH$_2$C≡CH | OCH$_3$ | OCH$_3$ | CH | |
| H | H | CH$_2$C≡CH | CH$_2$C≡CH | Cl | OCH$_3$ | CH | |
| H | H | CH$_2$C≡CH | CH$_2$C≡CH | CH$_3$ | OCH$_3$ | CH | |
| H | H | CH$_2$C≡CH | CH$_2$C≡CH | CH$_3$ | CH$_3$ | CH | |
| H | H | CH$_2$C≡CH | CH$_2$C≡CH | CH$_3$ | CH$_3$ | N | |
| H | H | CH$_2$C≡CH | CH$_2$C≡CH | CH$_3$ | OCH$_3$ | N | |
| H | H | CH$_2$C≡CH | CH$_2$C≡CH | OCH$_3$ | OCH$_3$ | N | |
| H | H | CH$_3$ | CN | OCH$_3$ | OCH$_3$ | N | |
| H | H | CH$_3$ | CN | OCH$_3$ | CH$_3$ | N | |
| H | H | CH$_3$ | CN | CH$_3$ | CH$_3$ | CH | |
| H | H | CH$_3$ | CN | CH$_3$ | OCH$_3$ | CH | |
| H | H | CH$_3$ | CN | Cl | OCH$_3$ | CH | |
| H | H | CH$_3$ | CN | OCH$_3$ | OCH$_3$ | CH | |
| H | 4-Cl | CH$_3$ | CH$_2$CH$_2$F | OCH$_3$ | OCH$_3$ | CH | |
| H | 5-Cl | CH$_3$ | CH$_2$CH$_2$F | OCH$_3$ | OCH$_3$ | CH | |
| H | 6-Cl | CH$_3$ | CH$_2$CH$_2$F | OCH$_3$ | OCH$_3$ | CH | |
| H | 5-OCH$_3$ | CH$_3$ | CH$_2$CH$_2$F | OCH$_3$ | OCH$_3$ | CH | |
| H | 6-OCH$_3$ | CH$_3$ | CH$_2$CH$_2$F | OCH$_3$ | OCH$_3$ | CH | |
| H | 6-SCH$_3$ | CH$_3$ | CH$_2$CH$_2$F | OCH$_3$ | OCH$_3$ | CH | |
| H | 6-SO$_2$CH$_3$ | CH$_3$ | CH$_2$CH$_2$F | OCH$_3$ | OCH$_3$ | CH | |
| H | 6-SO$_2$CH$_2$CH$_2$CH$_3$ | CH$_3$ | CH$_2$CH$_2$F | OCH$_3$ | OCH$_3$ | CH | |
| H | 6-CH$_3$ | CH$_3$ | CH$_2$CH$_2$F | OCH$_3$ | OCH$_3$ | CH | |
| H | 6-SO$_2$NHCH$_3$ | CH$_3$ | CH$_2$CH$_2$F | OCH$_3$ | OCH$_3$ | CH | |
| H | 5-CN | CH$_3$ | CH$_2$CH$_2$F | OCH$_3$ | OCH$_3$ | CH | |
| CH$_3$ | H | CH$_3$ | CH$_2$CH$_2$F | OCH$_3$ | OCH$_3$ | CH | |

TABLE III-continued

Formula III, W = 0

| R | $R_1$ | $R_3$ | $R_4$ | X | Y | Z | m.p. (°C.) |
|---|---|---|---|---|---|---|---|
| $CH_3$ | H | $CH_3$ | $CH_2CH_2Cl$ | $OCH_3$ | $OCH_3$ | CH | |
| $CH_3$ | H | $CH_3$ | $CH_2$-oxirane | $OCH_3$ | $OCH_3$ | CH | |
| $CH_3$ | H | $CH_2C\equiv CH$ | $CH_2C\equiv CH$ | $OCH_3$ | $OCH_3$ | CH | |
| $CH_3$ | H | $CH_2CF_3$ | $CH_2CF_3$ | $OCH_3$ | $OCH_3$ | CH | |
| H | H | $CH_3$ | 2-Pyridyl | $OCH_3$ | $OCH_3$ | CH | |
| H | H | $CH_3$ | 2-Pyridyl | $CH_3$ | $OCH_3$ | N | |
| H | H | $CH_3$ | $CH_2CH_2$—Pyridin-2-yl | $OCH_3$ | $OCH_3$ | CH | |
| H | H | $CH_3$ | $CH_2CH_2$—Pyridin-2-yl | $CH_3$ | $OCH_3$ | N | |
| H | H | $CH_3$ | Thiazol-2-yl | $OCH_3$ | $OCH_3$ | CH | |
| H | H | $CH_3$ | Thiazol-2-yl | $CH_3$ | $OCH_3$ | N | |
| H | H | | —$CH_2CH_2CH_2CH(CH_3)CH_2$— | $CH_3$ | $OCH_3$ | CH | |
| H | H | | —$CH_2CH_2CH_2CH(CH_3)CH_2$— | $CH_3$ | $OCH_3$ | N | |
| H | H | | —$CH_2CH_2CH_2CH(CH_3)CH_2$— | $OCH_3$ | $OCH_3$ | CH | |
| H | H | | —$CH_2CH(Cl)CH(Cl)CH_2$— | $CH_3$ | $CH_3$ | CH | |
| H | H | | —$CH_2CH(Cl)CH(Cl)CH_2$— | $CH_3$ | $OCH_3$ | CH | |
| H | H | | —$CH_2CH(Cl)CH(Cl)CH_2$— | $OCH_3$ | $OCH_3$ | N | |
| H | H | | —$CH_2CH(Cl)CH(Cl)CH_2$— | Cl | $OCH_3$ | CH | |
| H | H | | —$CH_2CH=CHCH_2$— | Cl | $OCH_3$ | CH | 210–217(d) |
| H | H | | —$CH_2CH=CHCH_2$— | $CH_3$ | $OCH_3$ | CH | |
| H | H | | —$CH_2CH=CHCH_2$— | $OCH_3$ | $OCH_3$ | CH | 220–230(d) |
| H | H | | —$CH_2CH=CHCH_2$— | $CH_3$ | $OCH_2CH_2CH_3$ | CH | 193–196(d) |
| H | H | | —$CH_2CH=CHCH_2$— | $CH_3$ | $OCH(CH_3)_2$ | CH | 173–179(d) |
| H | H | | —$CH_2CH(Br)CH(Br)CH_2$— | $CH_3$ | $OCH_3$ | CH | |
| H | H | | —$CH_2CH(Br)CH(Br)CH_2$— | $OCH_3$ | $OCH_3$ | CH | |
| H | 3-$CH_3$ | $CH_3$ | $CH_2CH_2F$ | $CH_3$ | $CH_3$ | CH | 175–176 |
| H | 3-$CH_3$ | $CH_3$ | $CH_2CH_2F$ | $CH_3$ | $OCH_3$ | CH | 170–171 |
| H | 3-$CH_3$ | $CH_3$ | $CH_2CH_2F$ | $OCH_3$ | $OCH_3$ | CH | 212–214 |
| H | 3-$CH_3$ | $CH_3$ | $CH_2CH_2F$ | Cl | $OCH_3$ | CH | 172–173 |
| H | 3-$CH_3$ | $CH_3$ | $CH_2CH_2F$ | $CH_3$ | $OCH_3$ | N | 177–178 |
| H | 3-$CH_3$ | $CH_3$ | $CH_2CH_2F$ | $OCH_3$ | $OCH_3$ | N | 182–184 |
| H | 3-$CH_3$ | $CH_3$ | $CH_2CH_2F$ | $CH_3$ | $CH_3$ | N | 178–179 |
| H | 3-$CH_3$ | $CH_3$ | $CH_2CH_2CH_2F$ | $CH_3$ | $CH_3$ | CH | 152–153 |
| H | 3-$CH_3$ | $CH_3$ | $CH_2CH_2CH_2F$ | $CH_3$ | $OCH_3$ | CH | 127–128 |
| H | 3-$CH_3$ | $CH_3$ | $CH_2CH_2CH_2F$ | $OCH_3$ | $OCH_3$ | CH | 188–189 |
| H | 3-$CH_3$ | $CH_3$ | $CH_2CH_2CH_2F$ | Cl | $OCH_3$ | CH | 155.5–156.5 |
| H | 3-$CH_3$ | $CH_3$ | $CH_2CH_2CH_2F$ | $CH_3$ | $OCH_3$ | N | 155–156 |
| H | 3-$CH_3$ | $CH_3$ | $CH_2CH_2CH_2F$ | $OCH_3$ | $OCH_3$ | N | 150–151 |
| H | 3-$CH_3$ | $CH_3$ | $CH_2CH_2CH_2F$ | $CH_3$ | $CH_3$ | N | 146–148 |
| H | H | $CH_3$ | $CH_2CH_2F$ | $OCF_2H$ | H | CH | |
| H | H | $CH_3$ | $CH_2CH_2F$ | $OCF_2H$ | $CH_3$ | CH | |
| H | H | $CH_3$ | $CH_2CH_2F$ | $OCF_2H$ | $OCH_3$ | CH | |
| H | H | $CH_3$ | $CH_2CH_2F$ | $OCF_2H$ | $OCF_2H$ | CH | |
| H | H | $CH_3$ | $CH_2CH_2F$ | $OCF_2H$ | $OC_2H_5$ | CH | |
| H | H | $CH_2CF_3$ | $CH_2CF_3$ | $OCF_2H$ | $N(CH_3)_2$ | CH | |
| H | H | $CH_2CF_3$ | $CH_2CF_3$ | $OCF_2H$ | $SCH_3$ | CH | |
| H | H | $CH_2CF_3$ | $CH_2CF_3$ | $OCF_2H$ | Cl | CH | |
| H | H | $CH_2CF_3$ | $CH_2CF_3$ | $OCF_2H$ | $OCH_2CH_2OCH_3$ | CH | |
| H | H | $CH_2CF_3$ | $CH_2CF_3$ | $OCF_2H$ | $CH_2SCH_3$ | CH | |
| H | H | $CH_2CF_3$ | $CH_2C\equiv CH$ | $OCF_2H$ | $OCH_3$ | CH | |
| H | H | $CH_2CF_3$ | $CH_2C\equiv CH$ | $OCF_2H$ | $CH_3$ | CH | |
| H | 5-$OCH_3$ | $CH_2CF_3$ | $CH_2C\equiv CH$ | $OCF_2H$ | $CH_3$ | CH | |
| H | 6-$OCH_3$ | $CH_2CF_3$ | $CH_2C\equiv CH$ | $OCF_2H$ | $CH_3$ | CH | |
| H | 6-Cl | $CH_2CF_3$ | $CH_2C\equiv CH$ | $OCF_2H$ | $CH_3$ | CH | |
| $CH_3$ | H | $CH_2CF_3$ | $CH_2C\equiv CH$ | $OCF_2H$ | $CH_3$ | CH | |
| H | H | —$CH_2CH=CHCH_2$— | $OCF_2H$ | $CH_3$ | CH | | 183–187(d) |
| H | H | —$CH_2CH=CHCH_2$— | $OCF_2H$ | $OCH_3$ | CH | | 212–215 |

TABLE IIIa

Formula III, W = S

| R | $R_1$ | $R_3$ | $R_4$ | X | Y | Z | m.p. (°C.) |
|---|---|---|---|---|---|---|---|
| H | H | $CH_3$ | $CH_2CH_2F$ | $CH_3$ | $OCH_3$ | N | |
| H | H | $CF_2H$ | $CH_2C\equiv CH$ | $OCH_3$ | $OCH_3$ | CH | |
| H | H | $CH_3$ | $CH_2CH_2F$ | $CH_3$ | $OCH_3$ | CH | |
| H | H | $CH_3$ | $CH_2CH_2Cl$ | $OCH_3$ | $OCH_3$ | CH | |
| H | H | $CF_2H$ | $CH_2CH_2F$ | $OCH_3$ | $OCH_3$ | CH | |
| H | H | $CH_3$ | $CH_2CH_2F$ | $CH_3$ | $OCH_3$ | N | |
| H | H | $CH_3$ | $CH_2CH_2F$ | Cl | $OCH_3$ | CH | |
| H | H | $CH_2CF_3$ | $CH_2CF_3$ | $OCH_3$ | $OCH_3$ | CH | |
| H | H | $CH_2CH_2F$ | $CH_2CH_2F$ | $CH_3$ | $OCH_3$ | CH | |
| H | H | $CH_3$ | $CH_2CH_2Cl$ | $OCH_3$ | $OCH_3$ | CH | |
| H | H | $CH_3$ | $CH_2CH_2F$ | $CH_3$ | $OCH_3$ | N | |
| H | H | $CH_3$ | $CH_2CH_2F$ | $OCH_3$ | $OCH_3$ | CH | |
| H | H | $CH_3$ | $CH_2CH_2F$ | $CH_3$ | $OCH_3$ | CH | |
| H | H | $CH_3$ | $CH_2CH_2F$ | $OCH_3$ | $OCH_3$ | CH | |

TABLE IV

Formula IV, W = O

| R | R₁ | R₃ | R₄ | A | X₁ | X₂ | Y | Y₁ | Y₂ | m.p. (°C.) |
|---|---|---|---|---|---|---|---|---|---|---|
| H | H | CH₃ | CH₂CH₂F | A-2 | CH₃ | — | — | O | — | |
| H | H | CH₃ | CH₂CH₂F | A-2 | OCH₃ | — | — | CH₂ | — | |
| H | H | CH₃ | CH₂CH₂F | A-2 | OCH₂F | — | — | O | — | |
| H | H | CH₃ | CH₂CH₂F | A-2 | OC₂H₅ | — | — | O | — | |
| H | H | CH₃ | CH₂-oxirane | A-2 | OCH₃ | — | — | O | — | |
| H | H | CH₃ | CH₂-oxirane | A-2 | CH₃ | — | — | CH₂ | — | |
| H | H | CH₂CF₃ | CF₂H | A-2 | OCH₃ | — | — | CH₂ | — | |
| H | H | CH₂CF₃ | CF₂H | A-2 | OCH₂F | — | — | O | — | |
| H | H | CH₂CF₃ | CF₂H | A-2 | CH₃ | — | — | O | — | |
| H | H | CH₂CF₃ | CH₂CF₃ | A-2 | OCH₃ | — | — | O | — | |
| H | H | CH₂CF₃ | CH₂CF₃ | A-2 | CH₃ | — | — | CH₂ | — | |
| H | H | CH₂CF₃ | CH₂CF₃ | A-2 | OCH₃ | — | — | CH₂ | — | |
| H | H | CF₂H | CH₂C≡CH | A-2 | OCH₃ | — | — | O | — | |
| H | H | CF₂H | CH₂C≡CH | A-2 | OC₂H₅ | — | — | O | — | |
| H | H | CF₂H | CH₂C≡CH | A-2 | CH₃ | — | — | O | — | |
| H | H | CH₂C≡CH | CH₂C≡CH | A-2 | CH₃ | — | — | O | — | |
| H | H | CH₂C≡CH | CH₂C≡CH | A-2 | OCH₃ | — | — | O | — | |
| H | 5-OCH₃ | CH₂C≡CH | CH₂C≡CH | A-2 | OCH₃ | — | — | O | — | |
| H | 6-CL | CH₂C≡CH | CH₂C≡CH | A-2 | OCH₃ | — | — | CH₂ | — | |
| CH₃ | H | CH₂C≡CH | CH₂C≡CH | A-2 | CH₃ | — | — | CH₂ | — | |
| CH₃ | H | CH₂C≡CH | CH₂C≡CH | A-2 | OCH₃ | — | — | O | — | |
| H | H | CH₃ | CH₂CH₂Cl | A-3 | CH₃ | — | — | — | — | |
| H | H | CH₃ | CH₂CH₂Cl | A-3 | OCH₃ | — | — | — | — | |
| H | H | CH₃ | CH₂CH₂Cl | A-3 | OC₂H₅ | — | — | — | — | |
| H | H | CH₃ | CH₂CH₂Cl | A-3 | OCHF₂ | — | — | — | — | |
| H | H | CH₃ | CH₂CH₂Br | A-3 | OCH₃ | — | — | — | — | |
| H | H | CH₂CF₃ | CH₂CH₂Br | A-3 | OCH₃ | — | — | — | — | |
| H | H | CH₂CF₃ | CH₂CH₂Br | A-3 | CH₃ | — | — | — | — | |
| H | H | CH₂CF₃ | CH₂CF₃ | A-3 | CH₃ | — | — | — | — | |
| H | H | CH₂CF₃ | CH₂CF₃ | A-3 | OCH₃ | — | — | — | — | |
| H | H | CF₂H | CH₂CF₃ | A-3 | OCH₃ | — | — | — | — | |
| H | H | CF₂H | CH₂CF₃ | A-3 | OC₂H₅ | — | — | — | — | |
| H | H | CF₂H | CH₂C≡CH₃ | A-3 | OCH₃ | — | — | — | — | |
| H | 5-Br | CH₂CF₃ | CH₂CF₃ | A-3 | CH₃ | — | — | — | — | |
| H | 6-SCH₃ | CH₂CF₃ | CH₂CF₃ | A-3 | OCH₃ | — | — | — | — | |
| CH₃ | H | CH₂CF₃ | CH₂CF₃ | A-3 | OCH₃ | — | — | — | — | |
| CH₃ | H | CH₂CF₃ | CH₂CF₃ | A-3 | CH₃ | — | — | — | — | |
| H | H | CH₃ | CH₂CH₂Br | A-4 | CH₃ | — | — | — | H | |
| H | H | CH₃ | CH₂CH₂Br | A-4 | OCH₃ | — | — | — | H | |
| H | H | CH₃ | CH₂CH₂Br | A-4 | OCH₂F | — | — | — | H | |
| H | H | CH₃ | CH₂CH₂Br | A-4 | OCH₃ | — | — | — | CH₃ | |
| H | H | CH₃ | CH₂CH₂Br | A-4 | CH₃ | — | — | — | CH₃ | |
| H | H | CF₂H | CH₂CF₃ | A-4 | OCH₃ | — | — | — | H | |
| H | H | CF₂H | CH₂CF₃ | A-4 | CH₃ | — | — | — | H | |
| H | H | CF₂H | CH₂C≡CH | A-4 | OCH₃ | — | — | — | H | |
| H | H | CF₂H | CH₂C≡CH | A-4 | CH₃ | — | — | — | CH₃ | |
| H | H | CH₂C≡CH | CH₂C≡CH | A-4 | OCH₃ | — | — | — | H | |
| H | 5-SCH₃ | CH₂C≡CH | CH₂C≡CH | A-4 | OCH₃ | — | — | — | H | |
| H | 6-CH₃ | CH₂C≡CH | CH₂C≡CH | A-4 | OCH₃ | — | — | — | CH₃ | |
| CH₃ | H | CH₂C≡CH | CH₂C≡CH | A-4 | CH₃ | — | — | — | H | |
| H | H | CH₃ | CH₂CH₂Cl | A-5 | — | CH₃ | — | — | — | |
| H | H | CH₃ | CH₂CH₂Cl | A-5 | — | OCH₃ | — | — | — | |
| H | H | CH₃ | CH₂CH(OCH₃)₂ | A-5 | — | CH₃ | — | — | — | |
| H | H | CH₃ | CH₂CH(OCH₃)₂ | A-5 | — | OCH₃ | — | — | — | |
| H | H | CH₂CF₃ | CF₂H | A-5 | — | OCH₃ | — | — | — | |
| H | H | CH₂CF₃ | CF₂H | A-5 | — | CH₃ | — | — | — | |
| H | H | CH₂CF₃ | CH₂CF₃ | A-5 | — | OCH₃ | — | — | — | |
| H | 6-Br | CH₂CF₃ | CH₂CF₃ | A-5 | — | OCH₃ | — | — | — | |
| CH₃ | H | CH₂CF₃ | CH₂CF₃ | A-5 | — | OCH₃ | — | — | — | |

TABLE IVa

Formula IV, W = S

| R | R₁ | R₃ | R₄ | A | X₁ | X₂ | Y | Y₁ | Y₂ | m.p. (°C.) |
|---|---|---|---|---|---|---|---|---|---|---|
| H | H | CH₃ | CH₂CH₂F | A-2 | OCH₃ | — | — | O | — | |
| H | H | CH₃ | CH₂CH₂F | A-2 | OCH₃ | — | — | CH₂ | — | |
| H | H | CF₂H | CH₂CH₂F | A-3 | CH₃ | — | — | — | — | |
| H | H | CH₃ | CH₂CH₂Cl | A-3 | OCH₃ | — | — | — | — | |
| H | H | CH₃ | CH₂CH₂Br | A-4 | CH₃ | — | — | — | CH₃ | |
| H | H | CH₂CF₃ | CH₂CF₃ | A-4 | OCH₃ | — | — | — | H | |
| H | H | CH₃ | CH₂CH₂F | A-5 | — | OCH₃ | — | — | — | |
| H | H | CHF₂ | CH₂CF₃ | A-5 | — | OCH₃ | — | — | — | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE V

|  | Active Ingredient | Weight Percent* | |
|---|---|---|---|
|  |  | Diluent (s) | Surfactant (s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8–59ff.

In the following examples, all parts are by weight unless otherwise indicated.

EXAMPLE 3

Wettable Powder

| | |
|---|---|
| N-Cyclopropyl-N'-8 (4,6-dimethoxypyrimidin-2-yl)aminocarbonyl]-1,2-benzenedisulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 4

Granule

| | |
|---|---|
| Wettable Powder of Example 3 | 5% |
| attapulgite granules (U.S.S. 20–40 mesh: 0.84–0.42 mm) | 95% |

A slurry of wettable powder containing 25% solids is sprayed on the surface of attapulgite granules in a double-cone blender. The granules are dried and packaged.

EXAMPLE 5

Extruded Pellet

| | |
|---|---|
| N-Cyclopropyl-N'-[(4-methoxy-6-methyl-1,3,5-triazin-2-yl)aminocarbonyl]-1,2-benzenedisulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Low Strength Granule

| | |
|---|---|
| N-Cyclopropyl-N'-[(4,6-dimethoxypyrimidin-2-yl)aminocarbonyl]-1,2-benzenedisulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 7

Aqueous Suspension

| | |
|---|---|
| N-Cyclopropyl-N'-[(4-methoxy-6-methyl-1,3,5-triazin-2-yl)aminocarbonyl]-1,2-benzenedisulfonamide | 40% |

| -continued | |
|---|---|
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 8

Oil Suspension

| | |
|---|---|
| N-Cyclopropyl-N'-[(4,6-dimethoxypyrimidin-2-yl)amino-carbonyl]-1,2-benzenedisulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 9

Granule

| | |
|---|---|
| N-Cyclopropyl-N'-[(4-methoxy-6-methyl-1,3,5-triazin-2-yl)aminocarbonyl]-1,2-benzenedisulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 10

High Strength Concentrate

| | |
|---|---|
| N-Cyclopropyl-N'-[(4,6-dimethoxypyrimidin-2-yl)amino-carbonyl]-1,2-benzenedisulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 11

Wettable Powder

| | |
|---|---|
| N-Cyclopropyl-N'-[(4-methoxy-6-methyl-1,3,5-triazin-2-yl)aminocarbonyl]-1,2-benzenedisulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 12

Wettable Powder

| | |
|---|---|
| N-Cyclopropyl-N'-[(4.6-dimethoxypyrimidin-2-yl)amino-carbonyl]-1,2-benzenedisulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 13

Dust

| | |
|---|---|
| N-Cyclopropyl-N'-[(4-methoxy-6-methyl-1,3,5-triazin-2-yl)aminocarbonyl]-1,2-benzenedisulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulators. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria spp.), barnyardgrass (*Echinochloa crusgalli*), wild oats (*Avena fatua*), cheatgrass (*Bromus secalinus*), velvetleaf (*Abutilon theophrasti*), morningglory (Ipomoea spp.), cocklebur (*Xanthium Pensylvanicum*), sorghum, corn, soybean, sugar beet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

B=burn:
C=chlorosis/necrosis:
D=defoliation:
E=emergence inhibition:
G=growth retardation:
H=formative effect:
U=unusual pigmentation:
X=axillary stimulation:
S=albinism; and
6Y=abscised buds or flowers.

Compounds

| Compound | $R_2$ | X | Y | Z |
|---|---|---|---|---|
| 1 | $CH_2C_6H_5$ | $CH_3$ | $CH_3$ | CH |
| 2 | $CH_2C_6H_5$ | $OCH_3$ | $CH_3$ | CH |
| 3 | $CH_2C_6H_5$ | $OCH_3$ | $OCH_3$ | CH |
| 4 | $CH_2C_6H_5$ | Cl | $OCH_3$ | CH |
| 5 | $CH_2C_6H_5$ | $OCH_3$ | $CH_3$ | N |
| 6 | $CH_2C_6H_5$ | $OCH_3$ | $OCH_3$ | N |
| 7 | cyclopropyl | $CH_3$ | $CH_3$ | CH |
| 8 | cyclopropyl | $CH_3$ | $OCH_3$ | CH |
| 9 | cyclopropyl | $OCH_3$ | $OCH_3$ | CH |
| 10 | cyclopropyl | Cl | $OCH_3$ | CH |
| 11 | cyclopropyl | $OCH_3$ | $CH_3$ | N |
| 12 | cyclopropyl | $OCH_3$ | $OCH_3$ | N |
| 13 | cyclobutyl | $CH_3$ | $CH_3$ | CH |
| 14 | cyclobutyl | $CH_3$ | $OCH_3$ | CH |
| 15 | cyclobutyl | $OCH_3$ | $OCH_3$ | CH |
| 16 | cyclobutyl | Cl | $OCH_3$ | CH |
| 17 | cyclobutyl | $OCH_3$ | $CH_3$ | N |
| 18 | cyclobutyl | $OCH_3$ | $OCH_3$ | N |
| 19 | $OCH_3$ | $CH_3$ | $CH_3$ | CH |
| 20 | $OCH_3$ | $CH_3$ | $OCH_3$ | CH |
| 21 | $OCH_3$ | $OCH_3$ | $OCH_3$ | CH |
| 22 | $OCH_3$ | Cl | $OCH_3$ | CH |
| 23 | $OCH_3$ | $CH_3$ | $OCH_3$ | N |
| 24 | $OCH_3$ | $OCH_3$ | $OCH_3$ | N |
| 25 | $CH_2CH(OCH_3)_2$ | $CH_3$ | $CH_3$ | CH |
| 26 | $CH_2CH(OCH_3)_2$ | $CH_3$ | $OCH_3$ | CH |
| 27 | $CH_2CH(OCH_3)_2$ | $OCH_3$ | $OCH_3$ | CH |
| 28 | $CH_2CH(OCH_3)_2$ | Cl | $OCH_3$ | CH |
| 29 | $CH_2CH(OCH_3)_2$ | $CH_3$ | $OCH_3$ | N |
| 30 | $CH_2CH(OCH_3)_2$ | $OCH_3$ | $OCH_3$ | N |
| 31 | $CH_2C{\equiv}CH$ | $CH_3$ | $CH_3$ | CH |
| 32 | $CH_2C{\equiv}CH$ | $CH_3$ | $OCH_3$ | CH |
| 33 | $CH_2C{\equiv}CH$ | $OCH_3$ | $OCH_3$ | CH |
| 34 | $CH_2C{\equiv}CH$ | Cl | $OCH_3$ | CH |
| 35 | $CH_2C{\equiv}CH$ | $CH_3$ | $OCH_3$ | N |
| 36 | $CH_2C{\equiv}CH$ | $OCH_3$ | $OCH_3$ | N |
| 37 | $CH_2CH_2F$ | $CH_3$ | $CH_3$ | CH |
| 38 | $CH_2CH_2F$ | $OCH_3$ | $OCH_3$ | CH |
| 39 | $CH_2CH_2F$ | Cl | $OCH_3$ | CH |
| 40 | $CH_2CH_2F$ | $CH_3$ | $OCH_3$ | CH |
| 41 | $CH_2CH_2F$ | $CH_3$ | $OCH_3$ | N |
| 42 | $CH_2CH_2F$ | $OCH_3$ | $OCH_3$ | N |
| 43 | cyclopentyl | $CH_3$ | $CH_3$ | CH |
| 44 | cyclopentyl | $CH_3$ | $OCH_3$ | CH |
| 45 | cyclopentyl | $OCH_3$ | $OCH_3$ | CH |
| 46 | cyclopentyl | Cl | $OCH_3$ | CH |
| 47 | cyclopentyl | $CH_3$ | $OCH_3$ | N |
| 48 | cyclopentyl | $OCH_3$ | $OCH_3$ | N |

-continued

Compounds

| | | | | |
|---|---|---|---|---|
| 49 | CH₂CH₂OH | CH₃ | CH₃ | CH |
| 50 | CH₂CH₂OH | CH₃ | OCH₃ | CH |
| 51 | CH₂CH₂OH | OCH₃ | OCH₃ | CH |
| 52 | CH₂CH₂OH | Cl | OCH₃ | CH |
| 53 | CH₂CH₂OH | CH₃ | OCH₃ | N |
| 54 | CH₂CH₂OH | OCH₃ | OCH₃ | N |
| 55 | CH₂CH₂N(CH₃)₂ | CH₃ | OCH₃ | CH |
| 56 | CH₂–(epoxide) | OCH₃ | OCH₃ | CH |
| 57 | CH₂CH₂CH₂Br | CH₃ | CH₃ | CH |
| 58 | CH₂CH₂CH₂Br | CH₃ | OCH₃ | CH |
| 59 | CH₂CH₂CH₂Br | OCH₃ | OCH₃ | CH |
| 60 | CH₂CH₂CH₂Br | CH₃ | OCH₃ | CH |
| 61 | CH₂CH₂CH₂Br | OCH₃ | OCH₃ | N |
| 62 | CH₂CH₂CH₂Br | Cl | OCH₃ | N |
| 63 | CH₂-cyclopropyl | CH₃ | CH₃ | CH |
| 64 | CH₂-cyclopropyl | CH₃ | OCH₃ | CH |
| 65 | ch₂-cyclopropyl | OCH₃ | OCH₃ | CH |
| 66 | CH₂-cyclopropyl | CH₃ | OCH₃ | CH |
| 67 | CH₂-cyclopropyl | OCH₃ | OCH₃ | N |
| 68 | CH₂-cyclopropyl | Cl | OCH₃ | N |
| 69 | CH₂CF₂CF₃ | CH₃ | CH₃ | CH |
| 70 | CH₂CF₂CF₃ | CH₃ | OCH₃ | CH |
| 71 | CH₂CF₂CF₃ | OCH₃ | OCH₃ | CH |
| 72 | CH₂CF₂CF₃ | CH₃ | OCH₃ | N |
| 73 | CH₂CF₂CF₃ | OCH₃ | OCH₃ | N |

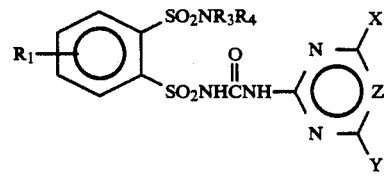

| Compound | $R_1$ | $R_2$ | $R_3$ | X | Y | Z | m.p. (°C.) |
|---|---|---|---|---|---|---|---|
| 74 | 3-CH₃ | CH₃ | CH₂CH₂F | CH₃ | CH₃ | CH | 175 to 176 |
| 75 | 3-CH₃ | CH₃ | CH₂CH₂F | CH₃ | OCH₃ | CH | 170 to 171 |
| 76 | 3-CH₃ | CH₃ | CH₂CH₂F | OCH₃ | OCH₃ | CH | 212 to 214 |
| 77 | 3-CH₃ | CH₃ | CH₂CH₂F | Cl | OCH₃ | CH | 172 to 173 |
| 78 | 3-CH₃ | CH₃ | CH₂CH₂F | CH₃ | OCH₃ | N | 177 to 178 |
| 79 | 3-CH₃ | CH₂-CH₂F | OCH₃ | OCH₃ | N | | 182 to 184 |
| 80 | 3-CH₃ | CH₃ | CH₂CH₂F | CH₃ | CH₃ | N | 178 to 179 |
| 81 | 3-CH₃ | CH₃ | CH₂CH₂CH₂F | CH₃ | CH₃ | CH | 152 to 153 |
| 82 | 3-CH₃ | CH₃ | CH₂CH₂CH₂F | CH₃ | OCH₃ | CH | 127 to 128 |
| 83 | 3-CH₃ | CH₃ | CH₂CH₂CH₂F | OCH₃ | OCH₃ | CH | 188 to 189 |
| 84 | 3-CH₃ | CH₃ | CH₂CH₂CH₂F | Cl | OCH₃ | CH | 155.5 to 156.5 |
| 85 | 3-CH₃ | CH₃ | CH₂CH₂CH₂F | CH₃ | CH₃ | N | 155 to 156 |
| 86 | 3-CH₃ | CH₃ | CH₂CH₂CH₂F | OCH₃ | OCH₃ | N | 150 to 151 |
| 87 | 3-CH₃ | CH₃ | CH₂CH₂CH₂F | CH₃ | CH₃ | N | 146 to 148 |
| 88 | H | —CH₂CH=CHCH₂— | | Cl | OCH₃ | CH | 210 to 217(d) |
| 89 | H | —CH₂CH=CHCH₂— | | OCH₃ | OCH₃ | CH | 220 to 230(d) |
| 90 | H | —CH₂CH=CHCH₂— | | CH₃ | OCH₂CH₂CH₃ | CH | 193 to 196(d) |
| 91 | H | —CH₂CH=CHCH₂— | | CH₃ | OCH(CH₃)₂ | CH | 173 to 179 |
| 92 | H | —CH₂CH=CHCH₂— | | OCF₂H | CH₃ | CH | 183 to 187(d) |
| 93 | H | —CH₂CH=CHCH₂— | | OCF₂H | OCH₃ | CH | 212 to 215 |

TABLE A

| Rate kg/ha | Cmpd. 1 0.05 | Cmpd. 2 0.05 | Cmpd. 3 0.05 | Cmpd. 4 0.05 |
|---|---|---|---|---|
| POSTEMERGENCE | | | | |
| Morningglory | 0 | 4C,9G | 9C | 4C,9G |
| Cocklebur | 4C,9G | 5C,9G | 10C | 5C,9G |
| Velvetleaf | 4C,8H | 9C | 9C | 4C,8H |
| Nutsedge | 2G | 3C,8G | 3C,9G | 3C,8G |
| Crabgrass | 0 | 3G | 2C,8G | 2G |
| Barnyardgrass | 5H | 2C,7H | 9C | 3C,7H |
| Cheatgrass | 2C,7G | 9C | 5C,9G | 6G |
| Wild Oats | 6G | 6G | 8G | 0 |
| Wheat | 3G | 2G | 6G | 0 |
| Corn | 2C,5H | 2C,8G | 2U,9G | 2G |
| Soybean | 4C,8H | 9C | 9C | 3C,7G |
| Rice | 5C,9G | 6C,9G | 6C,9G | 3C,8G |
| Sorghum | 2C,8G | 3C,9H | 9C | 4C,9H |
| Sugar beet | 9C | 4C,8G | 9C | 4C,8H |
| Cotton | 4C,9H | 9C | 5C,9G | 4C,9H |
| PREEMERGENCE | | | | |
| Morninglory | 6G | 6G | 9G | 6G |
| Cocklebur | 5H | 8H | 8H | 0 |
| Velvetleaf | 6H | 4C,9G | 5C,9G | 5G |
| Nutsedge | 0 | 6G | 10E | 5G |
| Crabgrass | 2G | 2G | 5G | 2G |
| Barnyardgrass | 0 | 3C,8H | 3C,9H | 3H |
| Cheatgrass | 8G | 5C,9H | 4C,8H | 6G |
| Wild Oats | 2C,6G | 2C,9G | 3C,9H | 3G |

TABLE A-continued

| | | | | |
|---|---|---|---|---|
| Wheat | 6G | 8G | 2C,9G | 3G |
| Corn | 6G | 2C,9G | 9G | 3C,6G |
| Soybean | 0 | 3C,7G | 3C,6G | 0 |
| Rice | 9H | 10E | 10E | 9H |
| Sorghum | 4C,5G | 4C,9H | 9H | 2C,9G |
| Sugar beet | 4C,8G | 5c,9G | 9G | 8G |
| Cotton | 4G | 7G | 8G | 4G |

| | Cmpd. 5 | Cmpd. 6 | Cmpd. 7 | Cmpd. 8 |
|---|---|---|---|---|
| Rate kg/ha | 0.05 | 0.05 | 0.05 | 0.05 |
| POSTEMERGENCE | | | | |
| Morningglory | 4C,8G | 4C,8H | 5C,9G | 10C |
| Cocklebur | 3C,5G | 0 | 9C | 10C |
| Velvetleaf | 5C,9G | 4C,8H | 9C | 9C |
| Nutsedge | 0 | 0 | 8G | 2C,7G |
| Crabgrass | 2G | 0 | 4G | 4G |
| Barnyardgrass | 3C,9H | 3C,6H | 3C,9H | 3C,8H |
| Cheatgrass | 4C,9G | 2C,7G | 3C,8G | 4C,8G |
| Wild Oats | 5C,9G | 5C,9H | 8G | 2C,5G |
| Wheat | 4C,9G | 2G | 5G | 2G |
| Corn | 5U,9C | 3C,9H | 7H | 4C,9H |
| Soybean | 9C | 5C,9G | 9C | 9C |
| Rice | 6C,9G | 6C,9G | 5C,9G | 5C,9G |
| Sorghum | 3C,8H | 3C,6H | 3U,9H | 2C,8G |
| Sugar beet | 9C | 5C,9H | 3C,6G | 5C,9G |
| Cotton | 5C,9G | 5C,9G | 9C | 5C,9G |
| PREEMERGENCE | | | | |
| Morningglory | 7G | 4G | 9G | 8G |
| Cocklebur | 4G | 0 | 8H | 8H |
| Velvetleaf | 2C,8G | 3C,8H | 4C,9G | 9G |
| Nutsedge | 0 | 0 | 7G | 10E |
| Crabgrass | 0 | 0 | 5G | 8G |
| Barnyardgrass | 3H | 0 | 6G | 4C,9H |
| Cheatgrass | 3C,8H | 2G | 7G | 9H |
| Wild Oats | 3C,8G | 0 | 8G | 3C,7G |
| Wheat | 2C,8G | 0 | 8G | 7G |
| Corn | 8G | 3C,7G | 8G | 2C,9G |
| Soybean | 3C,3G | 2C | 5H | 3C,6H |
| Rice | 9H | 4C,8H | 10E | 5C,9H |
| Sorghum | 3C,9H | 4C,6H | 10E | 3C,9H |
| Sugar beet | 9G | 5C,9G | 6G | 8G |
| Cotton | 7G | 7G | 8G | 9G |

| | Cmpd. 9 | Cmpd. 10 | Cmpd. 11 | Cmpd. 11 |
|---|---|---|---|---|
| Rate kg/ha | 0.05 | 0.05 | 0.05 | 0.05 |
| POSTEMERGENCE | | | | |
| Morningglory | 9C | 9C | 10C | 9C |
| Cocklebur | 10C | 9C | 10C | 10C |
| Velvetleaf | 9C | 2C,8G | 9C | 5C,9G |
| Nutsedge | 5C,9G | 2C,7G | 3G | 4G |
| Crabgrass | 7G | 4G | 7G | 6G |
| Barnyardgrass | 5C,9G | 3C,9H | 5C,9H | 3C,7H |
| Cheatgrass | 5C,9G | 8G | 5C,9G | 3C,8G |
| Wild Oats | 3C,7G | 0 | 5C,9G | 4C,8G |
| Wheat | 0 | 0 | 2C,9G | 5G |
| Corn | 4U,8H | 3H | 10C | 10C |
| Soybean | 5C,9G | 3C,8G | 9C | 9C |
| Rice | 4C,9G | 7G | 5C,9G | 5C,9G |
| Sorghum | 4U,9H | 3U,9G | 5U,9C | 6C,9H |
| Sugar beet | 9C | 3C,6H | 9C | 9C |
| Cotton | 4C,9H | 5C,9H | 5C,9G | 5C,9H |
| PREEMERGENCE | | | | |
| Morningglory | 9G | 9G | 9G | 9G |
| Cocklebur | — | 4C,5H | 9H | — |
| Velvetleaf | 5C,9G | 3G | 5C,9G | 5C,9G |
| Nutsedge | 10E | 10E | 3G | 4G |
| Crabgrass | 5C,9G | 5G | 7G | 8G |
| Barnyardgrass | 9H | 3C,7H | 3C,8H | 3C,8H |
| Cheatgrass | 9H | 5G | 2C,7H | 2C,5G |
| Wild Oats | 3C,6G | 2G | 3C,8H | 2C,6G |
| Wheat | 3G | 0 | 2C,8G | 3C,8G |
| Corn | 9G | 2C,5G | 5C,9G | 3C,9G |
| Soybean | 5H | 0 | 4C,6H | 3C,6H |
| Rice | 10E | 3C,8H | 10E | 5C,9H |
| Sorghum | 2C,9G | 3C,8H | 10E | 5C,9H |
| Sugar beet | 9G | 7G | 5C,9G | 5C,9G |
| Cotton | 9G | 8G | 9G | 8G |

| | Cmpd. 13 | Cmpd. 14 | Cmpd. 15 | Cmpd. 16 |
|---|---|---|---|---|
| Rate kg/ha | 0.05 | 0.05 | 0.05 | 0.05 |
| POSTEMERGENCE | | | | |
| Morningglory | 2H | 4C,9G | 9C | 4C,8H |
| Cocklebur | 4C,9G | 9C | 9C | 5C,9G |
| Velvetleaf | 4C,8H | 4C,8H | 5C,9G | 4G |
| Nutsedge | 5G | 3C,8G | 7G | 7G |
| Crabgrass | 0 | 4G | 6G | 2G |
| Barnyardgrass | 2H | 3C,8H | 3C,9H | 2C,8H |
| Cheatgrass | 3C,8G | 4C,8G | 4C,8G | 5G |
| Wild Oats | 8G | 7G | 8G | 2G |
| Wheat | 0 | 0 | 5G | 0 |
| Corn | 3C,6H | 4U,9G | 4C,9G | 6H |
| Soybean | 3C,8G | 9C | 5C,9G | 2C,5H |
| Rice | 5C,9G | 5C,9G | 5C,9G | 8G |
| Sorghum | 3C,7H | 4C,9H | 4C,9H | 2C,9H |
| Sugar beet | 4C,8H | 9C | 5C,9G | 2C,3G |
| Cotton | 4C,7H | 4C,7G | 4C,9G | 4C,8G |
| PREEMERGENCE | | | | |
| Morningglory | 5G | 8G | 9G | 7G |
| Cocklebur | 4G | 7H | 8H | 1C |
| Velvetleaf | 0 | 8G | 9G | 0 |
| Nutsedge | 0 | 8G | 10E | 0 |
| Crabgrass | 4G | 4G | 3G | 3G |
| Barnyardgrass | 0 | 8G | 9H | 2G |
| Cheatgrass | 6G | 9H | 10E | 5G |
| Wild Oats | 2C,5G | 4C,7H | 2C,8H | 3G |
| Wheat | 4G | 8G | 8H | 0 |
| Corn | 2C,5G | 4C,9H | 9G | 2C,5G |
| Soybean | 1H | 4C,6H | 3C,6H | 0 |
| Rice | 8H | 9H | 10E | 3C,8H |
| Sorghum | 3C,7G | 5C,9H | 4C,9H | 3C,9H |
| Sugar beet | 8G | 5C,9G | 9G | 8G |
| Cotton | 3G | 9G | 9G | 0 |

| | Cmpd. 17 | Cmpd. 18 | Cmpd. 19 | Cmpd. 20 |
|---|---|---|---|---|
| Rate kg/ha | 0.05 | 0.05 | 0.05 | 0.05 |
| POSTEMERGENCE | | | | |
| Morningglory | 9C | 5C,9G | 10C | 6C,9G |
| Cocklebur | 3C,9G | 5G | 9C | 9C |
| Velvetleaf | 5C,9G | 3C,7G | 9C | 9C |
| Nutsedge | 0 | 4G | 4C,9G | 4C,9G |
| Crabgrass | 3G | 2G | 6G | 4C,8G |
| Barnyardgrass | 4C,9H | 3C,7H | 3C,8H | 4C,8H |
| Cheatgrass | 2C,7G | 5G | 2C,8G | 9C |
| Wild Oats | 4G | 8G | 5G | 3G |
| Wheat | 4G | 7G | 4G | 5G |
| Corn | 5C,9G | 3U,9G | 7H | 8H |
| Soybean | 9C | 5C,9G | 4C,8G | 9C |
| Rice | 5C,9G | 9G | 5C,9G | 9C |
| Sorghum | 3U,9G | 5C,9G | 3C,8G | 8H |
| Sugar beet | 9C | 3C,7G | 5C,9G | 5C,9G |
| Cotton | 4C,9G | 4C,7G | 9C | 9C |
| PREEMERGENCE | | | | |
| Morningglory | 9G | 7H | 9H | 9G |
| Cocklebur | 5H | 1C | 9H | — |
| Velvetleaf | 2G | 0 | 5C,9G | 5C,9G |
| Nutsedge | 0 | 0 | 8G | 9G |
| Crabgrass | 5G | 2G | 4C,8G | 7G |
| Barnyardgrass | 2G | 0 | 3C,8H | 3C,8H |
| Cheatgrass | 5G | 0 | 3C,9H | 9H |
| Wild Oats | 2H | 0 | 4C,8G | 2C,8G |
| Wheat | 6G | 3G | 6C,9H | 3C,8H |
| Corn | 8G | 3C,7G | 3U,9H | 5U,9H |
| Soybean | 2C,5H | 1C | 7H | 8H |
| Rice | 7H | 5G | 10H | 10E |
| Sorghum | 4C,9H | 3C,5G | 9H | 9H |
| Sugar beet | 4C,8G | 8G | 10C | 10E |
| Cotton | 7G | 3G | 8G | 9G |

| | Cmpd. 21 | Cmpd. 22 | Cmpd. 23 | Cmpd. 24 |
|---|---|---|---|---|
| Rate kg/ha | 0.05 | 0.05 | 0.05 | 0.05 |
| POSTEMERGENCE | | | | |
| Morningglory | 10C | 10C | 10C | 10C |
| Cocklebur | 10C | 9C | 9C | 4G |
| Velvetleaf | 9C | 5C,9G | 9C | 9C |
| Nutsedge | 6C,9G | 5C,9G | 4G | 3G |
| Crabgrass | 3C,5G | 2C,5G | 5C,9G | 3C,8G |
| Barnyardgrass | 9C | 4C,7H | 5C,9H | 6C,9H |
| Cheatgrass | 9C | 6G | 3C,6G | 5G |
| Wild Oats | 3C,7G | 0 | 6C,9G | 5C,9G |
| Wheat | 4G | 0 | 5C,9G | 2C,7G |
| Corn | 6C,9H | 6H | 9C | 10C |
| Soybean | 9C | 5C,9G | 9C | 9C |

TABLE A-continued

| | | | | |
|---|---|---|---|---|
| Rice | 6C,9G | 4C,7G | 9C | 9C |
| Sorghum | 9C | 4C,8H | 9C | 6C,9H |
| Sugar beet | 10C | 3C,6G | 10C | 9C |
| Cotton | 10C | 9C | 10C | 9C |

PREEMERGENCE

| | | | | |
|---|---|---|---|---|
| Morningglory | 9G | 8G | 9G | 9G |
| Cocklebur | 8H | 9H | 9H | 8H |
| Velvetleaf | 5C,9G | 8G | 9C | 3C,7G |
| Nutsedge | 10E | 10E | 5G | 0 |
| Crabgrass | 3C,7G | 0 | 3C,7G | 2C,5G |
| Barnyardgrass | 8H | 4C,4H | 3C,8H | 3C,7H |
| Cheatgrass | 9H | 2C,5G | 3C,7H | 3C,6G |
| Wild Oats | 3C,6G | 2C,4G | 5C,9H | 3C,8G |
| Wheat | 5G | 2G | 4C,9H | 4C,9G |
| Corn | 5U,9G | 3C,8G | 3C,9H | 5C,9H |
| Soybean | 8H | 2H | 8H | 4C,8H |
| Rice | 10E | 9H | 10E | 10E |
| Sorghum | 5C,9H | 3C,8G | 10E | 5C,9H |
| Sugar beet | 9G | 3C,8G | 10C | 5C,9G |
| Cotton | 9G | 8G | 4C,9G | 5C,9G |

| Rate kg/ha | Cmpd. 25 0.05 | Cmpd. 26 0.05 | Cmpd. 27 0.05 | Cmpd. 28 0.05 |
|---|---|---|---|---|

POSTEMERGENCE

| | | | | |
|---|---|---|---|---|
| Morningglory | 2C,7G | 3C,8G | 3C,9H | 2C,4G |
| Cocklebur | 3C,9H | 3C,9H | 5C,9G | 8H |
| Velvetleaf | 6H | 3C,8G | 9C | 1H |
| Nutsedge | 2G | 4G | 2C,9G | 0 |
| Crabgrass | 3G | 2G | 3C,7G | 2G |
| Barnyardgrass | 3C,9H | 3C,9H | 9H | 3C,9H |
| Cheatgrass | 2C,7G | 3C,6G | 3C,8G | 3G |
| Wild Oats | 2C,4G | 2C,8G | 7G | 0 |
| Wheat | 0 | 0 | 4G | 0 |
| Corn | 4G | 2C,8H | 3C,9H | 5G |
| Soybean | 2C,9G | 5C,9G | 5C,9G | 5H |
| Rice | 4C,9G | 4C,9G | 6C,9G | 4C,9G |
| Sorghum | 4C,8H | 4C,9H | 9H | 4C,8H |
| Sugar beet | 3C,7H | 3C,6G | 3C,9G | 2G |
| Cotton | 2C,5G | 2C,5G | 4C,9G | 2G |

PREEMERGENCE

| | | | | |
|---|---|---|---|---|
| Morningglory | 2C,4G | 7G | 3C,5G | 2C,9G |
| Cocklebur | 2C | 10C | 8H | 2H |
| Velvetleaf | 3G | 8G | 5C,9G | 2G |
| Nutsedge | 0 | 4G | 8G | 0 |
| Crabgrass | 0 | 0 | 4G | 0 |
| Barnyardgrass | 0 | 3C,8H | 4C,9H | 3C,7H |
| Cheatgrass | 2G | 8G | 8G | 4G |
| Wild Oats | 2C,5G | 3C,7G | 2C,8G | 3C,3G |
| Wheat | 0 | 2C,5G | 3C,9G | 2G |
| Corn | 2C,5G | 3C,8H | 4C,9G | 2C,5G |
| Soybean | 2C,2H | 6G | 3C,3H | 3C,3G |
| Rice | 3C,8H | 3C,8H | 4C,9H | 8H |
| Sorghum | 3C,7H | 3C,8H | 4C,9H | 3C,8G |
| Sugar beet | 2C,5G | 2C,8G | 6G | 2G |
| Cotton | 0 | 7G | 3C,5G | 3G |

| Rate kg/ha | Cmpd. 29 0.05 | Cmpd. 30 0.05 | Cmpd. 31 0.05 | Cmpd. 32 0.05 |
|---|---|---|---|---|

POSTEMERGENCE

| | | | | |
|---|---|---|---|---|
| Morningglory | 3C,8G | 2C,5G | 10C | 10C |
| Cocklebur | 2G | 0 | 9C | 9C |
| Velvetleaf | 2G | 0 | 10C | 10C |
| Nutsedge | 0 | 0 | 7G | 2C,8G |
| Crabgrass | 2G | 0 | 6G | 3C,7H |
| Barnyardgrass | 4H | 0 | 3C,8H | 9H |
| Cheatgrass | 0 | 0 | 3C,9G | 5C,9G |
| Wild Oats | 0 | 0 | 3C,8H | 4C,8G |
| Wheat | 0 | 0 | 3G | 0 |
| Corn | 5H | 5H | 2H | 9H |
| Soybean | 3C,9G | 2C,8H | 2C,5G | 5C,9G |
| Rice | 2C,8G | 5G | 5C,9G | 5C,9G |
| Sorghum | 2H | 2G | 4C,9H | 2C,9H |
| Sugar beet | 3C,7G | 2C,5G | 9C | 9C |
| Cotton | 1H | 2C,6H | 4C,8G | 9C |

PREEMERGENCE

| | | | | |
|---|---|---|---|---|
| Morningglory | 2C,4G | 2C,4G | 9H | 9H |
| Cocklebur | 5G | 2H | 9H | 9H |
| Velvetleaf | 5G | 2G | 9G | 9C |
| Nutsedge | 0 | 0 | 4G | 7G |
| Crabgrass | 2G | 3G | 3G | 5G |
| Barnyardgrass | 0 | 1C | 3C,6G | 2C,8H |
| Cheatgrass | 0 | 0 | 8H | 10E |
| Wild Oats | 0 | 2G | 2C,8G | 5C,9G |
| Wheat | 0 | 2G | 7G | 8G |
| Corn | 2G | 0 | 2C,7G | 9H |
| Soybean | 0 | 1C | 2C,3G | 3C,7H |
| Rice | 3G | 0 | 9H | 10E |
| Sorghum | 2C,4G | 0 | 3C,9G | 10H |
| Sugar beet | 0 | 7G | 8G | 9C |
| Cotton | 0 | 2G | 9C | 9C |

| Rate kg/ha | Cmpd. 33 0.05 | Cmpd. 34 0.05 | Cmpd. 35 0.05 | Cmpd. 36 0.05 |
|---|---|---|---|---|

POSTEMERGENCE

| | | | | |
|---|---|---|---|---|
| Morningglory | 10C | 10C | 10C | 10C |
| Cocklebur | 9C | 9C | 10C | 8G |
| Velvetleaf | 10C | 10C | 10C | 9C |
| Nutsedge | 2C,9G | 9G | 4G | 5G |
| Crabgrass | 3C,8G | 6G | 4C,8G | 4C,8G |
| Barnyardgrass | 5C,9H | 4C,9H | 9C | 3C,5H |
| Cheatgrass | 9C | 2C,9G | 9C | 8G |
| Wild Oats | 4C,9G | 0 | 9C | 5C,8G |
| Wheat | 3G | 0 | 5C,9G | 8G |
| Corn | 2C,9G | 5H | 9C | 4U,9G |
| Soybean | 9C | 3C,8G | 5C,9G | 5C,9G |
| Rice | 6C,9G | 5C,9G | 9C | 9C |
| Sorghum | 3C,9G | 4C,9H | 4U,9G | 3C,9H |
| Sugar beet | 9C | 3C,8G | 9C | 9C |
| Cotton | 9C | 9C | 9C | 4C,9H |

PREEMERGENCE

| | | | | |
|---|---|---|---|---|
| Morningglory | 3C,9H | 9G | 9H | 9H |
| Cocklebur | 9H | 8H | 9H | 8G |
| Velvetleaf | 9G | 9C | 9C | 9C |
| Nutsedge | 10E | 3C,9G | 0 | 0 |
| Crabgrass | 7G | 4G | 2C,4G | 4G |
| Barnyardgrass | 9H | 3C,7H | 3C,8H | 2C,3G |
| Cheatgrass | 10H | 2C,8G | 3C,7G | 3G |
| Wild Oats | 3C,8G | 2C,5G | 3C,6G | 2C,3G |
| Wheat | 2C,8G | 0 | 3C,8G | 3C,6G |
| Corn | 2U,9H | 3C,7G | 3C,9H | 3C,9G |
| Soybean | 9H | 2C,2H | 2C,3G | 3C,3H |
| Rice | 10E | 5C,9H | 9H | 5C,9H |
| Sorghum | 5C,9H | 3C,9G | 5C,9H | 4C,9H |
| Sugar beet | 9G | 4C,8G | 9C | 9C |
| Cotton | 9G | 9G | 9G | 9G |

| Rate kg/ha | Cmpd. 37 0.05 | Cmpd. 38 0.05 | Cmpd. 39 0.05 |
|---|---|---|---|

POSTEMERGENCE

| | | | |
|---|---|---|---|
| Morningglory | 9C | 10C | 10C |
| Cocklebur | 9C | 10C | 10C |
| Velvetleaf | 10C | 10C | 9C |
| Nutsedge | 2C,9G | 3C,9G | 5C,9G |
| Crabgrass | 6G | 7G | 4G |
| Barnyardgrass | 9H | 9C | 9H |
| Cheatgrass | 4C,9G | 9C | 2C,9G |
| Wild Oats | 5C,9H | 4C,8G | 0 |
| Wheat | 3G | 2G | 0 |
| Corn | 8H | 10C | 7H |
| Soybean | 4C,9G | 9C | 3C,8G |
| Rice | 9C | 9C | 5C,9G |
| Sorghum | 2C,9G | 5C,9G | 5C,9H |
| Sugar beet | 4C,8G | 9C | 3C,7H |
| Cotton | 9C | 10C | 4C,9G |

PREEMERGENCE

| | | | |
|---|---|---|---|
| Morningglory | 9G | 9G | 9G |
| Cocklebur | 9H | 9H | 9H |
| Velvetleaf | 4C,9G | 9C | 9C |
| Nutsedge | 6G | 10E | 10E |
| Crabgrass | 4G | 4G | 0 |
| Barnyardgrass | 4G | 5C,9H | 4C,8H |
| Cheatgrass | 8H | 9H | 8H |
| Wild Oats | 2C,8G | 5C,9G | 2C,5G |
| Wheat | 2C,5G | 2C,9G | 0 |
| Corn | 4C,8G | 3U,9G | 3C,7G |
| Soybean | 3C,5H | 9H | 3C,3H |
| Rice | 10E | 10E | 4C,9H |
| Sorghum | 9H | 9H | 4C,9H |
| Sugar beet | 4C,8G | 9G | 9G |
| Cotton | 9G | 9G | 9G |

| Compound 40 | Cmpd. 41 |
|---|---|

TABLE A-continued

| | | | |
|---|---|---|---|
| Rate kg/ha | 0.05 | 0.01 | 0.05 |
| POSTEMERGENCE | | | |
| Morningglory | 10C | 10C | 10C |
| Cocklebur | 10C | 9C | 10C |
| Velvetleaf | 10C | 10C | 9C |
| Nutsedge | 3C,9G | 2C,8G | 8G |
| Crabgrass | 5G | 2G | 2C,6G |
| Barnyardgrass | 9H | 4C,8H | 5C,9H |
| Cheatgrass | 9C | 5C,9G | 4C,9G |
| Wild Oats | 3C,9G | 4C,9G | 4C,9G |
| Wheat | 5G | 3G | 2C,9G |
| Corn | 2C,9H | 2C,9H | 5U,9G |
| Soybean | 9C | 9C | 5C,9G |
| Rice | 9C | 5C,9G | 5C,9G |
| Sorghum | 3C,9G | 3C,9H | 4C,9H |
| Sugar beet | 4C,9G | 4C,8G | 9C |
| Cotton | 9C | 4C,9G | 4C,8G |
| PREEMERGENCE | | | |
| Morningglory | 3C,9G | 8G | 9G |
| Cocklebur | 8H | 8H | 8H |
| Velvetleaf | 9C | 9C | 2G |
| Nutsedge | 9G | 8G | 5G |
| Crabgrass | 5G | 0 | 4G |
| Barnyardgrass | 8G | 3C,6G | 2C,5G |
| Cheatgrass | 4C,9H | 9H | 2C,7G |
| Wild Oats | 4C,6G | 2C,8G | 4C,8G |
| Wheat | 5G | 5G | 2C,8G |
| Corn | 3C,8H | 8G | 3C,9H |
| Soybean | 3C,6H | 2C,4G | 3C,4H |
| Rice | 10E | 4C,9H | 10E |
| Sorghum | 5C,9H | 4C,8H | 5C,9H |
| Sugar beet | 10E | 10C | 5C,9G |
| Cotton | 9G | 8G | 2C,8G |

| | Cmpd. 42 | Cmpd. 43 | Cmpd. 44 | Cmpd. 45 |
|---|---|---|---|---|
| Rate kg/ha | 0.05 | 0.05 | 0.05 | 0.05 |
| POSTEMERGENCE | | | | |
| Morningglory | 5C,9G | 1C,3G | 2C,7G | 4C,8H |
| Cocklebur | 3G | 2C,8H | 8G | 2C,8G |
| Velvetleaf | 4C,9G | 2C,5G | 4C,9H | 4C,9G |
| Nutsedge | 5G | 5G | 4C,9G | 4C,9G |
| Crabgrass | 3C,6G | 0 | 3C,6G | 2C,6G |
| Barnyardgrass | 2H | 2C,5H | 3C,6H | 5C,9H |
| Cheatgrass | 5G | 3C,9G | 5C,9G | 5C,9G |
| Wild Oats | 5C,9G | 3C,9G | 7G | 2C,8G |
| Wheat | 8G | 3G | 2G | 2G |
| Corn | 10C | 7H | 3C,9G | 4U,9G |
| Soybean | 9C | 3C,7H | 9C | 9C |
| Rice | 9C | 4C,9G | 5C,9G | 5C,9G |
| Sorghum | 9C | 4C,9H | 9C | 9C |
| Sugar beet | 9C | 4C,8G | 9C | 9C |
| Cotton | 5C,9G | 4C,7G | 4C,8H | 4C,9G |
| PREEMERGENCE | | | | |
| Morningglory | 2C,9G | 0 | 6G | 5G |
| Cocklebur | 4G | 0 | 3H | 8H |
| Velvetleaf | 3G | 3G | 9C | 9C |
| Nutsedge | 0 | 0 | 4C,9G | 10E |
| Crabgrass | 2C | 0 | 2C,5G | 6G |
| Barnyardgrass | 2C,6G | 0 | 3C,8H | 9H |
| Cheatgrass | 3C,5GT | 8G | 9H | 10E |
| Wild Oats | 2C,7G | 2C,6G | 4C,8G | 8G |
| Wheat | 2C,7G | 2G | 4C,8G | 8G |
| Corn | 4C,9H | 2G | 4C,9G | 2C,8G |
| Soybean | 3C,5G | 1H | 3C,4H | 3H,5G |
| Rice | 10E | 4C,6G | 10E | 9H |
| Sorghum | 4C,9H | 2C,3G | 3C,9G | 3C,9G |
| Sugar beet | 10E | 3C,6G | 9C | 10C |
| Cotton | 3C,5G | 2G | 8G | 4G |

| | Cmpd. 46 | Cmpd. 47 | Cmpd. 48 | Cmpd. 49 |
|---|---|---|---|---|
| Rate kg/ha | 0.05 | 0.05 | 0.05 | 0.05 |
| POSTEMERGENCE | | | | |
| Morningglory | 6G | 5C,9G | 2G | 2G |
| Cocklebur | 2C,9G | 3G | 0 | 4C,9G |
| Velvetleaf | 0 | 3C,5G | 3G | 1H |
| Nutsedge | 9G | 0 | 0 | 2C,5G |
| Crabgrass | 0 | 2G | 0 | 0 |
| Barnyardgrass | 8H | 7H | 2H | 3C,8H |
| Cheatgrass | 5G | 2C,8G | 0 | 3G |
| Wild Oats | 0 | 9G | 0 | 0 |
| Wheat | 0 | 4G | 0 | 2G |
| Corn | 3H | 4U,9C | 2C,7H | 7H |
| Soybean | 2C,5G | 9C | 4C,9G | 5C,9G |
| Rice | 5G | 4C,9G | 8G | 9C |
| Sorghum | 3C,8H | 4C,9H | 6H | 3C,8G |
| Sugar beet | 2G | 9C | 4C,8G | 3C,4H |
| Cotton | 1H | 4C,9H | 2C,5G | 3C,5H |
| PREEMERGENCE | | | | |
| Morningglory | 3G | 4H | 0 | 7G |
| Cocklebur | 2G | 0 | 0 | 4G |
| Velvetleaf | 5G | 4C,9G | 0 | 5G |
| Nutsedge | 5G | 0 | 0 | 3G |
| Crabgrass | 2G | 0 | 0 | 0 |
| Barnyardgrass | 3H | 1H | 0 | 0 |
| Cheatgrass | 8G | 7H | 0 | 3G |
| Wild Oats | 0 | 4G | 0 | 0 |
| Wheat | 0 | 2C,6G | 0 | 0 |
| Corn | 5G | 2C,6G | 0 | 0 |
| Soybean | 0 | 2H | 0 | 2C,3H |
| Rice | 9H | 2C,5G | 0 | 8H |
| Sorghum | 3C,8H | 3C,5G | 0 | 3C,6H |
| Sugar beet | 7G | 4C,9G | 6G | 3H |
| Cotton | 0 | 6G | 0 | 0 |

| | Cmpd. 50 | Cmpd. 51 | Cmpd. 52 | Cmpd. 53 |
|---|---|---|---|---|
| Rate kg/ha | 0.05 | 0.05 | 0.05 | 0.05 |
| POSTEMERGENCE | | | | |
| Morningglory | 8G | 6H | 1C,2G | 2C,5G |
| Cocklebur | 5C,9G | 10C | 4C,9G | 0 |
| Velvetleaf | 5C,9H | 5C,9G | 1C | 3C,7G |
| Nutsedge | 4C,9G | 3C,9G | 4G | 0 |
| Crabgrass | 3G | 5G | 0 | 0 |
| Barnyardgrass | 6C,9H | 9C | 9H | 3H |
| Cheatgrass | 8G | 3C,8G | 0 | 0 |
| Wild Oats | 2C,5G | 3G | 0 | 0 |
| Wheat | 8G | 3G | 0 | 0 |
| Corn | 3U,9G | 9C | 6H | 2C,9G |
| Soybean | 9C | 9C | 3C,7G | 4C,9G |
| Rice | 6C,9G | 9C | 6G | 8G |
| Sorghum | 3U,9G | 3U,9H | 3C,8G | 3G |
| Sugar beet | 5C,9G | 4C,9G | 2C,3H | 9C |
| Cotton | 5C,9G | 4C,9G | 2C,4G | 4C,9G |
| PREEMERGENCE | | | | |
| Morningglory | 9G | 9G | 6G | 2G |
| Cocklebur | 9H | 8H | 7H | 3H |
| Velvetleaf | 9C | 8G | 5C,9G | 3G |
| Nutsedge | 9G | 4C,9G | 3G | 0 |
| Crabgrass | 2C,6G | 2G | 0 | 0 |
| Barnyardgrass | 5C,9H | 3C,9H | 3C,7H | 0 |
| Cheatgrass | 5C,9H | 8G | 5G | 0 |
| Wild Oats | 2C,8G | 3C,8G | 0 | 0 |
| Wheat | 7G | 3C,9H | 0 | 0 |
| Corn | 3C,9H | 3C,9H | 4G | 3G |
| Soybean | 9H | 3C,8H | 3C,3H | 2C,2H |
| Rice | 10E | 3C,9H | 4C,8H | 0 |
| Sorghum | 10E | 5C,9H | 3C,7H | 2C,3H |
| Sugar beet | 10C | 9G | 5G | 3C,5G |
| Cotton | 10C | 9G | 2G | 3G |

| | Cmpd. 54 | Cmpd. 55 | Compound 56 | |
|---|---|---|---|---|
| Rate kg/ha | 0.05 | 0.05 | 0.05 | 0.01 |
| POSTEMERGENCE | | | | |
| Morningglory | 0 | 2C | 4C,9G | 3C,5G |
| Cocklebur | 0 | 4C,5G | 2C,9G | 2C,7G |
| Velvetleaf | 0 | 5C,8H | 9C | 4C,8H |
| Nutsedge | 0 | 0 | 6G | 2C,4G |
| Crabgrass | 0 | 2G | 2C,8G | 2G |
| Barnyardgrass | 0 | 3C,6H | 4C,9H | 2H |
| Cheatgrass | 0 | 2C,5G | 2C,9G | 2C,8G |
| Wild Oats | 0 | 0 | 2C,7G | 0 |
| Wheat | 0 | 0 | 0 | 0 |
| Corn | 3G | 1H | 3C,7H | 4H |
| Soybean | 3C,4H | 3C,4H | 4CF,9G | 5C,9G |
| Rice | 2G | 4C,6G | 4C,9G | 4C,9G |
| Sorghum | 0 | 3C,4G | 3C,9G | 3C,6G |
| Sugar beet | 1H | 3C,4H | 4C,8H | 2C |
| Cotton | 3C,4G | 4C,7G | 4C,9H | 4C,8G |
| PREEMERGENCE | | | | |
| Morningglory | 0 | 4G | 9G | 3G |
| Cocklebur | 0 | 0 | 9H | 3G |
| Velvetleaf | 0 | 0 | 8G | 3G |

TABLE A-continued

| | | | | |
|---|---|---|---|---|
| Nutsedge | 0 | 0 | 0 | 0 |
| Crabgrass | 0 | 0 | 5G | 4G |
| Barnyardgrass | 0 | 0 | 7G | 1C |
| Cheatgrass | 0 | 0 | 3C,8G | 5G |
| Wild Oats | 0 | 0 | 9G | 5G |
| Wheat | 0 | 0 | 0 | 0 |
| Corn | 0 | 0 | 2C,8G | 3G |
| Soybean | 0 | 0 | 3C,7H | 3C,4H |
| Rice | 0 | 0 | 3C,8H | 2G |
| Sorghum | 0 | 0 | 3C,7G | 2G |
| Sugar beet | 0 | 5G | 8G | 6G |
| Cotton | 0 | 0 | 6G | 4G |

| | Cmpd. 57 | Cmpd. 58 | Cmpd. 59 | Cmpd. 60 |
|---|---|---|---|---|
| Rate kg/ha | 0.05 | 0.05 | 0.05 | 0.05 |
| POSTEMERGENCE | | | | |
| Morningglory | 0 | 5G | 8G | 0 |
| Cocklebur | 2G | 7G | 7G | 0 |
| Velvetleaf | 0 | 2C,7G | 3C,8H | 0 |
| Nutsedge | 2C | 3C,8G | 5G | 0 |
| Crabgrass | 0 | 0 | 7G | 0 |
| Barnyardgrass | 0 | 3C,7H | 3C,9H | 0 |
| Cheatgrass | 8G | 4C,9G | 2C,9G | 0 |
| Wild Oats | 2C,8G | 3C,8G | 3C,9G | 2C,8G |
| Wheat | 0 | 0 | 2G | 0 |
| Corn | 2G | 3C,9H | 3C,9H | 3C,9G |
| Soybean | 1H | 3C,9G | 5C,9G | 0 |
| Rice | 3G | 2C,9G | 5C,9G | 8G |
| Sorghum | 3C,7G | 3C,9H | 4C,9H | 2C,7G |
| Sugar beet | 2C,6G | 5C,9G | 5C,9G | 0 |
| Cotton | 2G | 2C,5G | 4C,8H | 0 |
| PREEMERGENCE | | | | |
| Morningglory | 0 | 3H | 3C,6G | 0 |
| Cocklebur | 0 | 5H | — | 0 |
| Velvetleaf | 0 | 5G | 5G | 0 |
| Nutsedge | 0 | 5G | 10E | 0 |
| Crabgrass | 0 | 0 | 2G | 0 |
| Barnyardgrass | 0 | 0 | 4G | 0 |
| Cheatgrass | 0 | 2G | 8G | 0 |
| Wild Oats | 0 | 2C,5G | 3C,8G | 0 |
| Wheat | 0 | 0 | 2G | 0 |
| Corn | 0 | 2C,5G | 3C,6G | 3G |
| Soybean | 0 | 1C | 2C | 0 |
| Rice | 0 | 2C,5G | 3C,8G | 3G |
| Sorghum | 0 | 2C,4G | 3C,7G | 2G |
| Sugar beet | 0 | 3C,8G | 3C,7G | 0 |
| Cotton | 0 | 6G | 4G | 0 |

| | Cmpd. 61 | Cmpd. 62 | Cmpd. 63 | Cmpd. 64 |
|---|---|---|---|---|
| Rate kg/ha | 0.05 | 0.05 | 0.05 | 0.05 |
| POSTEMERGENCE | | | | |
| Morningglory | 0 | 3G | 2C,5G | 9C |
| Cocklebur | 0 | 2C,7G | 9C | 10C |
| Velvetleaf | 0 | 0 | 4C,9G | 9C |
| Nutsedge | 0 | 9G | 4C,9G | 4C,9G |
| Crabgrass | 0 | 0 | 0 | 4G |
| Barnyardgrass | 0 | 2C,7H | 1C,4H | 4C,9H |
| Cheatgrass | 0 | 4G | 8G | 9C |
| Wild Oats | 0 | 0 | 10C | 4C,8G |
| Wheat | 0 | 0 | 5G | 4G |
| Corn | 0 | 2H | 5G | 5C,9G |
| Soybean | 0 | 1H | 4C,9G | 4C,9G |
| Rice | 3G | 0 | 9C | 9C |
| Sorghum | 2G | 3C,7H | 4C,9H | 4C,9H |
| Sugar beet | 1H | 2H | 9C | 9C |
| Cotton | 0 | 0 | 4C,9H | 4C,9G |
| PREEMERGENCE | | | | |
| Morningglory | 0 | 0 | 1C | 8H |
| Cocklebur | 0 | — | — | 9H |
| Velvetleaf | 0 | 0 | 0 | 9C |
| Nutsedge | 0 | 0 | 0 | 3C,8G |
| Crabgrass | 0 | 0 | 0 | 2C |
| Barnyardgrass | 0 | 0 | 0 | 5C,9H |
| Cheatgrass | 0 | 0 | 8G | 10H |
| Wild Oats | 0 | 0 | 2C,7H | 5C,9G |
| Wheat | 0 | 0 | 0 | 7G |
| Corn | 0 | 0 | 5G | 5C,9H |
| Soybean | 0 | 0 | 1C | 4C,8H |
| Rice | 0 | 0 | 3C,8G | 10E |
| Sorghum | 0 | 0 | 3C,7G | 10H |
| Sugar beet | 0 | 0 | 8G | 9G |
| Cotton | 0 | 0 | 2G | 9G |

| | Cmpd. 65 | Cmpd. 66 | Cmpd. 67 | Cmpd. 68 |
|---|---|---|---|---|
| Rate kg/ha | 0.05 | 0.05 | 0.05 | 0.05 |
| POSTEMERGENCE | | | | |
| Morningglory | 10C | 5C,9G | 3C,9H | 4C,8G |
| Cocklebur | 10C | 4C,9H | 3G | 5C,9G |
| Velvetleaf | 10C | 3C,8G | 4C,9G | 2C,6G |
| Nutsedge | 5C,9G | 3C,7G | 0 | 4C,9G |
| Crabgrass | 7G | 2C,5G | 2G | 0 |
| Barnyardgrass | 9C | 9C | 9C | 3C,8H |
| Cheatgrass | 9C | 4C,9G | 8G | 5G |
| Wild Oats | 10C | 9C | 9C | 0 |
| Wheat | 4G | 9G | 9G | 0 |
| Corn | 9C | 10C | 9C | 4G |
| Soybean | 5C,9G | 5C,9G | 5C,9G | 3C,7G |
| Rice | 9C | 9C | 9C | 4C,9G |
| Sorghum | 9C | 9C | 4C,9G | 9H |
| Sugar beet | 9C | 9C | 9C | 3C,6G |
| Cotton | 4C,9G | 4C,9H | 4C,9H | 4C,9G |
| PREEMERGENCE | | | | |
| Morningglory | 9G | 10E | 7H | 7G |
| Cocklebur | 9H | 3G | 6H | — |
| Velvetleaf | 5C,9G | 2C | 1C | 2G |
| Nutsedge | 9G | 3C,5G | 0 | 8G |
| Crabgrass | 4C,5G | 2C | 0 | 0 |
| Barnyardgrass | 9H | 4C,8H | 0 | 3C,8H |
| Cheatgrass | 10H | 8G | 2G | 2C,8G |
| Wild Oats | 9G | 9C | 2C,4G | 0 |
| Wheat | 9G | 3C,9H | 2C,5G | 0 |
| Corn | 9G | 4C,9G | 3C,9G | 5G |
| Soybean | 9H | 2C,4G | 1C | 1C |
| Rice | 10E | 9H | 9H | 9H |
| Sorghum | 5C,9H | 4C,9H | 3C,8H | 4C,9H |
| Sugar beet | 9C | 3C,8G | 8G | 8G |
| Cotton | 8G | 4G | 3C,3H | 6G |

| | Cmpd. 69 | Cmpd. 70 | Cmpd. 71 | Cmpd. 72 |
|---|---|---|---|---|
| Rate kg/ha | 0.05 | 0.05 | 0.05 | 0.05 |
| POSTEMERGENCE | | | | |
| Morningglory | 0 | 4C,9G | 10C | 5G |
| Cocklebur | 2G | 7H | 7G | 2G |
| Velvetleaf | 2G | 8G | 4C,9G | 0 |
| Nutsedge | 5G | 3C,8G | 4C,8G | 2G |
| Crabgrass | 0 | 2C,3G | 3C,8H | 0 |
| Barnyardgrass | 2H | 3C,8H | 5C,9H | 0 |
| Cheatgrass | 3C,7G | 2C,8G | 8G | 4G |
| Wild Oats | 3C,7G | 2C,3G | 3C,5G | 2C,8G |
| Wheat | 0 | 0 | 3G | 0 |
| Corn | 2C,3G | 4C,9H | 2C,9H | 3C,9H |
| Soybean | 3C,5G | 4C,9H | 9C | 2C,8G |
| Rice | 3C,7G | 5C,9G | 4C,9G | 6G |
| Sorghum | 3C,5G | 3C,9H | 4C,9H | 3C,8H |
| Sugar beet | 10C | 10C | 10C | 3C,6G |
| Cotton | 3C,7H | 3C,9H | 9H | 0 |
| POSTEMERGENCE | | | | |
| Morningglory | 0 | 4G | 8G | 0 |
| Cocklebur | 0 | 0 | 7G | 2G |
| Velvetleaf | 0 | 4G | 7G | 0 |
| Nutsedge | 0 | 0 | 0 | 0 |
| Crabgrass | 0 | 4G | 5G | 0 |
| Barnyardgrass | 0 | 3C,7G | 3C,8H | 0 |
| Cheatgrass | 0 | 3C,8G | 9H | 0 |
| Wild Oats | 0 | 6G | 2C,6G | 0 |
| Wheat | 0 | 0 | 2G | 0 |
| Corn | 0 | 3C,7G | 3C,8G | 0 |
| Soybean | 0 | 3C,7H | 2C,7H | 0 |
| Rice | 0 | 2C,8H | 3C,9H | 0 |
| Sorghum | 0 | 3C,7G | 3C,8H | 0 |
| Sugar beet | 5G | 3C,9G | 7G | 0 |
| Cotton | 0 | 8G | 8G | 0 |

| | Cmpd. 73 | Cmpd. 74 | Cmpd. 75 | Cmpd. 76 |
|---|---|---|---|---|
| Rate kg/ha | 0.05 | 0.05 | 0.05 | 0.05 |
| POSTEMERGENCE | | | | |
| Morningglory | 2C,8H | 2C,5G | 10C | 10C |
| Cocklebur | 2H | 2C,6G | 10C | 9C |
| Velvetleaf | 3C,8H | 2C,5G | 9C | 9C |
| Nutsedge | 0 | 0 | 2C,8G | 2C,8G |
| Crabgrass | 0 | 0 | 2G | 0 |
| Barnyardgrass | 0 | 0 | 8H | 3C,9H |

TABLE A-continued

| | | | | |
|---|---|---|---|---|
| Cheatgrass | 0 | 0 | 3C,6G | 8G |
| Wild Oats | 0 | 0 | 3G | 3C,5G |
| Wheat | 0 | 0 | 2G | 2C,5G |
| Corn | 2C,6H | 0 | 2C,9H | 4C,9H |
| Soybean | 2C,9G | 2C,8H | 2C,9H | 9C |
| Rice | 3G | 7G | 2C,9H | 5C,9H |
| Sorghum | 0 | 2C,5G | 9H | 4C,9H |
| Sugar beet | 9C | 1H | 2C,5H | 3C,8H |
| Cotton | 3C,8H | 7G | 4C,9H | 9C |

PREEMERGENCE

| | | | | |
|---|---|---|---|---|
| Morningglory | 0 | 0 | 8H | 9H |
| Cocklebur | 6G | 0 | 9H | 9H |
| Velvetleaf | 5G | 0 | 9C | 10C |
| Nutsedge | 0 | 0 | 5G | 4C,9G |
| Crabgrass | 0 | 0 | 0 | 3G |
| Barnyardgrass | 0 | 2G | 3C,9H | 3C,5G |
| Cheatgrass | 0 | 0 | 8G | 9G |
| Wild Oats | 0 | 0 | 3C,8H | 8G |
| Wheat | 0 | 0 | 6G | 7G |
| Corn | 3G | 0 | 3C,9H | 3C,9G |
| Soybean | 2C,1H | 0 | 3C,7H | 8H |
| Rice | 2C,3G | 0 | 3C,9H | 3C,9H |
| Sorghum | 0 | 0 | 3C,8H | 9C |
| Sugar beet | 6G | 5G | 9G | 7G |
| Cotton | 0 | 0 | 2C,8H | 7G |

| | Cmpd. 77 | Cmpd. 78 | Cmpd. 79 | Cmpd. 80 |
|---|---|---|---|---|
| Rate kg/ha | 0.05 | 0.05 | 0.05 | 0.05 |

POSTEMERGENCE

| | | | | |
|---|---|---|---|---|
| Morningglory | 2C, 7G | 9C | 10C | 3C, 7H |
| Cocklebur | 10C | 9C | 9C | 3C, 7H |
| Velvetleaf | 2C, 8G | 9C | 9C | 3C, 4G |
| Nutsedge | 2G | 5G | 4G | 0 |
| Crabgrass | 0 | 3G | 0 | 0 |
| Barnyardgrass | 0 | 3C, 8H | 7H | 0 |
| Cheatgrass | 0 | 4G | 0 | 0 |
| Wild Oats | 0 | 2G | 0 | 0 |
| Wheat | 0 | 3G | 0 | 0 |
| Corn | 2G | 3C, 8H | 3C, 9H | 0 |
| Soybean | 3H, 7G | 5C, 9G | 5C, 9G | 3C, 8H |
| Rice | 7G | 5C, 9G | 5C, 9G | 7G |
| Sorghum | 5G | 3C, 9H | 4C, 9H | 2C, 5G |
| Sugar beet | 0 | 10C | 9C | 3C, 5G |
| Cotton | 8G | 4C, 9G | 5C, 9G | 3C, 6H |

PREEMERGENCE

| | | | | |
|---|---|---|---|---|
| Morningglory | 8G | 9G | 9G | 0 |
| Cocklebur | 5G | — | 9H | 0 |
| Velvetleaf | 5G | 8G | 9C | 0 |
| Nutsedge | 0 | 0 | 0 | 0 |
| Crabgrass | 0 | 0 | 0 | 0 |
| Barnyardgrass | 0 | 8H | 0 | 0 |
| Cheatgrass | 0 | 3G | 0 | 0 |
| Wild Oats | 0 | 2C, 5G | 0 | 0 |
| Wheat | 0 | 0 | 0 | 0 |
| Corn | 0 | 2C, 7G | 2C, 7G | 0 |
| Soybean | 0 | 9H | 3C, 8H | 2C |
| Rice | 5G | 3C, 7G | 2C, 8G | 0 |
| Sorghum | 2G | 10H | 3C, 9H | 3C |
| Sugar beet | 8G | 9C | 4C, 9G | 5G |
| Cotton | 5G | 4C, 8H | 8G | 0 |

| | Cmpd. 81 | Cmpd. 82 | Cmpd. 83 | Cmpd. 84 |
|---|---|---|---|---|
| Rate kg/ha | 0.05 | 0.05 | 0.05 | 0.05 |

POSTEMERGENCE

| | | | | |
|---|---|---|---|---|
| Morningglory | 2C, 5G | 5C, 9G | 3C, 9H | 3C, 8G |
| Cocklebur | 3C, 4G | 5C, 9G | 10C | 5C, 9G |
| Velvetleaf | 3C, 3G | 4C, 8H | 10C | 5G |
| Nutsedge | 0 | 3C, 6G | 5C, 9G | 5G |
| Crabgrass | 0 | 0 | 0 | 0 |
| Barnyardgrass | 2H | 2C | 3C, 9H | 0 |
| Cheatgrass | 0 | 3G | 2C, 5G | 0 |
| Wild Oats | 0 | 0 | 2G | 0 |
| Wheat | 0 | 0 | 3G | 0 |
| Corn | 0 | 3C, 7H | 9G | 3G |
| Soybean | 2C, 5G | 4C, 8H | 5C, 9G | 2H, 5G |
| Rice | 4G | 5G | 8G | 5G |
| Sorghum | 4G | 2C, 4G | 3C, 3H | 4G |
| Sugar beet | 2H | 3C, 2H | 3C, 8H | 0 |
| Cotton | 2C, 3G | 3G | 5C, 9G | 2G |

POSTEMERGENCE

| | | | | |
|---|---|---|---|---|
| Morningglory | 2C | 7H | 5G | 3C, 3H |
| Cocklebur | 3H | 4C, 4H | 9C | 3C, 7H |
| Velvetleaf | 9C | 9C | 9C | 7G |
| Nutsedge | 0 | 2C | 5G | 0 |
| Crabgrass | 0 | 2G | 3G | 0 |
| Barnyardgrass | 2G | 3C | 3C, 6G | 0 |
| Cheatgrass | 2G | 7G | 8G | 0 |
| Wild Oats | 0 | 2C, 5G | 7G | 0 |
| Wheat | 0 | 4G | 5G | 0 |
| Corn | 0 | 3C, 6H | 2C, 8G | 0 |
| Soybean | 0 | 3C, 4H | 4C, 5H | 0 |
| Rice | 2C, 3G | 3C, 7H | 2C, 7G | 5G |
| Sorghum | 0 | 3C, 7H | 2C, 8G | 2G |
| Sugar beet | 9C | 8H | 8G | 8G |
| Cotton | 0 | 6G | 5G | 2C |

| | Cmpd. 85 | Cmpd. 86 | Cmpd. 87 |
|---|---|---|---|
| Rate kg/ha | 0.05 | 0.05 | 0.05 |

POSTEMERGENCE

| | | | |
|---|---|---|---|
| Morningglory | 4C,9G | 4C,9H | 3C,4H |
| Cocklebur | 6C,9G | 4C,9H | 2C |
| Velvetleaf | 4C,8H | 4C,8H | 0 |
| Nutsedge | 4G | 3G | 0 |
| Crabgrass | 4G | 0 | 0 |
| Barnyardgrass | 3C,7H | 3C,7H | 0 |
| Cheatgrass | 0 | 2G | 0 |
| Wild Oats | 3C,7G | 0 | 0 |
| Wheat | 0 | 0 | 0 |
| Corn | 3C,7H | 3C,6H | 0 |
| Soybean | 5C,9G | 5C,9G | 2C,2H |
| Rice | 4C,9G | 2C,8G | 2G |
| Sorghum | 4C,9H | 3C,9H | 2C,3H |
| Sugar beet | 5C,9G | 9C | 3C,5H |
| Cotton | 4C,8H | 3C,7H | 1C |

PREEMERGENCE

| | | | |
|---|---|---|---|
| Morningglory | 4C,8H | 3C,5H | 0 |
| Cocklebur | 8H | 9H | 0 |
| Velvetleaf | 10E | 8G | 4G |
| Nutsedge | 7G | — | 0 |
| Crabgrass | 1C | 0 | 0 |
| Barnyardgrass | 3C,5G | 2C | 0 |
| Cheatgrass | 0 | 0 | 0 |
| Wild Oats | 2C,6G | 0 | 0 |
| Wheat | 0 | 0 | 0 |
| Corn | 2C,5G | 0 | 0 |
| Soybean | 3C,7G | 3C,7G | 3C,3G |
| Rice | 3C,6H | 3C,5G | 0 |
| Sorghum | 3C,9H | 3C,7H | 3G |
| Sugar beet | 4C,8G | 9C | 0 |
| Cotton | 6G | 5G | 0 |

| | Cmpd. 88 | Cmpd. 89 | Cmpd. 90 | Cmpd. 91 |
|---|---|---|---|---|
| Rate kg/ha | 0.05 | 0.05 | 0.05 | 0.05 |

POSTEMERGENCE

| | | | | |
|---|---|---|---|---|
| Morningglory | 4C,8H | 10C | 5G | 2C,7G |
| Cocklebur | 3C,9G | 9C | 0 | 2H |
| Velvetleaf | 3C,8G | 10C | 0 | 0 |
| Nutsedge | 3C,5G | 2C,8G | 0 | 0 |
| Crabgrass | 0 | 4G | 0 | 0 |
| Giant Foxtail | 0 | 4C,9G | 0 | 0 |
| Barnyardgrass | 0 | 9H | 0 | 0 |
| Cheatgrass | 0 | 5C,9G | 0 | 0 |
| Wild Oats | 0 | 2C,4G | 0 | 0 |
| Wheat | 0 | 6G | 0 | 0 |
| Corn | 0 | 3C,9H | 0 | 0 |
| Barley | 0 | 7G | 0 | 0 |
| Soybean | 4G | 9C | 1C,3G | 2C,6G |
| Rice | 7G | 9C | 0 | 0 |
| Sorghum | 8H | 9C | 0 | 0 |
| Sugar beet | 3C,7G | 10C | 0 | 3H |
| Cotton | 3C,7G | 10C | 4G | 8G |

PREEMERGENCE

| | | | | |
|---|---|---|---|---|
| Morningglory | 8G | 9G | 0 | 0 |
| Cocklebur | 7G | 8H | 0 | 0 |
| Velvetleaf | 5G | 9G | 0 | 0 |
| Nutsedge | 0 | 8G | 0 | 0 |
| Crabgrass | 0 | 5G | 0 | 0 |
| Giant Foxtail | 2C | 9H | 0 | 0 |
| Barnyardgrass | 0 | 8H | 0 | 0 |
| Cheatgrass | 0 | 8G | 0 | 0 |
| Wild Oats | 0 | 8G | 0 | 0 |
| Wheat | 0 | 8G | 0 | 0 |

TABLE A-continued

| | | | | |
|---|---|---|---|---|
| Corn | 0 | 9G | 0 | 0 |
| Barley | 0 | 9G | 0 | 0 |
| Soybean | 0 | 7H | 0 | 0 |
| Rice | 4G | 9H | 0 | 0 |
| Sorghum | 2C,7G | 5C,9G | 0 | 0 |
| Sugar beet | 7G | 9C | 0 | 5G |
| Cotton | 5G | 8G | 0 | 0 |

| Rate kg/ha | Cmpd. 92 0.05 | Cmpd. 93 0.05 |
|---|---|---|
| POSTEMERGENCE | | |
| Morningglory | 0 | 2C,5G |
| Cocklebur | 0 | 5C,9G |
| Velvetleaf | 0 | 4C,9H |
| Nutsedge | 0 | 2C,7G |
| Crabgrass | 0 | 0 |
| Giant Foxtail | 0 | 2C,6G |
| Barnyardgrass | 0 | 9H |
| Cheatgrass | 0 | 2C,9G |
| Wild Oats | 0 | 0 |
| Wheat | 0 | 2G |
| Corn | 0 | 0 |
| Barley | 0 | 0 |
| Soybean | 3G | 5C,9G |
| Rice | 0 | 4C,9G |
| Sorghum | 0 | 4C,9H |
| Sugar beet | 0 | 4C,9G |
| Cotton | 0 | 4C,8G |
| PREEMERGENCE | | |
| Morningglory | 0 | 8G |
| Cocklebur | 0 | 7H |
| Velvetleaf | 0 | 5G |
| Nutsedge | 0 | 0 |
| Crabgrass | 0 | 0 |
| Giant Foxtail | 0 | 0 |
| Barnyardgrass | 0 | 0 |
| Cheatgrass | 0 | 0 |
| Wild Oats | 0 | 0 |
| Wheat | 0 | 0 |
| Corn | 0 | 0 |
| Barley | 0 | 2G |
| Soybean | 0 | 0 |
| Rice | 0 | 4G |
| Sorghum | 0 | 4G |
| Sugar beet | 0 | 8G |
| Cotton | 0 | 5G |

The embodiments of the invention in which an exclusive property or privilege is claimed are defined as follows:

1. A compound of the formula

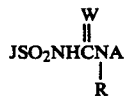
$$JSO_2NHCNA$$
with W above C, and R below N (attached to the C):

$$\underset{R}{JSO_2NH\overset{W}{\overset{\|}{C}}NA}$$

and their agriculturally suitable salts, wherein:

J is

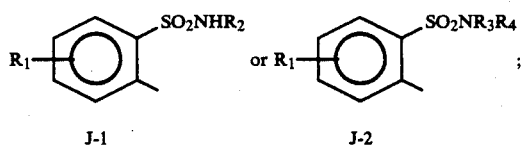

J-1      J-2

W is O or S;
R is H or $CH_3$;
$R_1$ is H, $C_1$ to $C_3$ alkyl, $C_1$ to $C_3$ haloalkyl, halogen, nitro, $C_1$ to $C_3$ alkoxy, $SO_2NR_aR_b$, $C_1$ to $C_3$ alkylthio, $C_1$ to $C_3$ alkylsulfinyl, $C_1$ to $C_3$ alkylsulfonyl, CN, $CO_2R_c$, $C_1$ to $C_3$ haloalkoxy, $C_1$ to $C_3$ haloalkylthio, $C_2$ to $C_3$ alkoxyalkyl, $C_2$ to $C_3$ haloalkoxyalkyl, $C_2$ to $C_3$ alkylthioalkyl, $C_2$ to $C_3$ haloalkylthioalkyl, $C_2$ to $C_3$ cyanoalkyl or $NR_dR_e$;

$R_a$ is H, $C_1$ to $C_4$ alkyl, $C_2$ to $C_3$ cyanoalkyl, methoxy or ethoxy;

$R_b$ is H, $C_1$ to $C_4$ alkyl or $C_3$ to $C_4$ alkenyl; or $R_a$ and $R_b$ can be taken together as $-(CH_2)_3-$, $-(CH_2)_4-$, $-(CH_2)_5-$ or $-CH_2CH_2OCH_2CH_2-$;

$R_c$ is $C_1$ to $C_4$ alkyl, $C_3$ to $C_4$ alkenyl, $C_3$ to $C_4$ alkynyl, $C_2$ to $C_4$ haloalkyl, $C_2$ to $C_3$ cyanoalkyl, $C_5$ to $C_6$ cycloalkyl, $C_4$ to $C_7$ cycloalkylalkyl or $C_2$ to $C_4$ alkoxyalkyl;

$R_d$ and $R_e$ are independently H or $C_1$ to $C_2$ alkyl;

$R_2$ is $C_2$ to $C_6$ haloalkenyl, $C_3$ to $C_6$ cycloalkyl, $C_3$ to $C_6$ cycloalkyl optionally substituted with 1 or 2 $CH_3$ groups, $C_4$ to $C_7$ cycloalkylalkyl, $C_5$ to $C_6$ cycloalkenyl, $C_3$ to $C_6$ epoxyalkyl, $C_2$ to $C_6$ haloalkyl, $CH_2CH(OR_5)_2$,

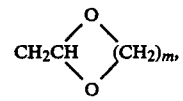

phenyl which may be optionally substituted with $R_7$,

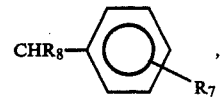

$CH_2C(O)CH_3$, CN, $OR_6$, $C_1$ to $C_6$ alkyl substituted with $OR_9$, $S(O)_nR_{10}$ or $NR_{11}R_{12}$, Q, $CHR_8Q$ or $CH_2CH_2Q$;

$R_3$ is $C_1$ to $C_6$ alkyl, $C_3$ to $C_6$ alkenyl, $C_3$ to $C_6$ alkynyl, $C_3$ to $C_6$ cycloalkyl which can be optionally substituted with 1 or 2 $CH_3$ groups, $C_4$ to $C_7$ cycloalkylalkyl, $C_5$ to $C_6$ cycloalkenyl, $C_1$ to $C_6$ haloalkyl, $C_1$ to $C_5$ alkoxy, $C_3$ to $C_6$ epoxyalkyl or $C_1$ to $C_6$ alkyl substituted with $OR_9$, $S(O)_nR_{10}$, $NR_{11}R_{12}$ or $P(O)(OR_5)_2$;

$R_4$ is $C_1$ to $C_3$ alkyl substituted with 1-3 atoms of F, Cl or Br, $C_3$ to $C_4$ alkynyl, $CH_2CH(OR_5)_2$,

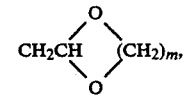

$C_2$ to $C_6$ haloalkenyl, $C_3$ to $C_6$ epoxyalkyl, $CH_2C(O)CH_3$, CN, $C_1$ to $C_6$ alkyl substituted with $OR_9$, $S(O)_nR_{10}$ or $NR_{11}R_{12}$, Q, $CHR_8Q$ or $CH_2CH_2Q$;

$R_3$ and $R_4$ can be taken together with the sulfonamide nitrogen to form a saturated 5- or 6-membered ring substituted by one or more groups selected from L or a partially saturated 5- or 6-membered ring optionally substituted by one or more groups selected from L;

$R_5$ is $C_1$ to $C_3$ alkyl;
$R_6$ is $C_1$ to $C_5$ alkyl;
$R_7$ is H, $C_1$ to $C_3$ alkyl, halogen, $NO_2$, $CF_3$, CN or $C_1$ to $C_3$ alkoxy;
$R_8$ is H or $CH_3$;
$R_9$ is H, $SO_2R_5$, $C(O)R_5$, $CO_2R_5$, $C(O)NR_{11}R_{12}$ or $P(O)(OR_5)_2$;

$R_{10}$ is $C_1$ to $C_3$ alkyl;
$R_{11}$ is H or $C_1$ to $C_3$ alkyl;
$R_{12}$ is H or $C_1$ to $C_3$ alkyl;
m is 2 or 3;
n is 0, 1 or 2;
Q is a heterocycle selected from the group pyrrolidine, pyrrole, dithiolane, tetrahydrofuran, dioxane, thiazole, thiadiazole, pyrimidine and pyridine optionally substituted by one or more groups selected from L;
L is $C_1$ to $C_4$ alkyl, $C_1$ to $C_3$ haloalkyl, halogen, $C_1$ to $C_3$ alkoxy, $C_1$ to $C_3$ alkylthio, $C_3$ to $C_4$ alkenyloxy, $C_3$ to $C_4$ alkenylthio, $C_1$ to $C_2$ haloalkoxy or $C_1$ to $C_2$ haloalkylthio;
A is

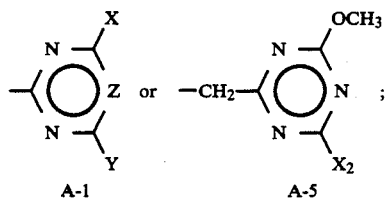

X is H, $C_1$ to $C_4$ alkyl, $C_1$ to $C_4$ alkoxy, $C_1$ to $C_4$ haloalkoxy, $C_1$ to $C_4$ haloalkyl, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino or di($C_1$ to $C_3$ alkyl)amino;
Y is H, $C_1$ to $C_4$ alkyl, $C_1$ to $C_4$ alkoxy, $C_1$ to $C_4$ haloalkoxy, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino, $C_3$ to $C_4$ alkenyloxy, $C_3$ to $C_4$ alkynyloxy, $C_2$ to $C_5$ alkylthioalkyl, $C_1$ to $C_4$ haloalkyl, $C_3$ to $C_5$ cycloalkyl, $C_2$ to $C_4$ alkynyl, $C(O)R_f$,

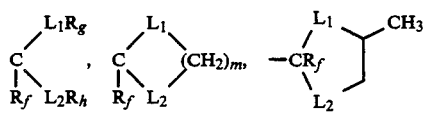

or $N(OCH_3)CH_3$;
$L_1$ and $L_2$ are independently O or S;
$R_f$ is H or $CH_3$;
$R_g$ and $R_h$ are independently $C_1$ to $C_2$ alkyl;
Z is N; and
$X_2$ is $CH_3$ or $OCH_3$;
provided that:
(a) when A is A-1, then $R_2$ is other than $CH_2CF_3$;
(b) when $R_3$ or $R_4$ is $CH_2CF_3$, then the other is $CHF_2$, $CH_2CH_2F$, $CH_2CH_2Cl$, $CH_2CH_2Br$ or $CH_2CF_3$;
(c) when $R_4$ is $CF_2H$, then $R_3$ is other than $C_1$ to $C_3$ alkyl;
(d) when $R_4$ is $C_3$ to $C_4$ alkynyl, then $R_3$ is $CHF_2$, $CH_2CH_2F$, $CH_2CH_2Cl$, $CH_2CH_2Br$ or $C_3$ to $C_4$ alkynyl;
(e) neither X nor Y is $OCF_2H$; and
(f) when $R_1$ is H, then $R_2$ is other than $OR_6$.

2. A compound according to claim 1 wherein:
W is O;
J is J-1; and
$R_2$ is $C_2$ to $C_6$ haloalkenyl, $C_3$ to $C_6$ cycloalkyl, $C_3$ to $C_6$ cycloalkyl optionally substituted with 1 or 2 $CH_3$ groups, $C_4$ to $C_7$ cycloalkylalkyl, $C_5$ to $C_6$ cycloalkenyl, $C_3$ to $C_6$ epoxyalkyl, $C_2$ to $C_6$ haloalkyl, $CH_2CH(OR_5)_2$, $OR_6$, phenyl which can be optionally substituted with $R_7$,

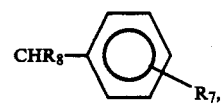

$CH_2C(O)CH_3$, CN or $C_1$ to $C_6$ alkyl substituted with $OR_9$, $S(O)_nR_{10}$ or $NR_{11}R_{12}$.

3. A compound according to claim 1 wherein:
W is O;
J is J-1; and
$R_2$ is Q, $CHR_8Q$ or $CH_2CH_2Q$.

4. A compound according to claim 1 wherein:
W is O; and
J is J-2.

5. A compound according to claim 2 wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

6. A compound according to claim 3 wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, $CH_2F$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

7. A compound according to claim 4 wherein:
R is H;
$R_1$ is H, $C_1$ to $C_2$ alkyl, F, Cl, Br, $NO_2$, $C_1$ to $C_2$ alkoxy, $C_1$ to $C_2$ alkylthio, $C_1$ to $C_2$ haloalkoxy, $CH_2OCH_3$, $CH_2SCH_3$ or $CH_2CN$ and is not para to the sulfonylurea bridge;
A is A-1;
X is $CH_3$, $OCH_3$, $OCH_2CH_3$, $CH_2F$, $OCH_2CH_2F$, $OCH_2CHF_2$, $OCH_2CF_3$, $CF_3$, $CH_2Cl$ or $CH_2Br$; and
Y is H, $C_1$ to $C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $SCF_2H$, cyclopropyl, $C\equiv CH$, $C\equiv CCH_3$ or $CH(OCH_3)_2$.

8. A compound according to claim 5 wherein:
$R_1$ is H, Cl, $OCH_3$, $OCF_2H$, $CH_2OCH_3$ or $CH_2CN$;
$R_2$ is $C_3$ to $C_6$ cycloalkyl, $C_2$ to $C_4$ haloalkenyl, $CH_2CH_2F$, $CH_2CH_2Cl$ or $CH_2CH_2Br$;
X is $CH_3$, $OCH_3$, $OCH_2CH_3$, or $OCH_2CF_3$; and Y is $CH_3$, $OCH_3$, $CH_2CH_3$, $CH_2OCH_3$, $NHCH_3$ or $CH(OCH_3)_2$.

9. A compound according to claim 6 wherein:
$R_1$ is H, Cl, $OCH_3$, $OCF_2H$, $CH_2OCH_3$ or $CH_2CN$;
$R_2$ is Q or $CH_2Q$;
X is $CH_3$, $OCH_3$, $OCH_2CH_3$, or $OCH_2CF_3$; and
Y is $CH_3$, $OCH_3$, $CH_2CH_3$, $CH_2OCH_3$, $NHCH_3$ or $CH(OCH_3)_2$.

10. A compound according to claim 7 wherein:
$R_1$ is H, Cl, $OCH_3$, $OCF_2H$, $CH_2OCH_3$ or $CH_2CN$;
$R_3$ is $C_1$ to $C_3$ alkyl, $C_3$ to $C_4$ alkenyl, $C_3$ to $C_4$ alkynyl, $C_3$ to $C_6$ cycloalkyl or $C_1$ to $C_2$ haloalkyl;
$R_4$ is $C_2$ to $C_4$ haloalkenyl or $C_3$ to $C_4$ epoxyalkyl;
X is $CH_3$, $OCH_3$, $OCH_2CH_3$, or $OCH_2CF_3$; and
Y is $CH_3$, $OCH_3$, $CH_2CH_3$, $CH_2OCH_3$, $NHCH_3$ or $CH(OCH_3)_2$.

11. The compound of claim 1 that is N-cyclopropyl-N'-[(4-methoxy-6-methyl-1,3,5-triazin-2-yl)aminocarbonyl]-1,2-benzenedisulfonamide.

12. A composition for the control of undesired vegetation consisting essentially of a compound of claim 1 and at least one of (a) a surface active agent, and (b) a solid or liquid diluent.

13. A composition for the control of undesired vegetation consisting essentially of a compound of claim 2 and at least one of (a) a surface active agent, and (b) a solid or liquid diluent.

14. A composition for the control of undesired vegetation consisting essentially of a compound of claim 3 and at least one of (a) a surface active agent, and (b) a solid or liquid diluent.

15. A composition for the control of undesired vegetation consisting essentially of a compound of claim 4 and at least one of (a) a surface active agent, and (b) a solid or liquid diluent.

16. A composition for the control of undesired vegetation consisting essentially of a compound of claim 5 and at least one of (a) a surface active agent, and (b) a solid or liquid diluent.

17. A composition for the control of undesired vegetation consisting essentially of a compound of claim 6 and at least one of (a) a surface active agent, and (b) a solid or liquid diluent.

18. A composition for the control of undesired vegetation consisting essentially of a compound of claim 7 and at least one of (a) a surface active agent, and (b) a solid or liquid diluent.

19. A composition for the control of undesired vegetation consisting essentially of a compound of claim 8 and at least one of (a) a surface active agent, and (b) a solid or liquid diluent.

20. A composition for the control of undesired vegetation consisting essentially of a compound of claim 9 and at least one of (a) a surface active agent, and (b) a solid or liquid diluent.

21. A composition for the control of undesired vegetation consisting essentially of a compound of claim 10 and at least one of (a) a surface active agent, and (b) a solid or liquid diluent.

22. A composition for the control of undesired vegetation consisting essentially of the compound of claim 11 and at least one of (a) a surface active agent, and (b) a solid or liquid diluent.

23. A method for the control of undesirable vegetation comprising applying to the locus of such vegetation an herbicidally effective amount of a compound of claim 1.

24. A method for the control of undesirable vegetation comprising applying to the locus of such vegetation an herbicidally effective amount of a compound of claim 2.

25. A method for the control of undesirable vegetation comprising applying to the locus of such vegetation an herbicidally effective amount of a compound of claim 3.

26. A method for the control of undesirable vegetation comprising applying to the locus of such vegetation an herbicidally effective amount of a compound of claim 4.

27. A method for the control of undesirable vegetation comprising applying to the locus of such vegetation an herbicidally effective amount of a compound of claim 5.

28. A method for the control of undesirable vegetation comprising applying to the locus of such vegetation an herbicidally effective amount of a compound of claim 6.

29. A method for the control of undesirable vegetation comprising applying to the locus of such vegetation an herbicidally effective amount of a compound of claim 7.

30. A method for the control of undesirable vegetation comprising applying to the locus of such vegetation an herbicidally effective amount of a compound of claim 8.

31. A method for the control of undesirable vegetation comprising applying to the locus of such vegetation an herbicidally effective amount of a compound of claim 9.

32. A method for the control of undesirable vegetation comprising applying to the locus of such vegetation an herbicidally effective amount of a compound of claim 10.

33. A method for the control of undesirable vegetation comprising applying to the locus of such vegetation an herbicidally effective amount of the compound of claim 11.

* * * * *